United States Patent
Romanov

(10) Patent No.: US 10,385,214 B2
(45) Date of Patent: Aug. 20, 2019

(54) FLUORESCENT DYES AND THEIR USES AS BIOMARKERS

(71) Applicant: Illumina Cambridge Limited, NR Saffron Walden, Essex (GB)

(72) Inventor: Nikolai Romanov, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

(21) Appl. No.: 15/719,216

(22) Filed: Sep. 28, 2017

(65) Prior Publication Data

US 2018/0094140 A1    Apr. 5, 2018

Related U.S. Application Data

(60) Provisional application No. 62/402,635, filed on Sep. 30, 2016.

(51) Int. Cl.
| | |
|---|---|
| *C07D 417/04* | (2006.01) |
| *C09B 62/36* | (2006.01) |
| *C12Q 1/6869* | (2018.01) |
| *C07D 491/04* | (2006.01) |
| *C09K 11/06* | (2006.01) |

(52) U.S. Cl.
CPC .......... *C09B 62/365* (2013.01); *C07D 417/04* (2013.01); *C07D 491/04* (2013.01); *C09K 11/06* (2013.01); *C12Q 1/6869* (2013.01)

(58) Field of Classification Search
CPC ................................................... C07D 417/04
See application file for complete search history.

(56) References Cited

U.S. PATENT DOCUMENTS

| | | |
|---|---|---|
| 4,035,740 A | 7/1977 | Schäfer et al. |
| 5,302,509 A | 4/1994 | Cheeseman |
| 6,172,218 B1 | 1/2001 | Brenner |
| 6,465,178 B2 | 10/2002 | Chappa et al. |
| 2013/0079232 A1 | 3/2013 | Kain et al. |
| 2014/0079923 A1 | 3/2014 | George et al. |
| 2015/0274976 A1 | 10/2015 | Romanov et al. |

FOREIGN PATENT DOCUMENTS

| | | |
|---|---|---|
| WO | WO 98/44151 | 10/1998 |
| WO | WO 00/06770 | 2/2000 |
| WO | WO 00/18957 | 4/2000 |
| WO | WO 00/31148 | 6/2000 |
| WO | WO 00/50525 A1 | 8/2000 |
| WO | WO 00/53812 | 9/2000 |
| WO | WO 01/01143 | 1/2001 |
| WO | WO 01/57248 | 8/2001 |
| WO | WO 02/12566 | 2/2002 |
| WO | WO 03/014392 | 2/2003 |
| WO | WO 2004/018493 | 3/2004 |
| WO | WO 2004/018497 | 3/2004 |
| WO | WO 2005/024010 | 3/2005 |
| WO | WO 2005/047301 | 5/2005 |
| WO | WO 2005/065814 | 7/2005 |
| WO | WO 2006/120433 | 11/2006 |
| WO | WO 2007/020457 | 2/2007 |
| WO | WO 2007/135368 | 11/2007 |
| WO | WO 2014/135223 A1 | 9/2014 |
| WO | WO 2014/139596 | 9/2014 |
| WO | WO 2018/060482 A1 | 4/2018 |

OTHER PUBLICATIONS

Database Registry (online). Database Accession No. 343612-36-2. Jun. 27, 2001. Chemical Abstracts Service, Columbus, OH. XP-002776081.
Database Registry (online). Database Accession No. 343612-35-1. Jun. 27, 2001. Chemical Abstracts Service, Columbus, OH. XP-002776082.
International Search Report and Written Opinion of the International Searching Authority dated Dec. 17, 2017 for International Application No. PCT/EP2017/074880 filed Sep. 29, 2017, 18 pages.
Margulies et al. 2005. Genome sequencing in open microfabricated high density picoliter reactors. *Nature*, 437:376-380.
Mujumdar et al. 1993. Cyanine dye labeling reagents: Sulfoindocyanine succinimidyl esters. *Bioconjugate Chemistry*, 4(2):105-111.
Scheit, K. H. (1980). *Nucleotide analogs: Synthesis and biological function*. New York: John Wiley & Sons, TOC, 5 pages.
Shendure et al. 2005. Accurate multiplex polony sequencing of an evolved bacterial genome. *Science*, 309(5741):1728-1732.
Uhlman et al. 1990. Antisense oligonucleotides: A new therapeutic principle. *Chemical Reviews*, 90(4):543-584.

*Primary Examiner* — Shawquia Jackson
(74) *Attorney, Agent, or Firm* — Knobbe, Martens, Olson & Bear, LLP

(57) ABSTRACT

The present application relates to new fluorescent dyes and their uses as fluorescent labels. The compounds may be used as fluorescent labels for nucleotides in nucleic acid sequencing applications.

46 Claims, 4 Drawing Sheets

FLUORESCENT DYES AND THEIR USES AS BIOMARKERS

INCORPORATION BY REFERENCE TO ANY PRIORITY APPLICATIONS

This application claims the benefit of U.S. Provisional Application No. 62/402,635, entitled New Fluorescent Dyes and Their Uses as Biomarkers, filed Sep. 30, 2016, the disclosure of which is incorporated herein by reference in its entirety.

BACKGROUND

Field

The present application relates to new benzopyran derivatives for use as fluorescent dyes. The compounds may be used as fluorescent labels, particularly for nucleotide labeling in nucleic acid sequencing applications.

Background

Non-radioactive detection of nucleic acids utilizing fluorescent labels is an important technology in molecular biology. Many procedures employed in recombinant DNA technology previously relied heavily on the use of nucleotides or polynucleotides radioactively labeled with, for example $^{32}P$. Radioactive compounds permit sensitive detection of nucleic acids and other molecules of interest. However, there are serious limitations in the use of radioactive isotopes such as their expense, limited shelf life and more importantly safety considerations. Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced simplifying experimental protocols and facilitating the production of application-specific reagent kits. In multi-color automated DNA sequencing for example, multiplex fluorescent detection allows for the analysis of multiple nucleotide bases in a single electrophoresis lane thereby increasing throughput over single-color methods and reducing uncertainties associated with inter-lane electrophoretic mobility variations.

However, multiplex fluorescent detection can be problematic and there are a number of important factors which constrain selection of fluorescent labels. First, it is difficult to find dye compounds whose absorption and emission spectra are suitably spectrally resolved. In addition when several fluorescent dyes are used together, simultaneous excitation may be difficult because the absorption bands of the dyes for different spectral regions are usually widely separated. Many excitation methods use high power lasers and therefore the dye must have sufficient photo-stability to withstand such laser excitation. A final consideration of particular importance in molecular biology methods is that the fluorescent dyes must be compatible with the reagent chemistries used such as for example DNA synthesis solvents and reagents, buffers, polymerase enzymes and ligase enzymes.

As sequencing technology advances a need has developed for further fluorescent dye compounds, their nucleic acid conjugates and dye sets which satisfy all of the above constraints and which are amenable particularly to high throughput molecular methods such as solid phase sequencing and the like.

PCT Publication No. WO 2007/135368 describes a class of rhodamine compounds suitable for use as fluorescent labels. The compounds described therein are suitable for use in solid phase nucleic acid sequencing protocols. Advances in the technology and throughput of solid phase nucleic acid sequencing have led to further developments and improvements to the molecular design of fluorescent labels, particularly in the context of the interaction between the fluorescent reagents and particular nucleic acid sequences.

Fluorescent dye molecules with improved fluorescence properties (such as Stokes shift, fluorescence intensity, position of fluorescence maximum and shape of fluorescence band) can improve the speed and accuracy of nucleic acid sequencing. Stokes Shift is a key aspect in the identifying of the fluorescent signals in biological applications. For example, the detection of emitted light can be difficult to distinguish from the excitation light when using fluorophores with absorption and fluorescence max very close to each other (i.e., small Stokes shift), because the excitation and emission bands greatly overlap. In contrast, fluorophores with large Stokes shifts are easy to distinguish because of the greater separation between the excitation and emission wavelengths. The Stokes shift is especially critical in multiplex fluorescence applications, because the emission wavelength of one fluorophore may overlap, and therefore excite, another fluorophore in the same sample. In addition, fluorescence signal intensity is especially important when measurements are made in water based biological buffers and/or at higher temperature as fluorescence of most dyes is significantly lower at such conditions. Moreover, the nature of the base to which a dye is attached also affects the fluorescence maximum, fluorescence intensity and other spectral dye properties. The sequence specific interactions between the fluorescent dye and the nucleobase can be tailored by specific design of the fluorescent dyes. Optimization of the structure of the fluorescent dyes can improve their fluorescent properties and also improve the efficiency of nucleotide incorporation, reduce the level of sequencing errors and decrease the usage of reagents in, and therefore the costs of, nucleic acid sequencing.

Described herein are novel benzopyran derivatives and their use as bio-molecule labels, particularly as labels for nucleotides used in nucleic acid sequencing. The improvements can be seen in the greater Stokes shifts of such dyes when prepared as bio-molecule conjugates and in the length, intensity and quality of sequencing read obtainable using the new fluorescent compounds.

SUMMARY

Some embodiments described herein are related to new benzopyran derivatives of Formula (I) or mesomeric forms thereof:

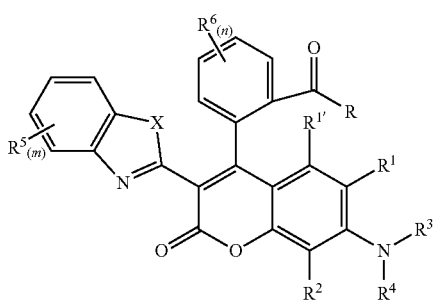

(I)

wherein each $R^1$, $R^2$, and $R^{1'}$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl or optionally substituted 5-10 membered heterocyclyl;

alternatively, $R^2$ and $R^4$ together with the atoms to which they are attached form a ring or ring system selected from the group consisting of optionally substituted 5-10 membered heteroaryl and optionally substituted 5-10 membered heterocyclyl;

$R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

R is selected from —$OR^7$ or —$NR^8R^9$;

$R^7$ is selected from the group consisting of H, alkyl, substituted alkyl, optionally substituted aryl, optionally substituted heteroaryl, optionally substituted carbocyclyl, and optionally substituted heterocyclyl;

each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl;

X is selected from the group consisting of O, S, $NR^{10}$, and Se;

$R^{10}$ is selected from the group consisting of H, alkyl, substituted alkyl, optionally substituted aryl, optionally substituted heteroaryl, optionally substituted carbocyclyl, and optionally substituted heterocyclyl;

m is an integer selected from 0 to 4; and n is an integer selected from 0 to 4; provided that when each $R^1$, $R^{1'}$ and $R^2$ is H; each $R^3$ and $R^4$ is ethyl; each m and n is 0; R is —$NHCH(CH_3)CH_2OH$; then X is selected from O, S or Se;

when each $R^1$, $R^{1'}$ and $R^2$ is H; each $R^3$ and $R^4$ is ethyl; each m and n is 0; R is -OH; then X is selected from S or Se;

when each $R^1$, $R^{1'}$ and $R^2$ is H; each $R^3$ and $R^4$ is ethyl; m is 1 and $R^5$ is methyl; n is 0; R is —OH or -OEt; then X is selected from S, $NR^{10}$ or Se; and when each $R^1$, $R^{1'}$ and $R^2$ is H; each $R^3$ and $R^4$ is ethyl; m is 1 and $R^5$ is —$S(O_2)Et$; n is 0; R is —OH or -OEt; then X is selected from S, $NR^{10}$ or Se.

Some additional embodiments described herein are related to a fluorescent compound of Formula (V) with a Stokes shift ranging from about 60 nm to about 100 nm:

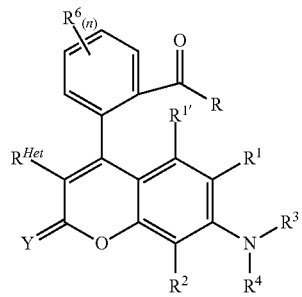

(V)

wherein each $R^1$, $R^{1'}$ and $R^2$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfo, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl or optionally substituted 5-10 membered heterocyclyl;
alternatively, $R^2$ and $R^4$ together with the atoms to which they are attached form a ring or ring system selected from the group consisting of optionally substituted 5-10 membered heteroaryl and optionally substituted 5-10 membered heterocyclyl;
$R^{Het}$ is a heteroaryl optionally substituted with one or more $R^5$;
each $R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;
R is selected from $-OR^7$ or $-NR^8R^9$;
Y is selected from O or NH;
$R^7$ is selected from the group consisting of H, alkyl, substituted alkyl, optionally substituted aryl, optionally substituted heteroaryl, optionally substituted carbocyclyl, and optionally substituted heterocyclyl;
each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl; and
n is an integer of 0 to 4.

Some embodiments described herein are related to nucleotide or oligonucleotide labeled with a compound of Formula (I) or (V).

Some embodiments described herein are related to kits containing one or more nucleotides where at least one nucleotide is a nucleotide labeled with a fluorescent dye described herein.

Some further embodiments described herein are related to methods of sequencing including incorporating a labeled nucleotide described herein in a sequencing assay, and detecting the labeled nucleotide.

Some additional embodiments described herein are related to a method of preparing a compound of Formula (Ia), the methods include reacting a compound of Formula (IIa)

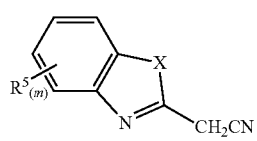

or Formula (IIb)

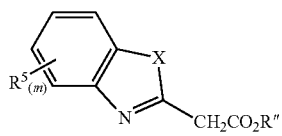

with a compound of Formula (III)

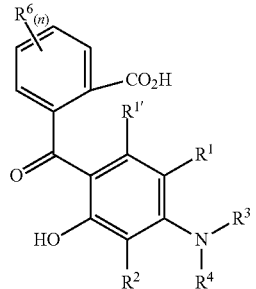

to form

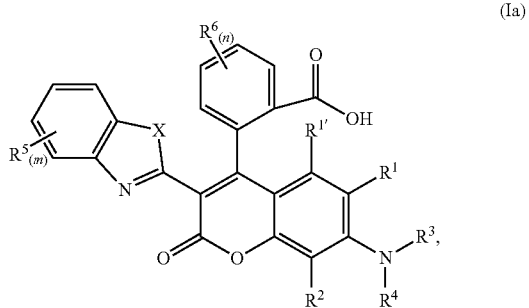

where the variables $R^1$, $R^{1'}$, $R^2$, $R^3$, $R^4$, $R^5$, $R^6$, X, m and n are defined above in the disclosure of compounds of Formula (I), and R" is selected from the group consisting of H, optionally substituted alkyl, alkenyl, alkynyl, aminoalkyl, haloalkyl, heteroalkyl, alkoxyalkyl, sulfo, optionally substituted aryl; optionally substituted heteroaryl, optionally substituted carbocyclyl, and optionally substituted heterocyclyl.

Some additional embodiments described herein are related to a method of preparing a compound of Formula (Ia'), the methods include reacting a compound of Formula (IIa)

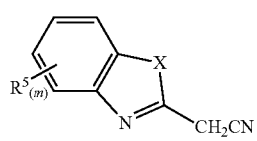

or Formula (IIb)

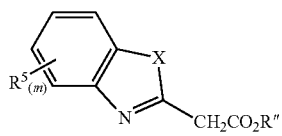

with a compound of Formula (IIIa)

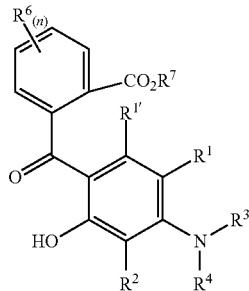

to form

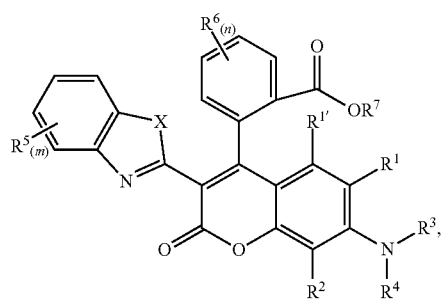

where the variables $R^1$, $R^{1'}$, $R^2$, $R^3$, $R^4$, $R^5$, $R^6$, $R^7$, R'', X, m and n are defined above.

Some additional embodiments described herein are related to a method of preparing a compound of Formula (Ia'), the method includes converting a compound of Formula (Ia) to a compound of Formula (Ia') through carboxylic acid activation:

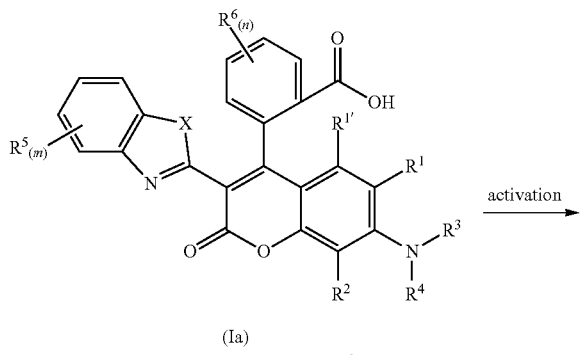

where the variables $R^1$, $R^{1'}$, $R^2$, $R^3$, $R^4$, $R^5$, $R^6$, $R^7$, $R^8$, $R^9$, X, m and n are defined above in the disclosure of compounds of Formula (I).

Some additional embodiments described herein are related to a method of preparing a compound of Formula (Ib), the method includes converting a compound of Formula (Ia) to a compound of Formula (Ia') through carboxylic acid activation:

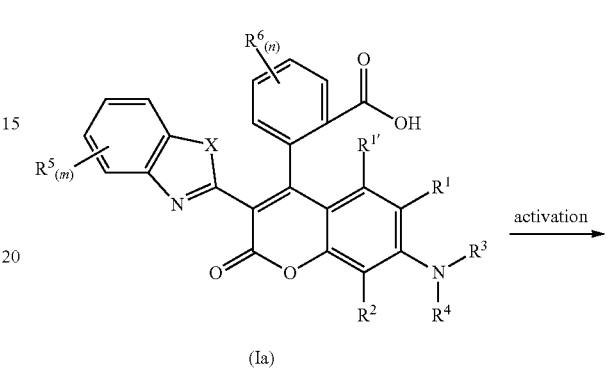

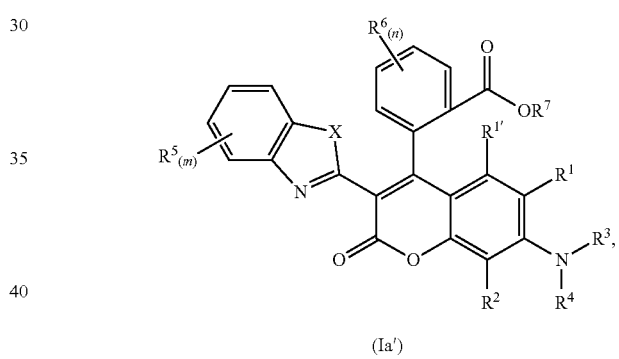

and reacting the compound of Formula (Ia') with a primary or secondary amine of Formula (IV),

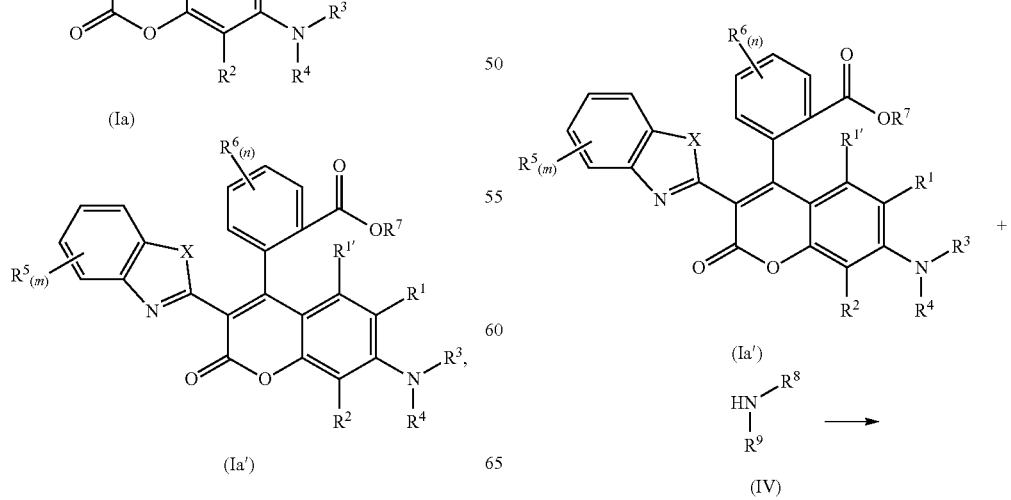

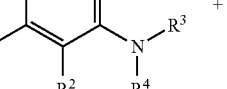

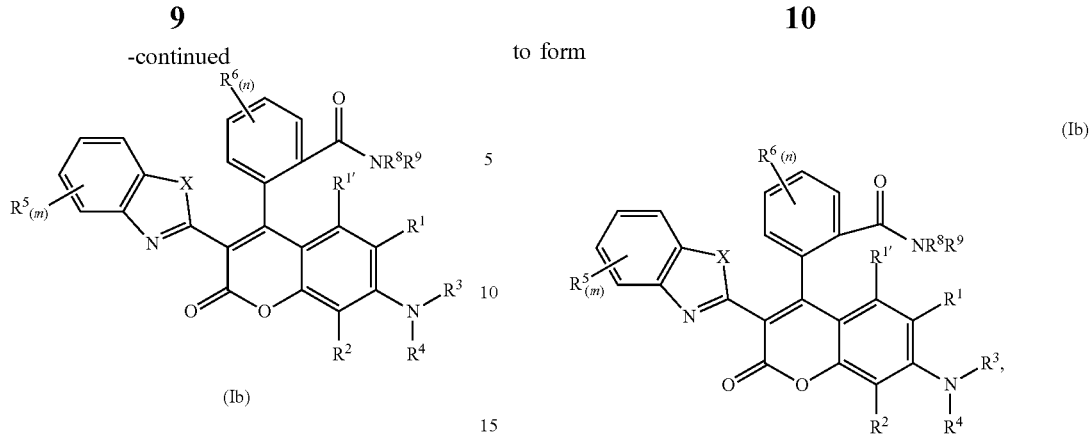

(Ib)

where the variables $R^1$, $R^{1'}$, $R^2$, $R^3$, $R^4$, $R^5$, $R^6$, $R^7$, $R^8$, $R^9$, X, m and n are defined above in the disclosure of compounds of Formula (I).

Some additional embodiments described herein are related to a method of preparing a compound of Formula (Ib), the methods include reacting a compound of Formula (IIa)

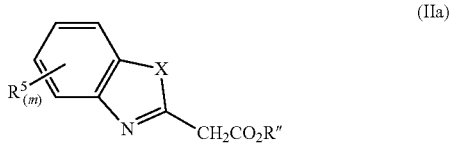

(IIa)

or Formula (IIb)

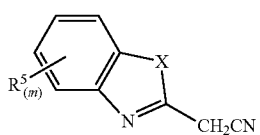

(IIb)

with a compound of Formula (IIIb)

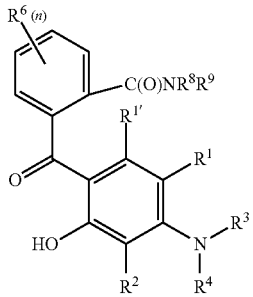

(IIIb)

to form

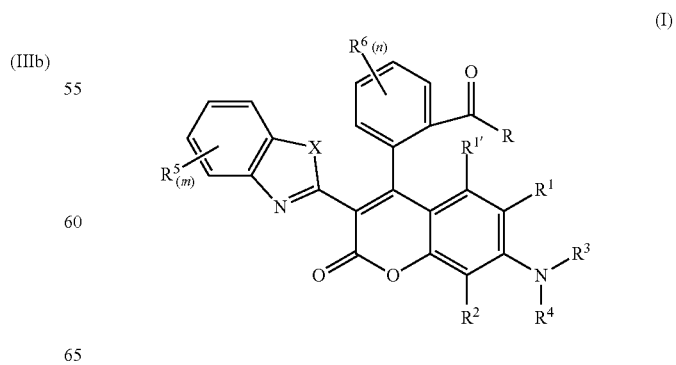

(Ib)

where the variables $R^1$, $R^{1'}$, $R^2$, $R^3$, $R^4$, $R^5$, $R^6$, $R^7$, R", X, m and n are defined above.

DETAILED DESCRIPTION

Figure 1:
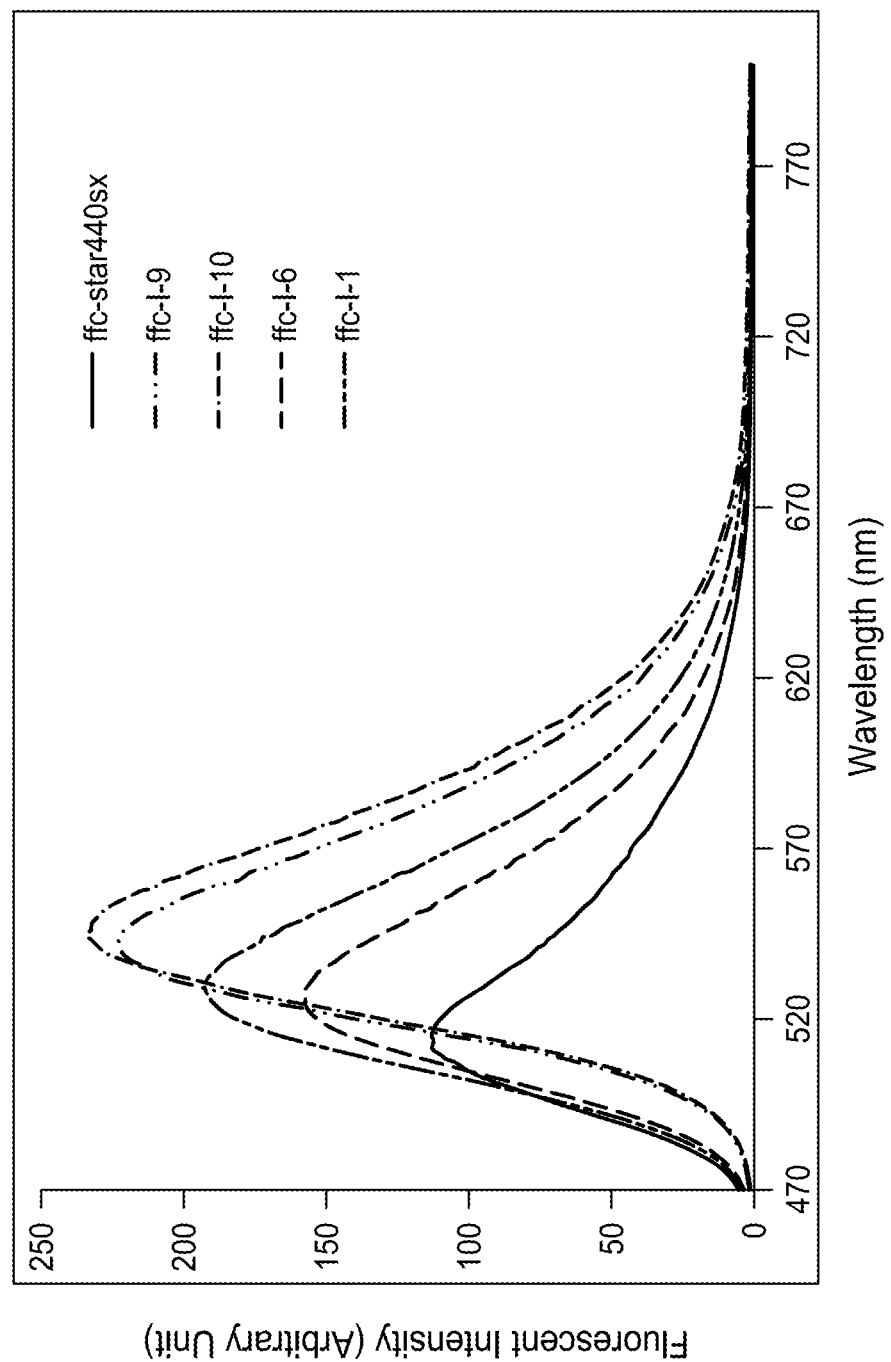
FIG. 1 is a line graph that illustrates the fluorescent spectra of the benzopyran fluorescent dyes as described herein as compared to commercial dyes with absorption in the same spectral region.

Embodiments described herein relate to new benzopyran derivatives of the structure of Formula (I) or (V) for use as fluorescent dyes. These new fluorescent dyes have greater Stokes shifts and may be used as fluorescent labels, particularly for nucleotide labeling in nucleic acid sequencing applications. Methods of preparing these fluorescent dyes and downstream sequencing applications utilizing these dyes are also exemplified.

Some embodiments described herein are related to new benzopyran derivatives of Formula (I) or mesomeric forms thereof:

(I)

wherein each $R^1$, $R^2$, and $R^{1'}$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfo, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl or optionally substituted 5-10 membered heterocyclyl;

alternatively, $R^2$ and $R^4$ together with the atoms to which they are attached form a ring or ring system selected from the group consisting of optionally substituted 5-10 membered heteroaryl and optionally substituted 5-10 membered heterocyclyl;

$R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

R is selected from —$OR^7$ or —$NR^8R^9$;

$R^7$ is selected from the group consisting of H, alkyl, substituted alkyl, optionally substituted aryl, optionally substituted heteroaryl, optionally substituted carbocyclyl, and optionally substituted heterocyclyl;

each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl;

X is selected from the group consisting of O, S, $NR^{10}$, and Se;

$R^{10}$ is selected from the group consisting of H, alkyl, substituted alkyl, optionally substituted aryl, optionally substituted heteroaryl, optionally substituted carbocyclyl, and optionally substituted heterocyclyl;

m is an integer selected from 0 to 4; and n is an integer selected from 0 to 4; provided that when each $R^1$, $R^{1'}$ and $R^2$ is H; each $R^3$ and $R^4$ is ethyl; each m and n is 0; R is —$NHCH(CH_3)CH_2OH$; then X is selected from 0, S or Se;

when each $R^1$, $R^{1'}$ and $R^2$ is H; each $R^3$ and $R^4$ is ethyl; each m and n is 0; R is—OH; then X is selected from S or Se;

when each $R^1$, $R^{1'}$ and $R^2$ is H; each $R^3$ and $R^4$ is ethyl; m is 1 and $R^5$ is methyl; n is 0; R is —OH or -OEt; then X is selected from S, $NR^{10}$ or Se; and when each $R^1$, $R^{1'}$ and $R^2$ is H; each $R^3$ and $R^4$ is ethyl; m is 1 and $R^5$ is —$S(O_2)Et$; n is 0; R is —OH or -OEt; then X is selected from S, $NR^{10}$ or Se.

In some embodiments of the compounds of Formula (I), when each $R^1$, $R^{1'}$ and $R^2$ is H; each $R^3$ and $R^4$ is ethyl; m is 1; $R^5$ is Cl; then X is selected from S, O, or Se, preferably O.

In some embodiments of the compounds of Formula (I), the optionally substituted aryl disclosed herein is optionally substituted $C_{6-10}$ aryl, for example, phenyl. In some embodiments, the optionally substituted heteroaryl disclosed herein is optionally substituted 5-10 membered heteroaryl; more preferably, optionally substituted 5-6 membered heteroaryl. In some embodiments, the optionally substituted carbocyclyl disclosed herein is optionally substituted 3-7 membered carbocyclyl, in particular 3-7 membered cycloalkyl. In some embodiments, optionally substituted heterocyclyl disclosed herein are optionally substituted 3-7 membered heterocyclyl, more preferably 5-6 membered heterocyclyl.

In some embodiments of the compounds of Formula (I), R is —$OR^7$ and the compound of Formula (I) is also represented by Formula (Ia'):

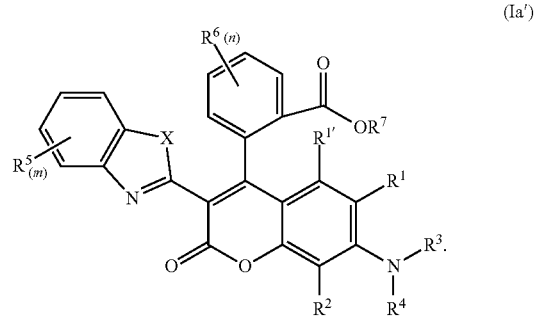

(Ia')

In one embodiment, $R^7$ is H and the compound of Formula (I) is also represented by Formula (Ia):

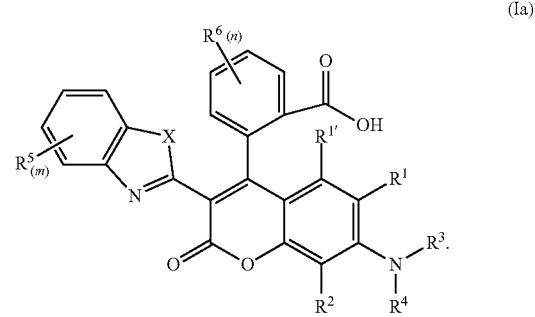

(Ia)

In some embodiments of the compounds of Formula (I), R is —$NR^8R^9$ and the compound of Formula (I) is also represented by Formula (Ib):

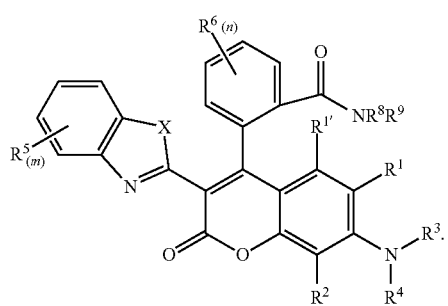

(Ib)

In one embodiment, each $R^8$ and $R^9$ is H. In some other embodiments, $R^8$ is H and $R^9$ is substituted alkyl. In some further embodiments, both $R^8$ and $R^9$ are substituted alkyl. In some such embodiments, the substituted alkyl is selected from alkyl substituted with carboxyl (—C(=O)OH), sulfo (—SO$_3$H) or sulfonate (—SO$_3^-$). In some other embodiments, the substituted alkyl is selected from alkyl substituted with C-amido group.

In some embodiments of the compounds of Formula (I), (Ia), (Ia'), or (Ib), each $R^1$, $R^{1'}$ and $R^2$ is H. In some other embodiments, at least one of $R^1$, $R^{1'}$ and $R^2$ is an alkyl.

In some embodiments of the compounds of Formula (I), (Ia), (Ia'), or (Ib), each $R^3$ and $R^4$ is an alkyl. In some such embodiments, $R^3$ and/or $R^4$ can be selected from methyl or ethyl. In some other embodiments, $R^3$ is H and $R^4$ is an alkyl. In some embodiments, $R^3$ and $R^4$ are ethyl.

In some other embodiments of the compounds of Formula (I), (Ia), (Ia'), or (Ib), $R^1$ and $R^3$ together with the atoms to which they are attached form an optionally substituted 3-7 membered heterocyclyl, for example, an optionally substituted 6 membered heterocyclyl. In some embodiments, the heterocyclyl ring has one heteroatom (i.e., nitrogen). In some other embodiments, the heterocyclyl ring may have two or more heteroatoms. In one embodiment, the optionally substituted 6-membered heterocyclyl has the structure

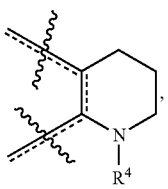

where the ----- represents either a single bond or a double bond, such that each of the carbon atoms in the ring is neutral and not charged. In some such embodiments, $R^4$ is selected from H or alkyl. In one embodiment, $R^4$ is ethyl. In some such embodiments, at least one of $R^{1'}$ and $R^2$ is H. In one embodiment, both $R^{1'}$ and $R^2$ are H.

In some other embodiments of the compounds of Formula (I), (Ia), (Ia'), or (Ib), $R^2$ and $R^4$ together with the atoms to which they are attached form an optionally substituted 3-7 membered heterocyclyl, for example, an optionally substituted 6 membered heterocyclyl. In some embodiments, the heterocyclyl ring has one heteroatom (i.e., nitrogen). In some other embodiments, the heterocyclyl ring may have two or more heteroatoms. In one embodiment, the optionally substituted 6-membered heterocyclyl has the structure

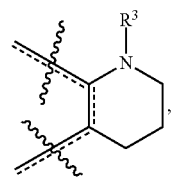

where the ----- represents either a single bond or a double bond, such that each of the carbon atoms in the ring is neutral and not charged. In some such embodiments, $R^3$ is selected from H or alkyl. In one embodiment, $R^3$ is ethyl. In some such embodiments, at least one of $R^{1'}$ and $R^1$ is H. In one embodiment, both $R^{1'}$ and $R^1$ are H.

In some alternative embodiments of the compounds of Formula (I), (Ia), (Ia'), or (Ib), $R^1$ and $R^3$ together with the atoms to which they are attached form an optionally substituted 3-7 membered heterocyclyl, for example, an optionally substituted 6 membered heterocyclyl; and $R^2$ and $R^4$ together with the atoms to which they are attached form an optionally substituted 3-7 membered heterocyclyl, for example, an optionally substituted 6 membered heterocyclyl. In some embodiments, the resulting fused heterocyclyl ring system has one heteroatom (i.e., nitrogen). In some other embodiments, the resulting fused heterocyclyl ring system may have two or more heteroatoms. In one embodiment, the resulting fused heterocyclyl ring system has the structure

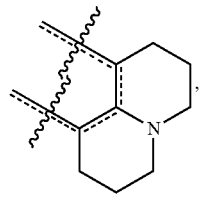

where the ----- represents either a single bond or a double bond, such that each of the carbon atoms in the ring is neutral and not charged. In one embodiment, $R^{1'}$ is H.

In some embodiments of the compounds of Formula (I), (Ia), (Ia'), or (Ib), the 3-7 membered heterocyclyl ring formed by $R^1/R^3$ and/or $R^2/R^4$ are unsubstituted. In some other embodiments, such 3-7 membered heterocyclyl is substituted with one or more alkyl, for example, methyl.

In some embodiments of the compounds of Formula (I), (Ia), (Ia'), or (Ib), m is 0. In some other embodiments, m is 1. In some such embodiments, $R^5$ is selected from sulfo, sulfonyl halide, for example, sulfonyl chloride, or aminosulfonyl. In some embodiments, $R^5$ is halogen. In some embodiments, $R^5$ is chlorine.

In some embodiments of Formula (I), (Ia), (Ia'), or (Ib), n is 0.

In any one of the embodiments of the compounds of Formula (I), (Ia), (Ia'), or (Ib) disclosed herein, X can be S (sulfur). In any one of the embodiments of the compounds of Formula (I), (Ia), (Ia'), or (Ib) disclosed herein, X can be O (oxygen). In some such embodiment, the compounds of Formula (Ia), (Ia') and (Ib) can also be represented by Formula (Ic), (Ic') and (Id) respectively:

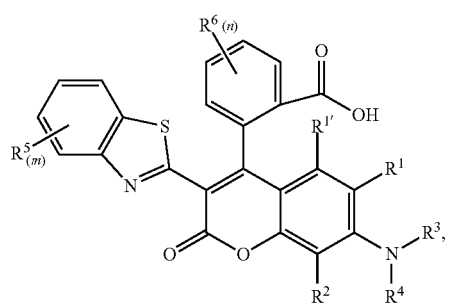
(Ic)
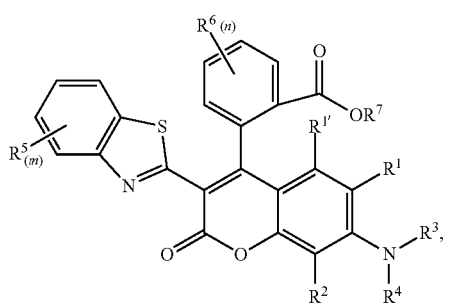
(Ic')
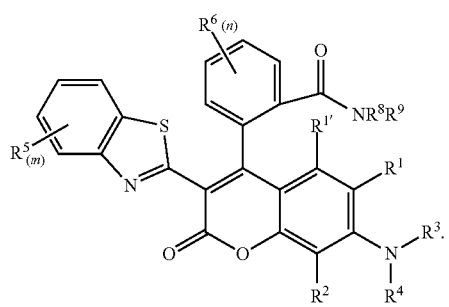
(Id)
In some specific embodiments, exemplary compounds of Formula (I) include:
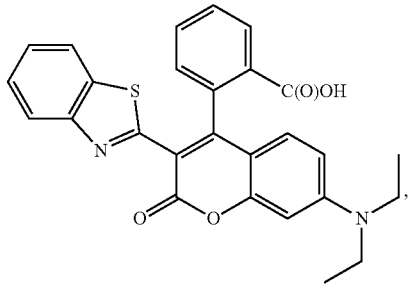
(I-1)
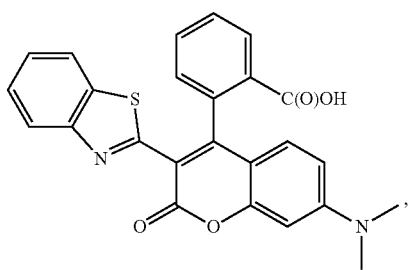
(I-2)
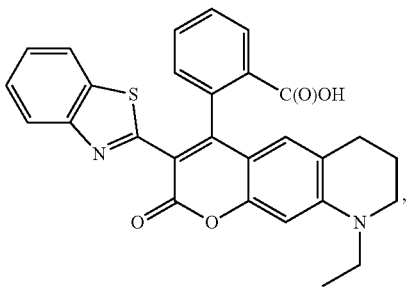
(I-3)
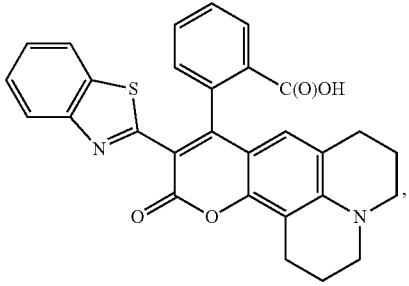
(I-4)
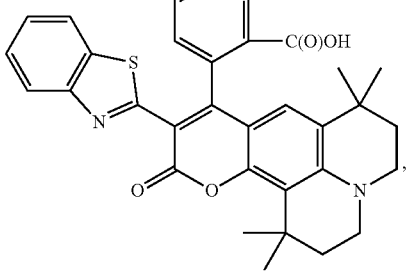
(I-5)
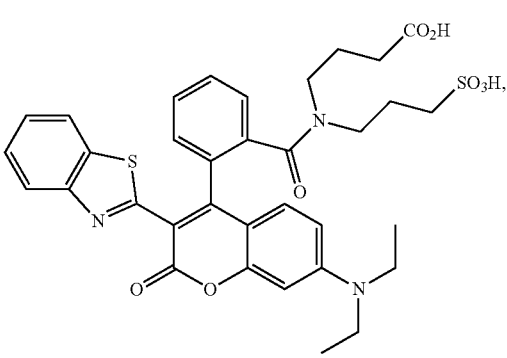
(I-6)
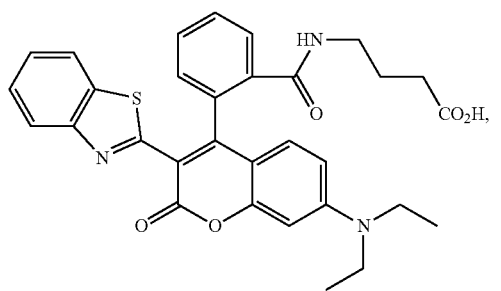
(I-7)

(I-8)
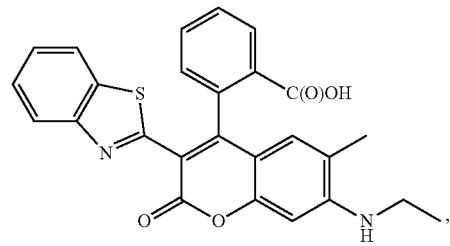
(I-9)
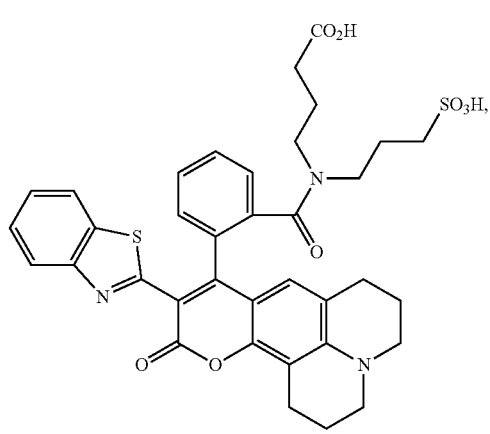
(I-10)
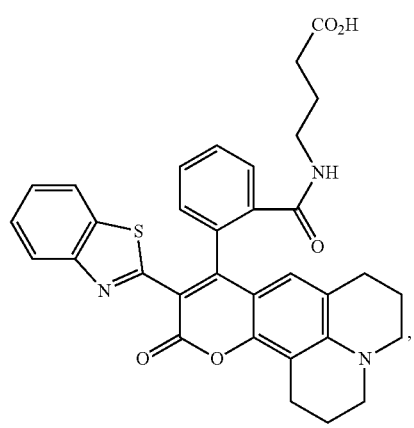
(I-11)
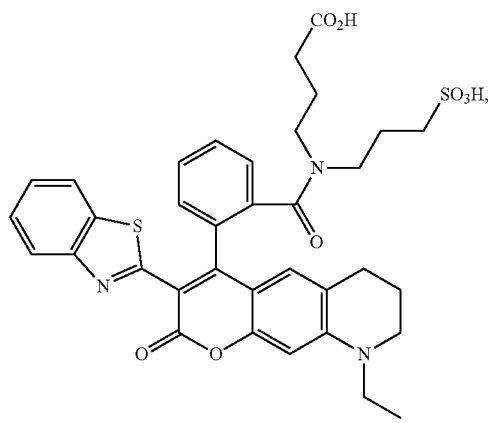
(I-12)
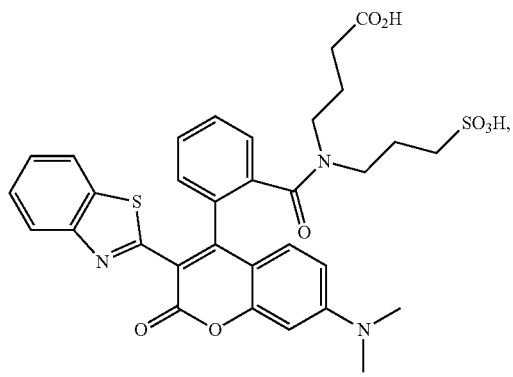
(I-13)
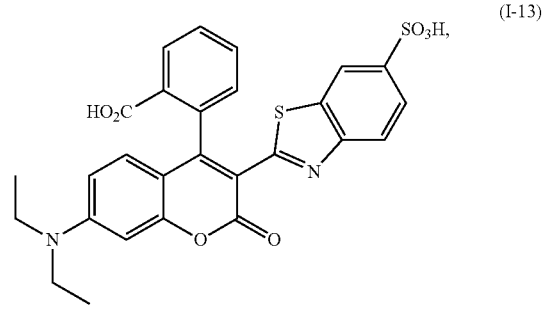
(I-14)
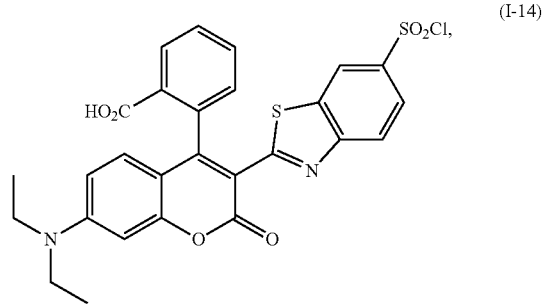
(I-15) and
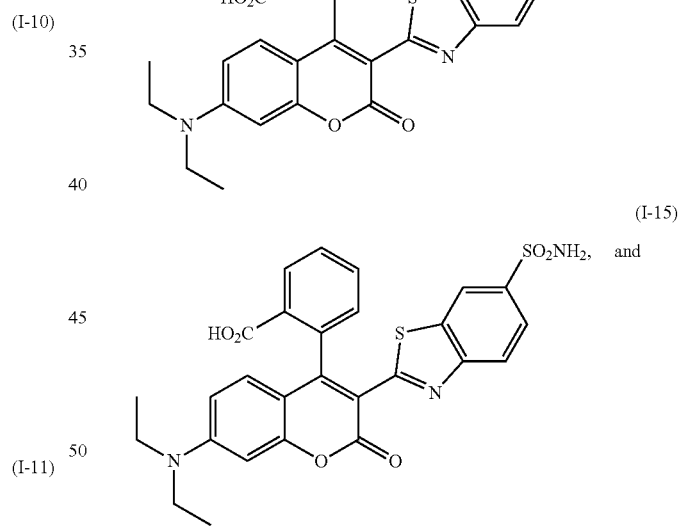
(I-16)
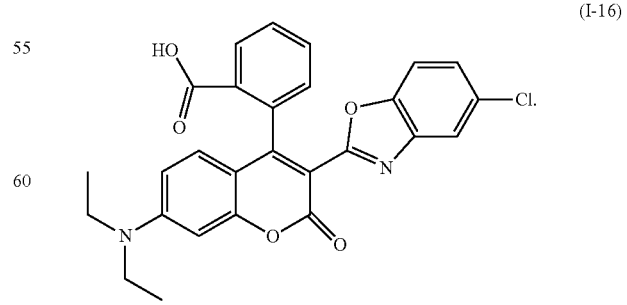
or mesomeric forms thereof.

In some embodiments of the compounds of Formula (I), the compound is covalently attached to a nucleotide or oligonucleotide via C(=O)R, wherein R is —OR⁷, and wherein R⁷ is a substituted alkyl.

In some alternative embodiments, the compound is covalently attached to a nucleotide or oligonucleotide via C(=O)R, wherein R is —NR⁸R⁹, and wherein at least one of R⁸ or R⁹ comprises at least one functional group that may be used for attachment to the biomolecules, for example, one of R⁸ or R⁹ is a substituted alkyl comprising at least one carboxyl group.

In some embodiments, the compound of Formula (I) is present in one or more mesomeric forms (I-A), (I-B) or (I-C):

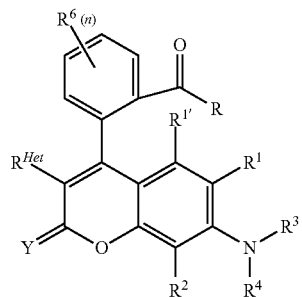

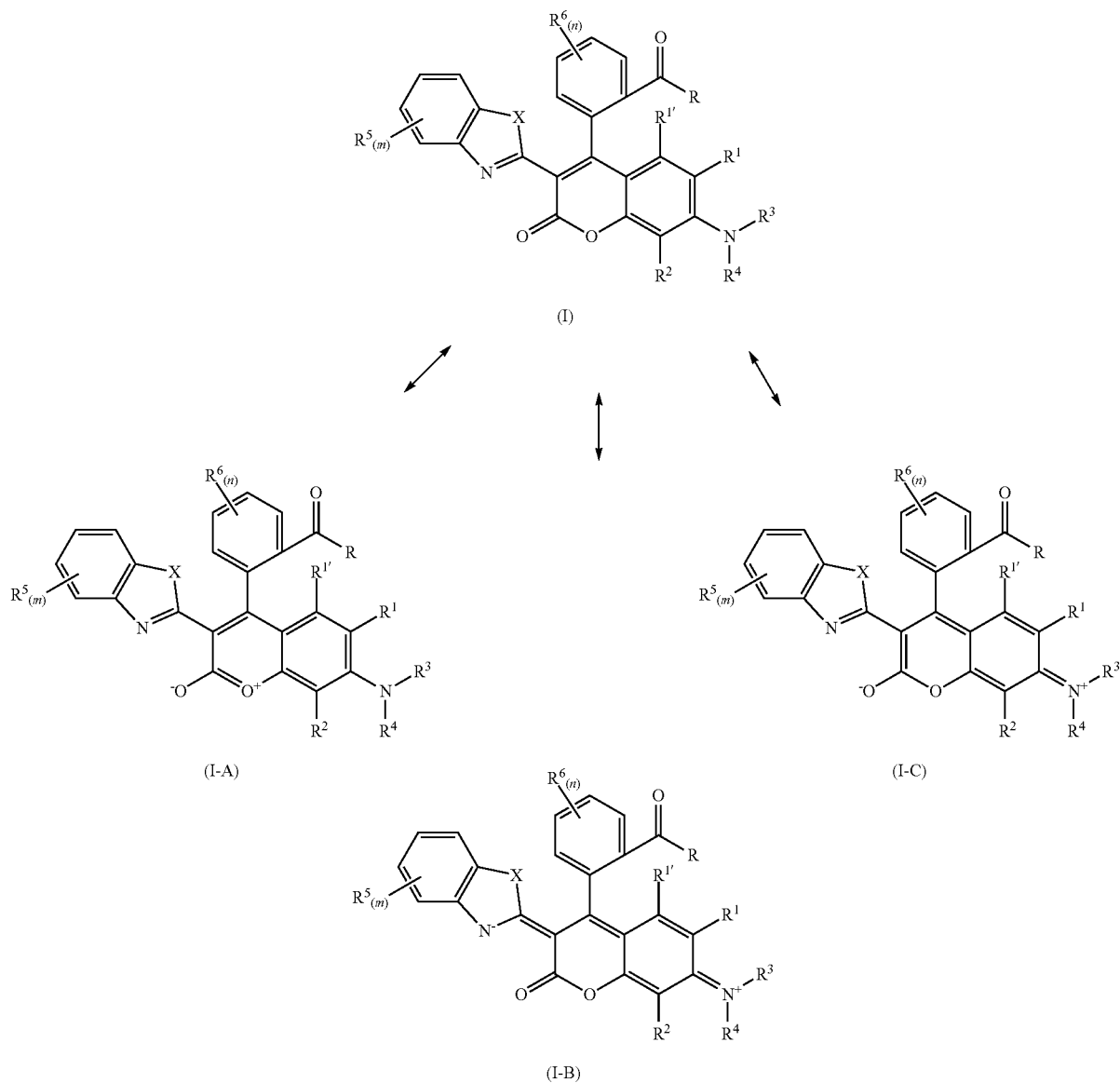

Some embodiments disclosed herein are related to a fluorescent compound of Formula (V) with a Stokes shift ranging from about 60 nm to about 100 nm:

wherein each $R^1$, $R^{1'}$ and $R^2$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfo, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl or optionally substituted 5-10 membered heterocyclyl;

alternatively, $R^2$ and $R^4$ together with the atoms to which they are attached form a ring or ring system selected from the group consisting of optionally substituted 5-10 membered heteroaryl and optionally substituted 5-10 membered heterocyclyl;

$R^{Het}$ is a heteroaryl optionally substituted with one or more $R^5$;

each $R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

R is selected from —$OR^7$ or —$NR^8R^9$;

Y is selected from O or NH;

$R^7$ is selected from the group consisting of H, alkyl, substituted alkyl, optionally substituted aryl, optionally substituted heteroaryl, optionally substituted carbocyclyl, and optionally substituted heterocyclyl;

each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl; and n is an integer of 0 to 4.

In some embodiments of Formula (V), $R^{Het}$ is selected from optionally substituted 5-10 membered heteroaryl. In some such embodiments, $R^{Het}$ is selected from optionally substituted 9 membered heteroaryl, for example, optionally substituted benzothiazole. In one embodiment, $R^{Het}$ is optionally substituted 2-benzothiazolyl:

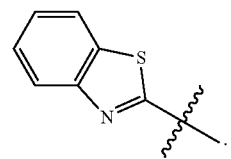 [SMILES: *c1nc2ccccc2s1]

In one embodiment, $R^{Het}$ is optionally substituted 2-benzoxazolyl with the structure

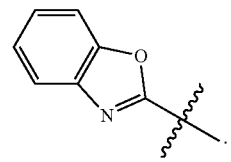 [SMILES: *c1nc2ccccc2o1]

In some such embodiments, $R^{Het}$ is substituted with one or more substituents selected from sulfo, sulfonyl halide or aminosulfonyl. In some such embodiments, $R^{Het}$ is substituted with one or more halogen. In some embodiments, $R^{Het}$ is substituted with a chlorine.

In some embodiments, R is —$OR^7$ and the compounds of Formula (V) are also represented by Formula (Va):

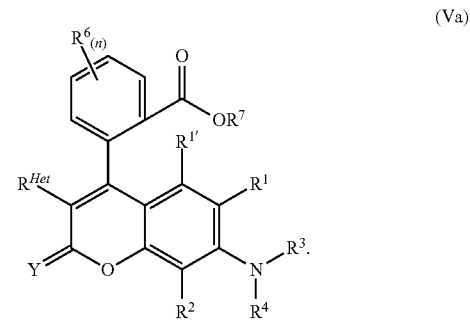

(Va)

In one embodiment, $R^7$ is H. In another embodiment, $R^7$ is substituted alkyl.

In some embodiments, R is —$NR^8R^9$ and the compounds of Formula (V) are also represented by Formula (Vb):

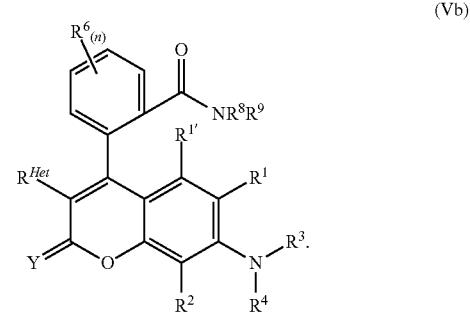

(Vb)

In one embodiment, each $R^8$ and $R^9$ is H. In some other embodiments, $R^8$ is H and $R^9$ is substituted alkyl. In some further embodiments, both $R^8$ and $R^9$ are substituted alkyl. In some such embodiments, the substituted alkyl is selected from alkyl substituted with carboxyl (—C(=O)OH) or sulfo (—SO₃H) or sulfonate (—SO₃⁻). In some other embodiments, the substituted alkyl is selected from alkyl substituted with C-amido group.

In some embodiments of the compounds of Formula (V), (Va) or (Vb), Y is O.

In some embodiments of the compounds of Formula (V), (Va) or (Vb), each $R^1$, $R^{1'}$ and $R^2$ is H. In some other embodiments, at least one of $R^1$, $R^{1'}$ and $R^2$ is an alkyl.

In some embodiments of the compounds of Formula (V), (Va) or (Vb), each $R^3$ and $R^4$ is an alkyl. In some such embodiments, $R^3$ and/or $R^4$ can be selected from methyl or ethyl. In some other embodiments, $R^3$ is H and $R^4$ is an alkyl.

In some other embodiments of the compounds of Formula (V), (Va) or (Vb), $R^1$ and $R^3$ together with the atoms to which they are attached form an optionally substituted 3-7 membered heterocyclyl, for example, an optionally substituted 6 membered heterocyclyl. In some embodiments, the heterocyclyl ring has one heteroatom (i.e., nitrogen). In some other embodiments, the heterocyclyl ring may have two or more heteroatoms. In one embodiment, the optionally substituted 6-membered heterocyclyl has the structure

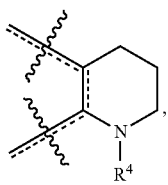

where the ----- represents either a single bond or a double bond, such that each of the carbon atoms in the ring is neutral and not charged. In some such embodiments, $R^4$ is selected from H or alkyl. In one embodiment, $R^4$ is ethyl. In some further embodiments, at least one of $R^{1'}$ and $R^2$ is H. In one embodiment, both $R^{1'}$ and $R^2$ are H.

In some other embodiments of the compounds of Formula (V), (Va) or (Vb), $R^2$ and $R^4$ together with the atoms to which they are attached form an optionally substituted 3-7 membered heterocyclyl, for example, an optionally substituted 6 membered heterocyclyl. In some embodiments, the heterocyclyl ring has one heteroatom (i.e., nitrogen). In some other embodiments, the heterocyclyl ring may have two or more heteroatoms. In one embodiment, the optionally substituted 6-membered heterocyclyl has the structure

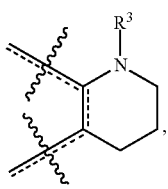

where the ----- represents either a single bond or a double bond, such that each of the carbon atoms in the ring is neutral and not charged. In some such embodiments, $R^3$ is selected from H or alkyl. In one embodiment, $R^3$ is ethyl. In some further embodiments, at least one of $R^{1'}$ and $R^1$ is H. In one embodiment, both $R^{1'}$ and $R^1$ are H.

In some alternative embodiments of the compounds of Formula (V), (Va) or (Vb), $R^1$ and $R^3$ together with the atoms to which they are attached form an optionally substituted 3-7 membered heterocyclyl, for example, an optionally substituted 6 membered heterocyclyl; and $R^2$ and $R^4$ together with the atoms to which they are attached form an optionally substituted 3-7 membered heterocyclyl, for example, an optionally substituted 6 membered heterocyclyl. In some embodiments, the resulting fused heterocyclyl ring system has one heteroatom (i.e., nitrogen). In some other embodiments, the resulting fused heterocyclyl ring system may have two or more heteroatoms. In one embodiment, the resulting fused heterocyclyl ring system has the structure

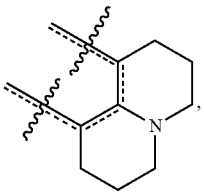

where the ----- represents either a single bond or a double bond, such that each of the carbon atoms in the ring is neutral and not charged. In one embodiment, $R^{1'}$ is H.

In some embodiments of the compounds of Formula (V), (Va) or (Vb), the 3-7 membered heterocyclyl ring formed by $R^1/R^3$ and/or $R^2/R^4$ are unsubstituted. In some other embodiments, such 3-7 membered heterocyclyl is substituted with one or more alkyl, for example, methyl.

In some embodiments of the compounds of Formula (V), (Va) or (Vb), n is 0.

In some specific embodiments of Formula (V), (Va) or (Vb), exemplary compounds of Formula (V) include compounds I-1 through I-15 as disclosed herein.

In some embodiments, the fluorescent compound of Formula (V) is covalently attached to a nucleotide or oligonucleotide via C(=O)R, wherein R is —OR⁷, and wherein $R^7$ is a substituted alkyl.

In some alternative embodiments, the fluorescent compound of Formula (V) is covalently attached to a nucleotide or oligonucleotide via C(=O)R, wherein R is —NR⁸R⁹, and wherein at least one of $R^8$ or $R^9$ is a substituted alkyl.

Definition

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:

Ac Acetyl
Ac₂O Acetic anhydride
aq. Aqueous
BOC or Boc tert-Butoxycarbonyl
BOP (Benzotriazol-1-yloxy)tris(dimethylamino)phosphonium hexafluorophosphate
cat. Catalytic
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP(s) Dideoxynucleotide(s)
DCM Methylene chloride
DMA Dimethylacetamide
DMF Dimethylformamide
Et Ethyl
EtOAc Ethyl acetate
ffN Fully functional Nucleotide Conjugate
ffC Fully functional Cytidine Conjugate
g Gram(s)
h or hr Hour(s)
IPA Isopropyl Alcohol
LCMS Liquid chromatography-mass spectrometry
MeCN Acetonitrile
mL Milliliter(s)
PG Protecting group
Ph Phenyl
ppt Precipitate
PyBOP (Benzotriazol-1-yloxy)tripyrrolidinophosphonium hexafluorophosphate
rt Room temperature
SBS Sequencing by Synthesis
TEA Triethylamine
TEAB Tetraethylammonium bicarbonate
TFA Trifluoroacetic acid
Tert, t tertiary
THF Tetrahydrofuran
TLC Thin Layer Chromatography
TSTU O—(N-Succinimidyl)-N,N,N',N'-tetramethyluronium tetrafluoroborate
μL Microliter(s)

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$ alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_{2-6}$ alkenyl" or similar designations. By way of example only, "$C_{2-6}$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_{2-6}$ alkynyl" or similar designations. By way of example only, "$C_{2-6}$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_{1-6}$ heteroalkyl" or similar designations. The heteroalkyl group may contain one or more heteroatoms. By way of example only, "$C_{1-6}$ heteroalkyl" indicates that there are one to six carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(═O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(═O)OH).

A "cyano" group refers to a "—CN" group.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfonyl hydroxide" or "sulfo" group refers to a "—S(═O)$_2$—OH" group.

A "sulfino" group refers to a "—S(═O)OH" group.

A "sulfonate" group refers to —SO$_3$—.

A "sulfonyl halide" group refers to a "—S(═O)$_2$—X" group, wherein X is a halide.

An "S-sulfonamido" group refers to a "—SO$_2$NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein.

An "N-sulfonamido" group refers to a "—N(R$_A$)SO$_2$R$_B$" group in which R$_A$ and R$_b$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein.

A "C-amido" group refers to a "—C(=O)NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein.

An "N-amido" group refers to a "—N(R$_A$)C(=O)R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein.

An "amino" group refers to a "—NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein. A non-limiting example includes free amino (i.e., —NH$_2$).

An "aminoalkyl" group refers to an amino group connected via an alkylene group.

An "aminosulfonyl" group refers to a "—S(=O)$_2$NH$_2$" group.

An "alkoxyalkyl" group refers to an alkoxy group connected via an alkylene group, such as a "C$_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from C$_1$-C$_6$ alkyl, C$_1$-C$_6$ alkenyl, C$_1$-C$_6$ alkynyl, C$_1$-C$_6$ heteroalkyl, C$_3$-C$_7$ carbocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), C$_3$-C$_7$-carbocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 3-10 membered heterocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), 3-10 membered heterocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl(C$_1$-C$_6$)alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl(C$_1$-C$_6$) alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), halo, cyano, hydroxy, C$_1$-C$_6$ alkoxy, C$_1$-C$_6$ alkoxy(C$_1$-C$_6$)alkyl (i.e., ether), aryloxy, sulfhydryl (mercapto), halo(C$_1$-C$_6$) alkyl (e.g., —CF$_3$), halo(C$_1$-C$_6$)alkoxy (e.g., —OCF$_3$), C$_1$-C$_6$ alkylthio, arylthio, amino, amino(C$_1$-C$_6$)alkyl, nitro, 0-carbamyl, N-carbamyl, 0-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, sulfo, sulfino, sulfonate, and oxo (=O). Wherever a group is described as "optionally substituted" that group can be substituted with the above substituents.

As understood by one of ordinary skill in the art, if a compound contains positively or negatively charged substituent groups, for example, SO$_{3-}$, it may also contains a negatively or positively charged counterion such that the compound as a whole is neutral.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two "adjacent" R groups are said to form a ring "together with the atom to which they are attached," it is meant that the collective unit of the atoms, intervening bonds, and the two R groups are the recited ring. For example, when the following substructure is present:

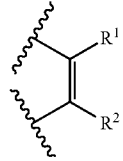

and R$^1$ and R$^2$ are defined as selected from the group consisting of hydrogen and alkyl, or R$^1$ and R$^2$ together with the atoms to which they are attached form an aryl or carbocyclyl, it is meant that R$^1$ and R$^2$ can be selected from hydrogen or alkyl, or alternatively, the substructure has structure:

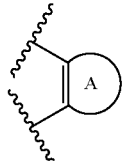

where A is an aryl ring or a carbocyclyl containing the depicted double bond.

Labeled Nucleotides

The dye compounds described herein are suitable for attachment to substrate moieties. Substrate moieties can be virtually any molecule or substance to which the fluorescent dyes described herein can be conjugated and, by way of non-limiting example, may include nucleosides, nucleotides, polynucleotides, carbohydrates, ligands, particles, solid surfaces, organic and inorganic polymers and combinations or assemblages thereof, such as chromosomes, nuclei, living cells and the like. The dyes can be conjugated by an optional linker by a variety of means including hydrophobic attraction, ionic attraction and covalent attachment. Particularly the dyes are conjugated to the substrate by covalent attachment. More particularly the covalent attachment is by means of a linker group. In some instances, such labeled nucleotides are also referred to as "modified nucleotides."

A particular useful application of the new fluorescent dyes with long Stokes shift as described herein is for labeling of biomolecules, for example, nucleotides or oligonucleotides. Some embodiments of the present application are directed to a nucleotide or oligonucleotide labeled with the new fluorescent compounds as described herein.

The attachment to the biomolecules may be via —C(=O)R moiety of the compound of Formula (I) or (V). In some embodiments, R is —$OR^7$ and $R^7$ is a substituted alkyl, which may be used for attachment to the amino group of the biomolecules. In one embodiment, —C(O)R moiety may be an activated ester residue most suitable for further amide/peptide bond formation. The term "activated ester" as used herein, refers to a carboxy group derivative which is capable of reacting in mild conditions, for example, with a compound containing an amino group. Non-limiting examples of activated esters include but not limited to p-nitrophenyl, pentafluorophenyl and succinimido esters. In some other embodiments, R is —$NR^8R^9$ and at least one of $R^8$ or $R^9$ contains at least one functional group which may be used for attachment to the biomolecules, for example, one of $R^8$ or $R^9$ is a substituted alkyl comprising at least one carboxyl.

In some embodiments, the dye compounds may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a linker moiety. The labeled nucleotide or oligonucleotide may also have a 3'-OH blocking group covalently attached to the ribose or deoxyribose sugar of the nucleotide.

Linkers

The dye compounds as disclosed herein may include a reactive linker group at one of the substituent positions for covalent attachment of the compound to another molecule. Reactive linking groups are moieties capable of forming a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Non-limiting examples of linker groups include those disclosed in PCT Publication No. WO2004/018493 (herein incorporated by reference), which connect the bases of nucleotides to labels such as, for example, the new fluorescent compounds described herein. These linkers may be cleaved using water-soluble phosphines or water-soluble transition metal catalysts formed from a transition metal and at least partially water-soluble ligands. In aqueous solution the latter form at least partially water-soluble transition metal complexes. Additional suitable linkers that may be used include those disclosed in PCT Publication No. WO2004/018493 and WO 2007/020457 (both of which are herein incorporated by references). It was discovered that by altering, and in particular increasing, the length of the linker between a fluorescent dye (fluorophore) and the guanine base, by introducing a polyethylene glycol spacer group, it is possible to increase the fluorescence intensity compared to the same fluorophore attached to the guanine base through other linkages known in the art. The design of the linkers, and especially their increased length, also allows improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —$((CH_2)_2O)_n$—, wherein n is an integer between 2 and 50, as described in WO 2007/020457.

Nucleosides and nucleotides may be labeled at sites on the sugar or nucleobase. As understood by one of ordinary skill in the art, a "nucleotide" consists of a nitrogenous base, a sugar, and one or more phosphate groups. In RNA the sugar is ribose and in DNA is a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

The dye may be attached to any position on the nucleotide base, through a linker, provided that Watson-Crick base pairing can still be carried out. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the new fluorescent dyes described herein may have the formula:

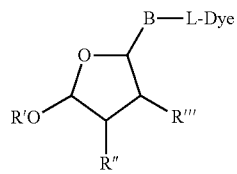

where Dye is a dye compound, B is a nucleobase, such as, for example uracil, thymine, cytosine, adenine, guanine and the like and L is an optional linker group which may or may not be present. R' can be H, monophosphate, diphosphate, triphosphate, thiophosphate, a phosphate ester analog, —O— attached to a reactive phosphorous containing group or —O— protected by a blocking group. R" can be H, OH, a phosphoramidite or a 3'-OH blocking group and R''' is H or OH; where R" is phosphoramidite, R' is an acid-cleavable hydroxyl protecting group which allows subsequent monomer coupling under automated synthesis conditions.

In some instances, the blocking group is separate and independent of the dye compound, i.e. not attached to it. Alternatively, the dye may comprise all or part of the 3'-OH blocking group. Thus R" can be a 3'-OH blocking group which may or may not comprise the dye compound. In additional alternative embodiments, there is no blocking group on the 3' carbon of the pentose sugar and the dye (or dye and linker construct) attached to the base, for example, can be of a size or structure sufficient to act as a block to the incorporation of a further nucleotide from a point other than the 3' site. Thus the block can be due to steric hindrance or can be due to a combination of size, charge and structure.

The use of a blocking group allows polymerization to be controlled, such as by stopping extension when a modified nucleotide is incorporated. If the blocking effect is reversible, for example by way of non-limiting example by changing chemical conditions or by removal of a chemical block, extension can be stopped at certain points and then allowed to continue. Non-limiting examples of 3'-OH blocking groups include those disclosed in WO 2004/018497 and WO2014/139596, which are hereby incorporated by references. For example the blocking group may be azidomethyl (—$CH_2N_3$) or substituted azidomethyl (e.g., —$CH(CHF_2)N_3$ or $CH(CH_2F)N_3$), or allyl.

In a particular embodiment the linker and blocking group are both present and are separate moieties which are both cleavable under substantially similar conditions. Thus deprotection and deblocking processes may be more efficient since only a single treatment will be required to remove both the dye compound and the blocking group.

The present disclosure also directs to encompassing polynucleotides incorporating dye compounds described herein. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, provided that at least one nucleotide labeled with a dye compound, according to the present application is present. Polynucleotides may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

ffC-I-1

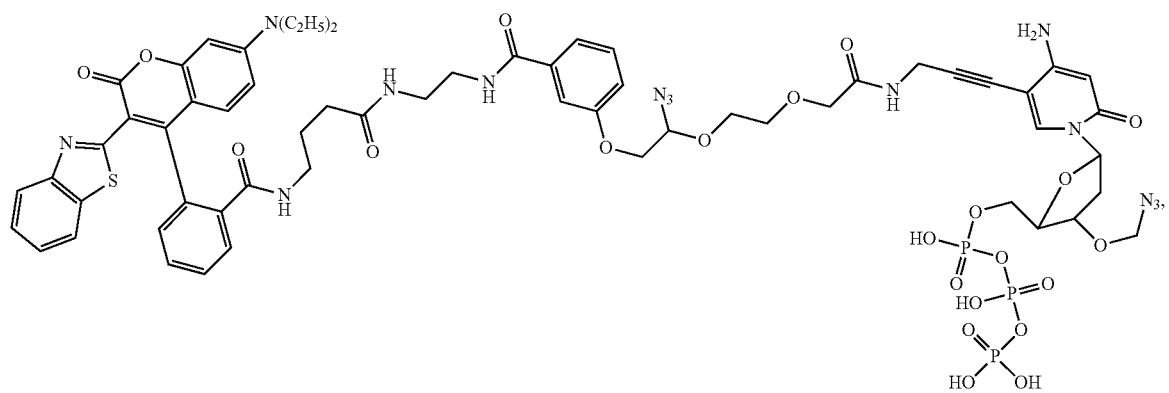

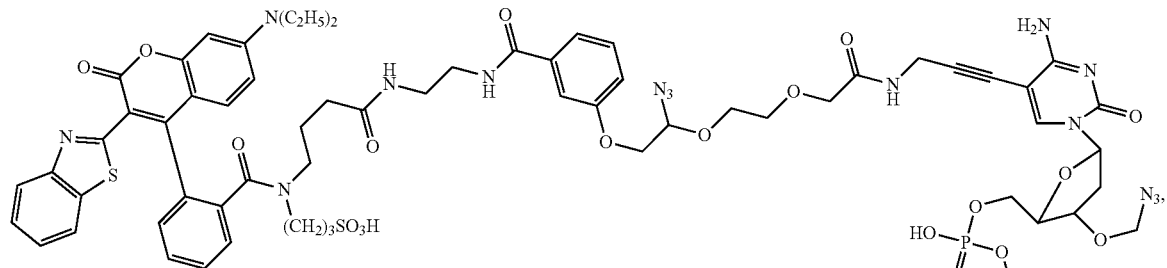

ffC-I-6

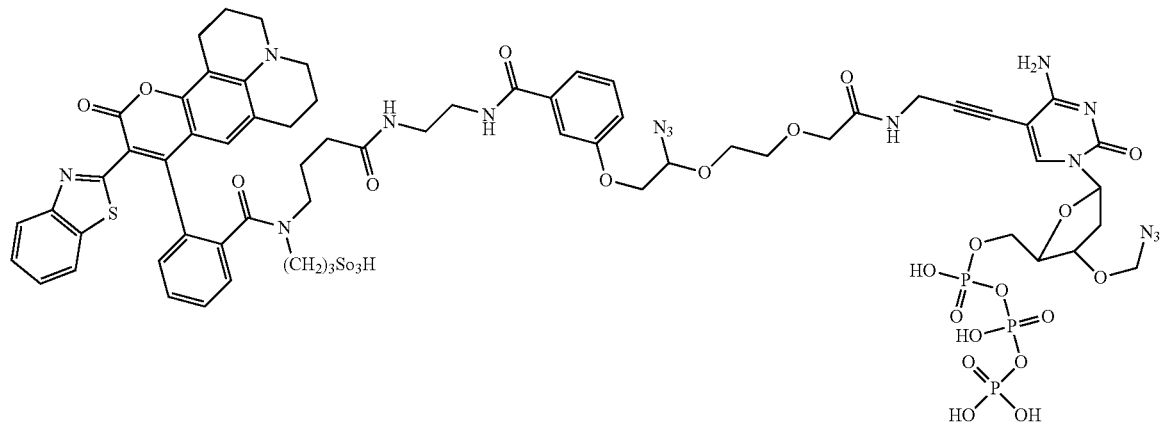

ffC-I-9

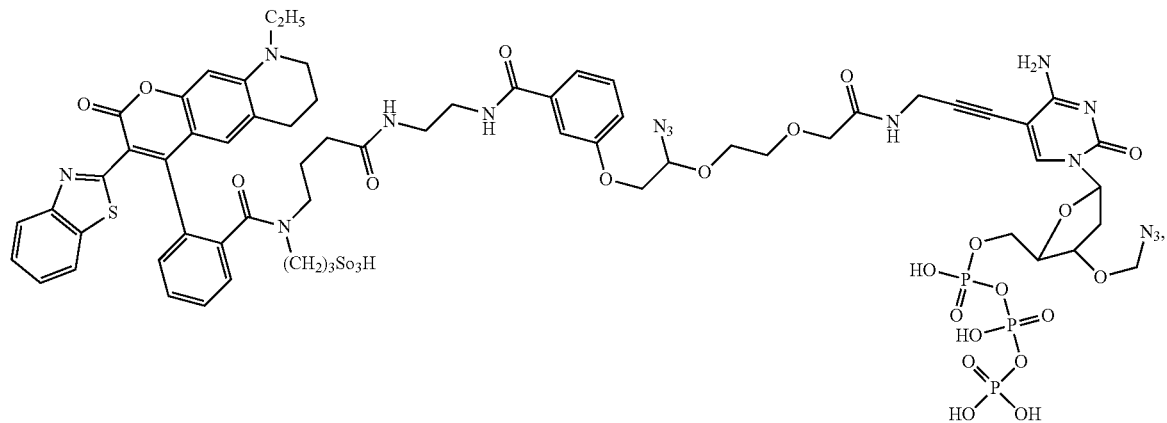

ffC-I-11 and

Kits

Some embodiments disclosed herein are kits including nucleosides and/or nucleotides labeled with the new fluorescent dyes described herein. Such kits will generally include at least one nucleotide or nucleoside labeled with a dye together with at least one further component. The further component(s) may be further modified or unmodified nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components or as nucleotide mixtures. In some embodiments, the kits comprise one or more nucleotides wherein at least one nucleotide is a nucleotide labeled with a new fluorescent compound described herein. The kits may comprise two or more labeled nucleotides. The nucleotides may be labeled with two or more fluorescent labels. Two or more of the labels may be excited using a single excitation source, which may be a laser.

The kits may contain four labeled nucleotides, where the first of four nucleotides is labeled with a compound as disclosed herein, and the second, third, and fourth nucleotides are each labeled with a different compound, wherein each compound has a distinct fluorescence maximum and each of the compounds is distinguishable from the other three compounds. The kits may be such that two or more of the compounds have a similar absorbance maximum but different Stokes shift.

The fluorescent dye compounds, labeled nucleotides or kits described herein may be used in sequencing, expression analysis, hybridization analysis, genetic analysis, RNA analysis or protein binding assays. The use may be on an automated sequencing instrument. The sequencing instrument may contain two lasers operating at different wavelengths.

Where kits comprise a plurality, particularly two, more particularly four, nucleotides labeled with a dye compound, the different nucleotides may be labeled with different dye compounds, or one may be dark, with no dye compounds. Where the different nucleotides are labeled with different dye compounds it is a feature of the kits that said dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary based DNA sequencing platform) when two or more such dyes are present in one sample. When two nucleotides labeled with fluorescent dye compounds are supplied in kit form, the spectrally distinguishable fluorescent dyes can be excited at the same wavelength, such as, for example by the same laser in some embodiments. When four nucleotides labeled with fluorescent dye compounds are supplied in kit form, two of the spectrally distinguishable fluorescent dyes can both be excited at one wavelength and the other two spectrally distinguishable dyes can both be excited at another wavelength in some embodiments. Particular excitation wavelengths are about 460 nm.

In one embodiment a kit comprises a nucleotide labeled with a compound described herein and a second nucleotide labeled with a second dye wherein the dyes have a difference in absorbance maximum of at least 10 nm, particularly 20 nm to 50 nm. More particularly the two dye compounds have Stokes shifts of between 15-40 nm or between 20-40 nm. As used herein, the term "Stokes shift" is the difference between positions of the band maxima of the absorption and emission spectra of the same electronic transition.

In a further embodiment said kit further comprises two other nucleotides labeled with fluorescent dyes wherein said dyes are excited by the same laser at about 460 nm to about 540 nm.

In an alternative embodiment, the kits may contain nucleotides where the same base is labeled with two different compounds. A first nucleotide may be labeled with a compound described herein. A second nucleotide may be labeled with a spectrally distinct compound, for example a 'red' dye absorbing at greater than 600 nm. A third nucleotide may be labeled as a mixture of the fluorescent dye compound described herein and the spectrally distinct compound, and the fourth nucleotide may be 'dark' and contain no label. In simple terms therefore the nucleotides 1-4 may be labeled 'green', 'red', 'red/green', and dark. To simplify the instrumentation further, four nucleotides can be labeled with a two dyes excited with a single laser, and thus the labeling of nucleotides 1-4 may be 'green 1', 'green 2' 'green 1/green 2', and dark.

In other embodiments the kits may include a polymerase enzyme capable of catalyzing incorporation of the nucleotides into a polynucleotide. Other components to be included in such kits may include buffers and the like. The nucleotides labeled with the new fluorescent dyes described herein, and other any nucleotide components including mixtures of different nucleotides, may be provided in the kit in a concentrated form to be diluted prior to use. In such embodiments a suitable dilution buffer may also be included.

Methods of Sequencing

Nucleotides (or nucleosides) comprising a new fluorescent dye described herein may be used in any method of analysis which requires detection of a fluorescent label attached to a nucleotide or nucleoside, whether on its own or incorporated into or associated with a larger molecular structure or conjugate. Some embodiments of the present application are directed to methods of sequencing including: (a) incorporating at least one labeled nucleotide as described herein into a polynucleotide; and (b) detecting the labeled nucleotide(s) incorporated into the polynucleotide by detecting the fluorescent signal from the new fluorescent dye attached to said modified nucleotide(s).

In some embodiments, at least one labeled nucleotide is incorporated into a polynucleotide in the synthetic step by the action of a polymerase enzyme. However, other methods of incorporating labeled nucleotides to polynucleotides, such as chemical oligonucleotide synthesis or ligation of labeled oligonucleotides to unlabeled oligonucleotides, are not excluded. Therefore, the term "incorporating" a nucleotide into a polynucleotide encompasses polynucleotide synthesis by chemical methods as well as enzymatic methods.

In all embodiments of the methods, the detection step may be carried out whilst the polynucleotide strand into which the labeled nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with modified nucleotide(s) as described herein in a synthetic step may be subsequently used as labeled probes or primers. In other embodiments the product of the synthetic step (a) may be subject to further reaction steps and, if desired, the product of these subsequent steps purified or isolated.

Suitable conditions for the synthetic step will be well known to those familiar with standard molecular biology techniques. In one embodiment the synthetic step may be analogous to a standard primer extension reaction using nucleotide precursors, including modified nucleotides according to the present disclosure, to form an extended target strand complementary to the template strand in the presence of a suitable polymerase enzyme. In other embodiments the synthetic step may itself form part of an amplification reaction producing a labeled double stranded amplification product comprised of annealed complementary strands derived from copying of the target and template polynucleotide strands. Other exemplary "synthetic" steps include nick translation, strand displacement polymerization, random primed DNA labeling etc. The polymerase enzyme used in the synthetic step must be capable of catalyzing the incorporation of modified nucleotides according to the present disclosure. Otherwise, the precise nature of the polymerase is not particularly limited but may depend upon the conditions of the synthetic reaction. By way of example, if the synthetic reaction is carried out using thermocycling then a thermostable polymerase is required, whereas this may not be essential for standard primer extension reactions. Suitable thermostable polymerases which are capable of incorporating the modified nucleotides according to the present disclosure include those described in WO 2005/024010 or WO 2006/120433. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the modified nucleotides or nucleosides labeled with the new fluorescent dyes with longer Stokes shift according to the present application may be used in a method of nucleic acid sequencing, re-sequencing, whole genome sequencing, single nucleotide polymorphism scoring, any other application involving the detection of the modified nucleotide or nucleoside when incorporated into a polynucleotide, or any other application requiring the use of polynucleotides labeled with the modified nucleotides comprising fluorescent dyes according to the present application.

In a particular embodiment the present application provides use of modified nucleotides comprising dye compounds described herein in a polynucleotide "sequencing-by-synthesis" reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) is determined in a detection or "imaging" step. The identity of the added base may be determined after each nucleotide incorporation step. The sequence of the template may then be inferred using conventional Watson-Crick base-pairing rules. The use of the modified nucleotides labeled with dyes according to the present disclosure for determination of the identity of a single base may be useful, for example, in the scoring of single nucleotide polymorphisms, and such single base extension reactions are within the scope of this application.

In an embodiment, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments each of the different nucleotide triphosphates (A, T, G and C) may be labeled with a unique fluorophore and also comprises a blocking group at the 3' position to prevent uncontrolled polymerization. Alternatively one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides are removed and the fluorescent signal from each incorporated nucleotide is "read" optically by suitable means, such as a charge-coupled device using laser excitation and suitable emission filters. The 3'-blocking group and fluorescent dye compounds are then removed (deprotected), particularly by the same chemical or enzymatic method, to expose the nascent chain for further nucleotide incorporation. Typically the identity of the incorporated nucleotide will be determined after each incorporation step but this is not strictly essential.

Similarly, U.S. Pat. No. 5,302,509 discloses a method to sequence polynucleotides immobilized on a solid support. The method relies on the incorporation of fluorescently labeled, 3'-blocked nucleotides A, G, C and T into a growing strand complementary to the immobilized polynucleotide, in the presence of DNA polymerase. The polymerase incorporates a base complementary to the target polynucleotide, but is prevented from further addition by the 3'-blocking group. The label of the incorporated nucleotide can then be determined and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO 2001/057248 and WO 2005/047301. Nucleotides are added successively to the free 3'-hydroxyl group, resulting in synthesis of a polynucleotide chain in the 5' to 3' direction. The nature of the base which has been added may be determined, particularly but not necessarily after each nucleotide addition, thus providing sequence information for the nucleic acid template. The term "incorporation" of a nucleotide into a nucleic acid strand (or polynucleotide) in this context refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to silica-based supports are those for example disclosed in PCT Publication No. WO 2000/006770, wherein polynucleotides are immobilized on a glass support by reaction between a pendant epoxide group on the glass with an internal amino group on the polynucleotide. In addition, PCT Publication No. WO2005/047301 discloses arrays of polynucleotides attached to a solid support, e.g. for use in the preparation of SMAs, by reaction of a sulfur-based nucleophile with the solid support. A still further example of solid-supported template polynucleotides is where the template polynucleotides are attached to hydrogel supported upon silica-based or other solid supports. Silica-based supports are typically used to support hydrogels and hydrogel arrays as described in PCT Publication Nos. WO 00/31148, WO 01/01143, WO02/12566, WO 03/014392, WO 00/53812 and U.S. Pat. No. 6,465,178.

A particular surface to which template polynucleotides may be immobilized is a polyacrylamide hydrogel. Polyacrylamide hydrogels are described in the prior art, some of which is discussed above. Specific hydrogels that may be used in the present application include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles for the purposes of sequencing; for example as described in U.S. Pat. No. 6,172,218. Further examples of the preparation of bead libraries where each bead contains different DNA sequences can be found in Margulies et al., Nature 437, 376-380 (2005); Shendure et al., Science. 309(5741):1728-1732 (2005). Sequencing of arrays of such beads using nucleotides as described is within the scope of the present application.

The template(s) to be sequenced may form part of an "array" on a solid support, in which case the array may take any convenient form. Thus, the method of the present disclosure is applicable to all types of "high density" arrays, including single-molecule arrays, clustered arrays and bead arrays. Modified nucleotides labeled with dye compounds of the present application may be used for sequencing templates on essentially any type of array formed by immobilization of nucleic acid molecules on a solid support, and more particularly any type of high-density array. However, the modified nucleotides labeled with the new fluorescent dyes described herein are particularly advantageous in the context of sequencing of clustered arrays.

In multi-polynucleotide or clustered arrays, distinct regions on the array comprise multiple polynucleotide template molecules. The term "clustered array" refers to an array wherein distinct regions or sites on the array comprise multiple polynucleotide molecules that are not individually resolvable by optical means. Depending on how the array is formed each site on the array may comprise multiple copies of one individual polynucleotide molecule or even multiple copies of a small number of different polynucleotide molecules (e.g. multiple copies of two complementary nucleic acid strands). Multi-polynucleotide or clustered arrays of nucleic acid molecules may be produced using techniques generally known in the art. By way of example, WO 98/44151 and WO 00/18957 both describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the modified nucleotides labeled with the new fluorescent dyes described herein.

The modified nucleotides labeled with dye compounds of the present application are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to effect individual resolution of the polynucleotides. The target nucleic acid molecules immobilized onto the surface of the solid support should thus be capable of being resolved by optical means. This means that, within the resolvable area of the particular imaging device used, there must be one or more distinct signals, each representing one polynucleotide.

This may be achieved wherein the spacing between adjacent polynucleotide molecules on the array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photo-bleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to PCT Publication Nos. WO 2000/006770 and WO 2001/057248. Although one application of the modified nucleotides of the present disclosure is in sequencing-by-synthesis reactions, the utility of such labeled nucleotides is not limited to such methods. In fact, the nucleotides may be used advantageously in any sequencing methodology which requires detection of fluorescent labels attached to nucleotides incorporated into a polynucleotide.

In particular, the modified nucleotides labeled with dye compounds of the present application may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So called Sanger sequencing methods, and related protocols (Sanger-type), rely upon randomized chain termination with labeled dideoxynucleotides.

Thus, the present disclosure also encompasses modified nucleotides labeled with dye compounds as described herein which are dideoxynucleotides lacking hydroxyl groups at both of the 3' and 2' positions, such modified dideoxynucleotides being suitable for use in Sanger type sequencing methods and the like.

Methods of Preparation

Some additional embodiments described herein are related to a method of preparing a compound of Formula (Ia), the methods include reacting a compound of Formula (IIa)

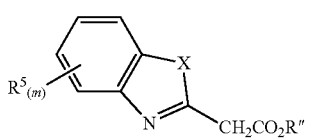
(IIa)

or Formula (IIb)

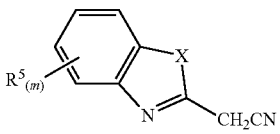
(IIb)

with a compound of Formula (III)

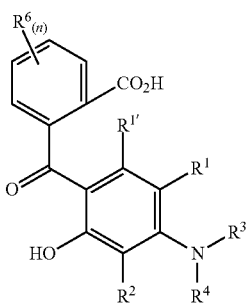
(III)

to form

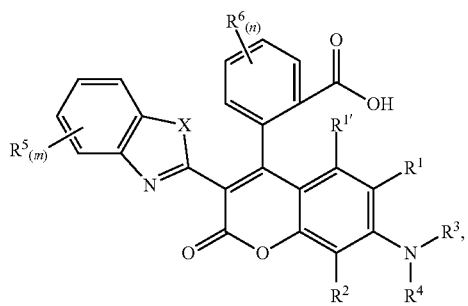
(Ia)

where the variables $R^1$, $R^{1'}$, $R^2$, $R^3$, $R^4$, $R^5$, $R^6$, X, m and n are defined above in the disclosure of compounds of Formula (I), and R'' is selected from the group consisting of H, optionally substituted alkyl, alkenyl, alkynyl, aminoalkyl, haloalkyl, heteroalkyl, alkoxyalkyl, sulfo, optionally substituted aryl; optionally substituted heteroaryl, optionally substituted carbocyclyl, and optionally substituted heterocyclyl.

Some additional embodiments described herein are related to a method of preparing a compound of Formula (Ia'), the methods include reacting a compound of Formula (IIa)

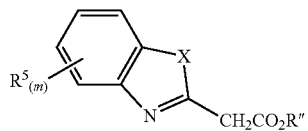
(IIa)

or Formula (IIb)

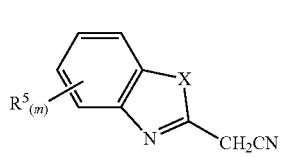
(IIb)

with a compound of Formula (IIIa)

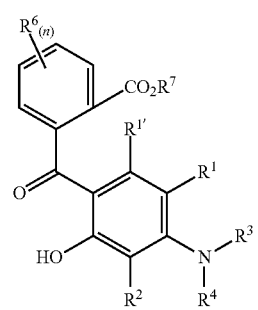
(IIIa)

to form

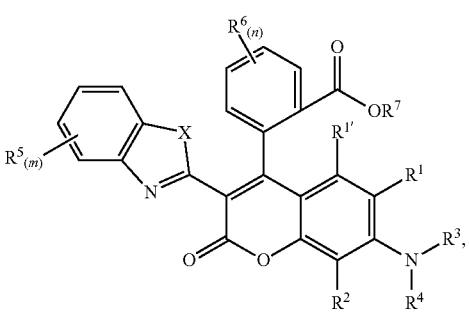
(Ia')

where the variables $R^1$, $R^{1'}$, $R^2$, $R^3$, $R^4$, $R^5$, $R^6$, $R^7$, R'', X, m and n are defined above.

Some additional embodiments described herein are related to a method of preparing a compound of Formula (Ia'), the method includes converting a compound of Formula (Ia) to a compound of Formula (Ia') through carboxylic acid activation:

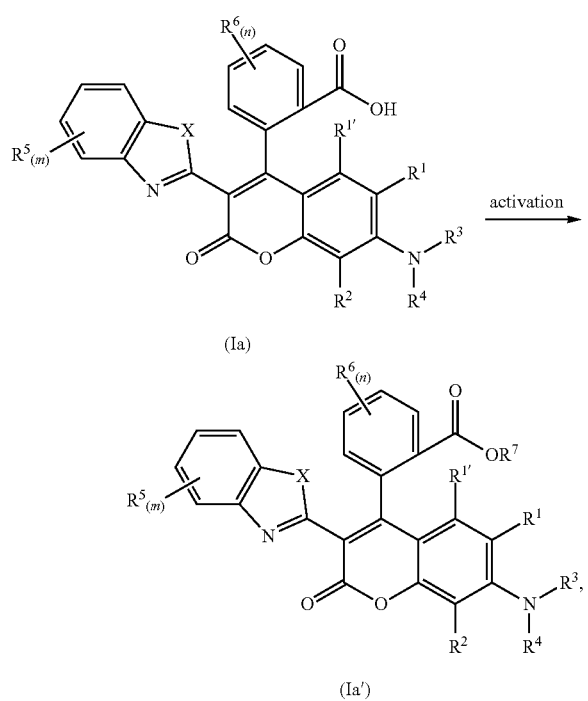

(Ia)

(Ia')

where the variables $R^1$, $R^{1'}$, $R^2$, $R^3$, $R^4$, $R^5$, $R^6$, $R^7$, $R^8$, $R^9$, X, m and n are defined above in the disclosure of compounds of Formula (I).

Some additional embodiments described herein are related to a method of preparing a compound of Formula (Ib), the method includes converting a compound of Formula (Ia) to a compound of Formula (Ia') through carboxylic acid activation:

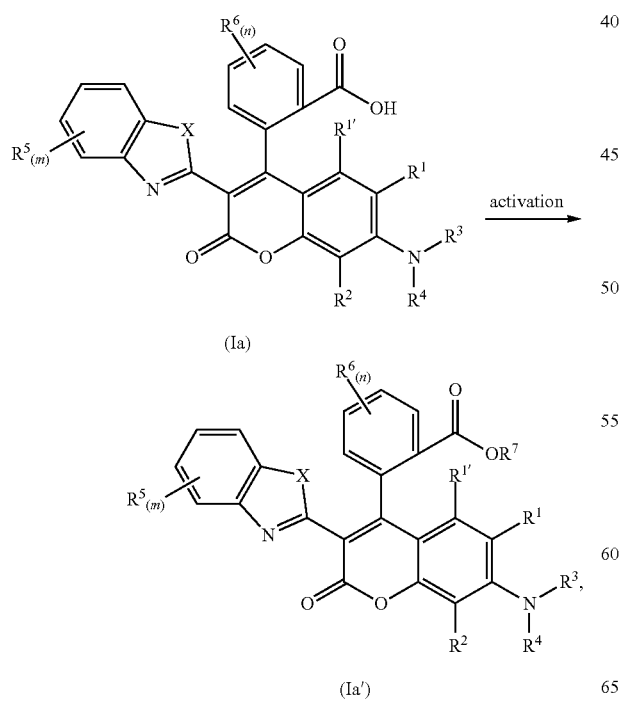

(Ia)

(Ia')

and reacting the compound of Formula (Ia') with a primary or secondary amine of Formula (IV),

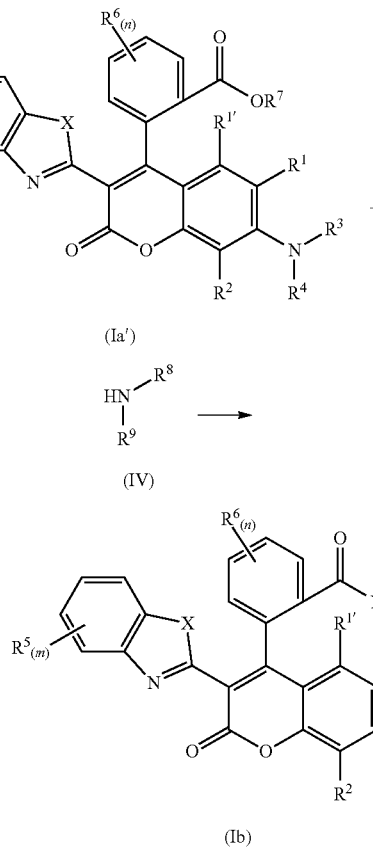

(Ia')

(IV)

(Ib)

where the variables $R^1$, $R^{1'}$, $R^2$, $R^3$, $R^4$, $R^5$, $R^6$, $R^7$, $R^8$, $R^9$, X, m and n are defined above in the disclosure of compounds of Formula (I).

Some additional embodiments described herein are related to a method of preparing a compound of Formula (Ib), the methods include reacting a compound of Formula (IIa)

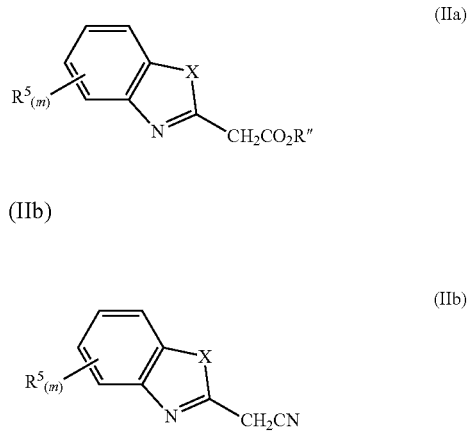

(IIa)

or Formula (IIb)

(IIb)

with a compound of Formula (IIIb)

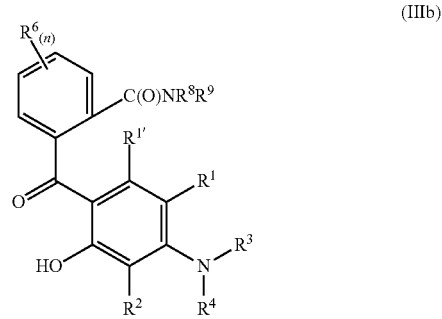

to form

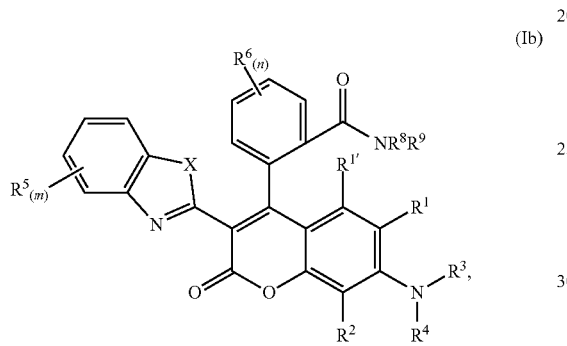

where the variables $R^1$, $R^{1'}$, $R^2$, $R^3$, $R^4$, $R^5$, $R^6$, $R^7$, $R''$, X, m and n are defined above.

The preparation of compounds of Formula (Ia) can be accomplished by reacting starting materials of Formula (IIa) or (IIb) with the intermediate compound of Formula (III) preferably in one to one molar ratio in organic solvent with or without a catalyst. Both organic catalysts (for example, trifluoroacetic acid or methanesulfonic acid) and inorganic catalysts (for example, phosphoric or sulfuric acid) may be used. In some embodiments the preparation may be fulfilled without a solvent or using a catalyst as solvent.

The preparation of compounds of Formula (Ia') or (Ib) can be accomplished by first acid activation of starting materials of Formula (Ia) in organic solvent at room temperature using, for example, carbodiimide, O-(benzotriazol-1-yl)-N,N,N',N'-tetramethyluronium salts, BOP or PyBOP as an activation reagent, followed by reaction with appropriate hydroxy derivatives $HOR^7$ or amine of formula (IV) for the coupling step.

Compounds of Formula (V), (Va) or (Vb) may be prepared following similar synthetic schemes as described above in the preparation of compounds of Formula (Ia), (Ia') or (Ib).

Compounds of Formula (I) may be used in some organic reactions, for example in electrophilic aromatic substitution reactions as starting materials for new dyes synthesis. For example, it was demonstrated previously by Alan S. Waggoner (*Bioconjugate Chemistry*, 1993, 4(2):105-111; see also U.S. Pat. Pub. No. 2015/0274976) that some cyanine dyes molecules modifications by sulfonation reaction may improve fluorescent properties such derivatives.

Sulfonation of compounds (I) can be fulfilled by reaction with sulfur trioxide, with sulfur trioxide derivatives or solutions, for example in sulfuric acid

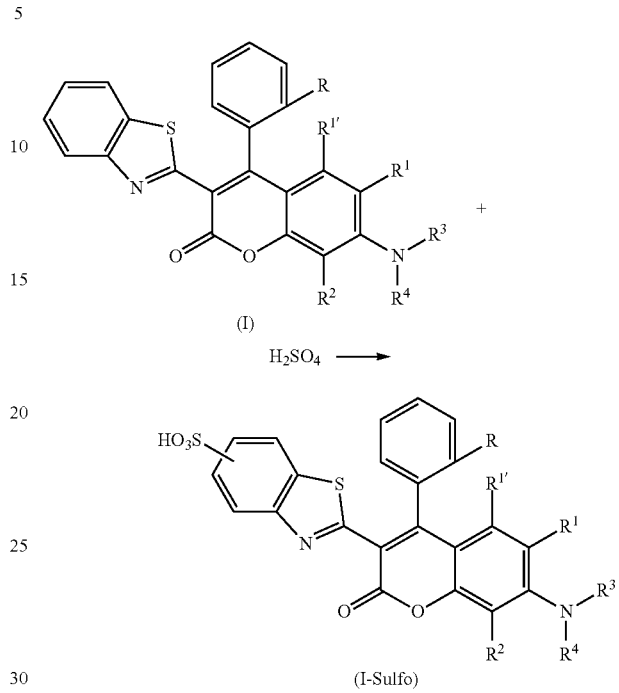

Sulfochlorination of compounds (I) can be fulfilled by reaction with chlorosulfonic acid.

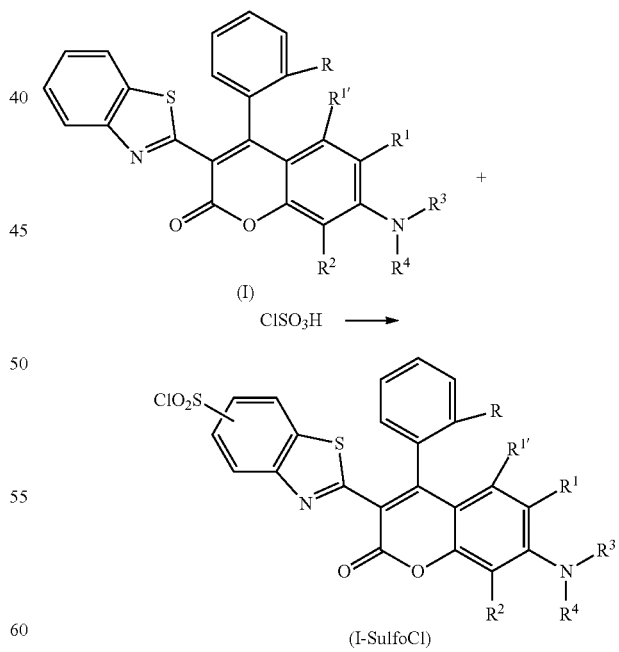

Compounds of Formula (I) containing sulfonic- or chlorosulfonic groups can be further modified, for example, by reacting with ammonia, primary- or secondary amines formula (IV):

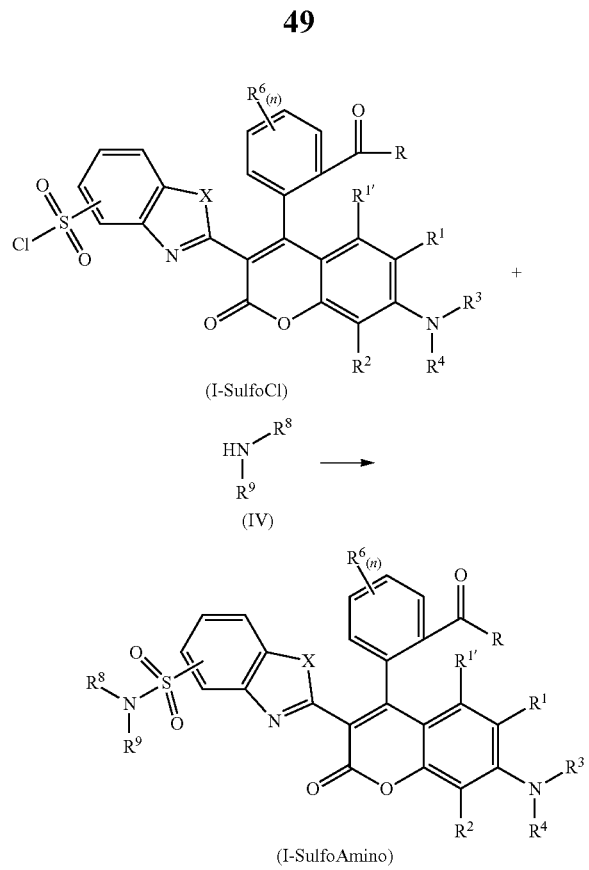

(I-SulfoCl)

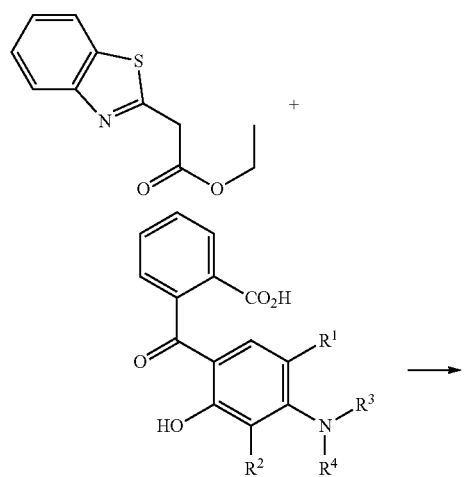

(I-SulfoAmino)

where the variables $R^1$, $R^{1'}$, $R^2$, $R^3$, $R^4$, $R^5$, $R^6$, $R^7$, $R^8$, $R^9$, X, n are defined above in the disclosure of compounds of Formula (I).

EXAMPLES

Additional embodiments are disclosed in further detail in the following examples, which are not in any way intended to limit the scope of the claims.

General Procedure for the Synthesis of Compounds of Formula (Ia)

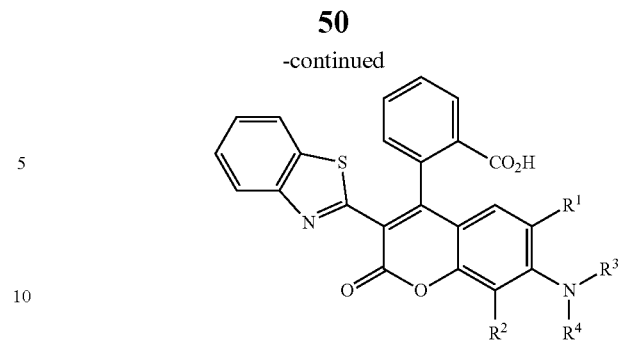

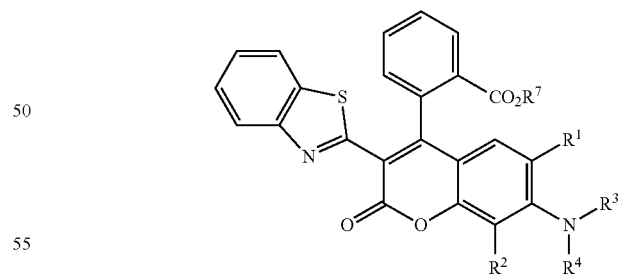

Mixture of ethyl benzothiazolyl-2 acetic acid (2.2 g, 0.01 mol) and an appropriate derivative of hydroxy benzoyl benzoic acid (0.011 mol) was dissolved in concentrated sulfuric acid (5 mL). This reaction mixture was stirred at room temperature for 1 hour and then heated, for example, at 80-120° C. for 1-2 hours till the reaction was completed. The reaction mixture was poured into ice (about 50 g) and the product was filtered, washed with water. In many cases, the final products do not need any further purification.

General Procedure for the Synthesis of Compounds of Formula (Ia')

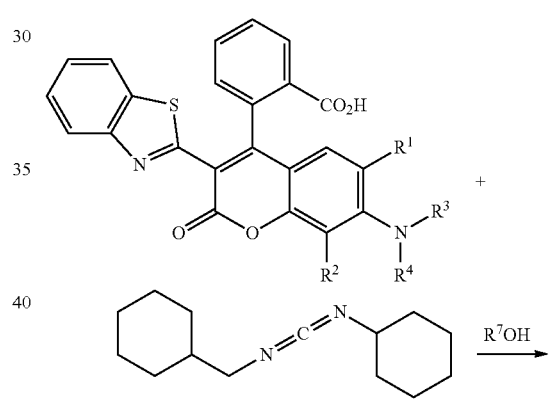

A compound of Formula (Ia) (0.001 mol) was dissolved in anhydrous DMF (1.5 mL). To this solution carbodiimide (0.0012 mol) or another activation reagent was added. This reaction mixture was stirred at room temperature for 3 hour and then appropriate hydroxy derivatives $R^7OH$ was added. The reaction mixture was stirred overnight then filtered and poured into ice (about 50 g). The product was filtered off, washed with water. Yield: 55-75%. In many cases, the final products do not need any further purification.

General Procedure for the Synthesis of Compounds of Formula (Ib)

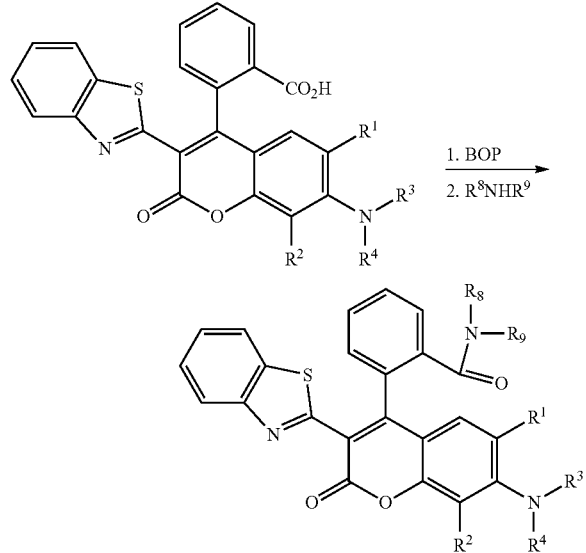

A compound of Formula (Ia) (0.001 mol) was dissolved in suitable anhydrous organic solvent (DMF, 1.5 mL). To this solution TSTU, BOP or PyBOP as activation reagent was added. This reaction mixture was stirred at room temperature for about 20 min and then appropriate amine NHR$^8$R$^9$ was added. The reaction mixture was stirred overnight, filtered and excess of the activation reagent was quenched with 0.1M TEAB solution in water. Solvents were evaporated in vacuum and the residue was purified by HPLC. Yield: 65-75%.

Example 1

2-[3-(Benzothiazol-2-yl)-9-ethyl-2-oxo-6,7,8,9-tetra-hydro-2H-pyrano[3,2-g]quinolin-4-yl]benzoic acid (Compound I-3)

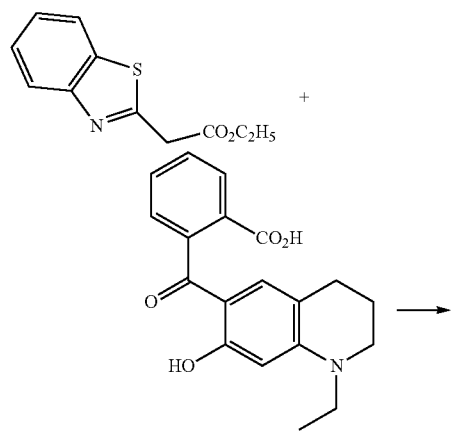

Sulfuric acid (2 mL) was placed into a round-bottomed flask then cooled down to about 0-5° C. and 0.325 g (1.0 mmol, 1 eq) of 2-(1-ethyl-7-hydroxy-1,2,3,4-tetrahydroquinoline-6-carbonyl)benzoic acid was added with stirring following by addition of 0.3 g (1.4 mmol, 1.4 eq) ethyl 2-(benzothiazol-2-yl)acetate. This reaction mixture was stirred at room temperature (about 20° C.) for 30 min then heated for 1.5 hours while stirring at 100° C. Reaction progress was monitored by TLC (DCM-MeOH, 10%) and by LCMS.

Reaction mixture was left at room temperature (about 20° C.) for 0.5 hour and then was poured into mixture of crushed ice (about 100 g) and sodium acetate (about 5 g). After 1 hour the product was filtered off and washed with water until neutral, then the filtrate was air dried. Yield: 0.35 g (0.73 mmol, 73%). The final product was used without further purification. MS (DUIS): MW Calculated 482.13. Found: (−) 481 (M−1), (+) 483 (M+1). $^1$H NMR (400 MHz, DMSO-d$_6$) δ 12.71 (s, 1H), 8.11-8.02 (m, 1H), 7.96 (dd, J=7.4, 1.6 Hz, 1H), 7.56 (tt, J=7.5, 5.8 Hz, 2H), 7.40 (d, J=7.2 Hz, 1H), 7.39-7.25 (m, 2H), 7.16 (dd, J=6.6, 2.1 Hz, 1H), 6.67 (s, 1H), 6.35 (s, 1H), 3.48 (q, J=7.0 Hz, 2H), 3.36 (t, J=5.7 Hz, 2H), 2.65-2.55 (m, 2H), 1.79 (q, J=6.3 Hz, 2H), 1.15 (t, J=7.0 Hz, 3H).

Example 2

2-[10-(Benzothiazol-2-yl)-1,1,7,7-tetramethyl-11-oxo-2,3,6,7-tetrahydro-1H,5H,11H-pyrano[2,3-f]pyrido[3,2,1-ij]quinolin-9-yl]benzoic acid (Compound I-5)

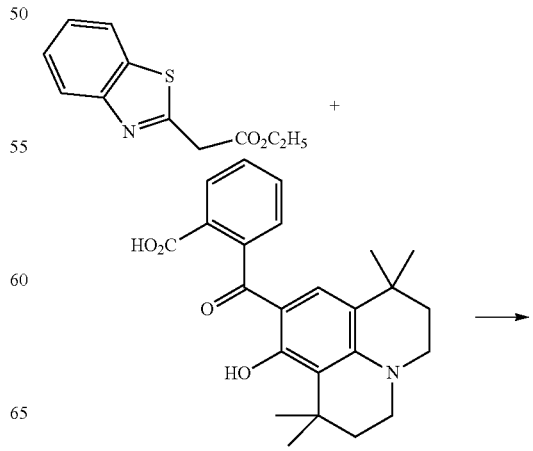

-continued

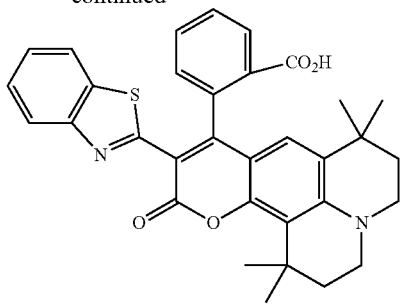

Mixture of 0.75 g (1.90 mmol, 1 eq) of 2-(8-hydroxy-1,1,7,7-tetramethyl-2,3,6,7-tetrahydro-1H,5H-pyrido[3,2,1-ij]quinoline-9-carbonyl)benzoic acid and 0.44 g (1.99 mmol, 1.04 eq) ethyl 2-(benzothiazol-2-yl)acetate was added with stirring to concentrated sulfuric acid (7 mL) at room temperature (about 20° C.). This reaction mixture was stirred at room temperature for 30 min then heated 2.5 hours while stirring at 120° C. Reaction progress was monitored by TLC (DCM-MeOH, 10%) and by LCMS. Reaction mixture was left at room temperature (about 20° C.) for 0.5 hour and then was poured into mixture of crushed ice (about 50 g) and sodium acetate (about 5 g). After 1 hour the product was filtered off and washed with water until neutral and air dried. Yield: 0.58 g (1.05 mmol, 55%). The final product was used without further purification. MS (DUIS): MW Calculated 550.19. Found: (−) 549 (M−1).

Example 3

2-[3-(Benzothiazol-2-yl)-7-(ethylamino)-6-methyl-2-oxo-2H-chromen-4-yl]benzoic acid (Compound I-8)

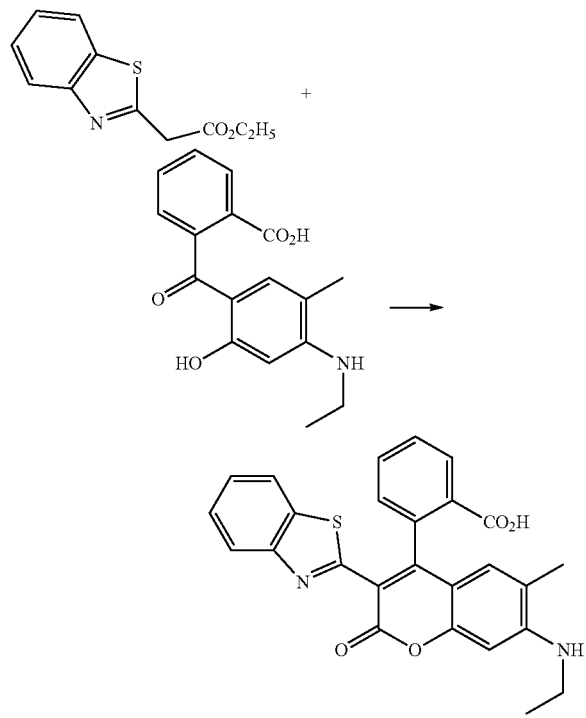

Sulfuric acid (5 mL) was placed into a round-bottomed flask then cooled doom to about 0-5° C. and 0.7 g (2.34 mmol, 1 eq) of 2-(4-(ethylamino)-2-hydroxy-5-methylbenzoyl)benzoic acid was added with stirring following by addition of 0.7 g (3.16 mmol, 1.35 eq) ethyl 2-(benzothiazol-2-yl)acetate. This reaction mixture was stirred for 30 min at room temperature (about 20° C.) then heated for 1 hour while stirring at 95° C. Reaction progress was monitored by TLC (DCM-MeOH, 10%) and by LCMS.

The reaction mixture was left at room temperature (about 20° C.) for 0.5 hour and then was poured into mixture of crushed ice (about 100 g) and sodium acetate (about 5 g). After 1 hour the product was filtered off and washed with water until neutral and air dried. Yield: 1.01 g (2.22 mmol, 95%). The final product was used without further purification. MS (DUIS): MW Calculated 456.11. Found: (−) 455 (M−1), (+) 457 (M+1). $^1$H NMR (400 MHz, Methanol-$d_4$) δ 8.19-8.12 (m, 1H), 7.92-7.78 (m, 1H), 7.64 (dd, J=8.3, 1.1 Hz, 1H), 7.61-7.48 (m, 2H), 7.43-7.36 (m, 1H), 7.36-7.26 (m, 1H), 7.21-7.14 (m, 1H), 6.60 (s, 1H), 6.56 (d, J=1.1 Hz, 1H), 3.41-3.34 (m, 2H), 2.03 (s, 3H), 1.38-1.27 (m, 3H).

Example 4-1

2-[10-(Benzothiazol-2-yl)-11-imino-2,3,6,7-tetrahydro-1H,5H,11H-pyrano[2,3-f]pyrido[3,2,1-ij]quinolin-9-yl]benzoic acid (Compound I-4A)

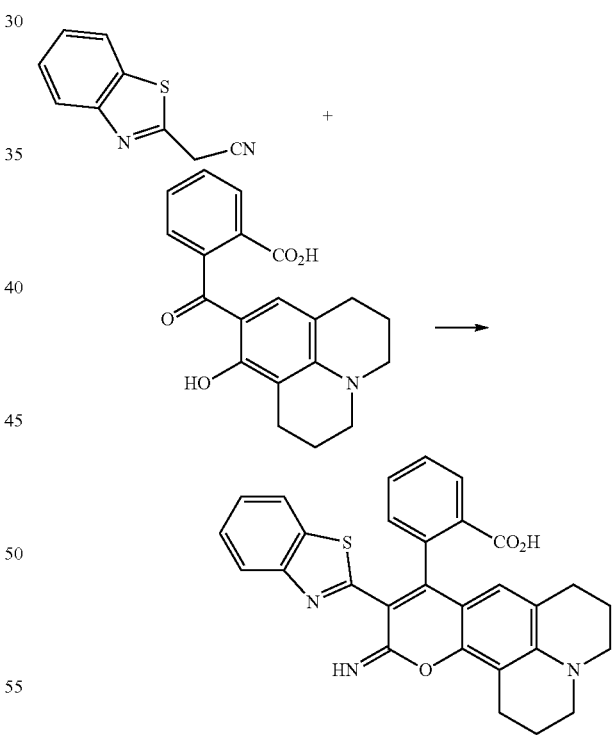

Sulfuric acid (10 mL) was placed into a round-bottomed flask then 1 g (2.96 mmol, 1 eq) of 2-(8-hydroxy-2,3,6,7-tetrahydro-1H,5H-pyrido[3,2,1-ij]quinoline-9-carbonyl) benzoic acid was added with stirring following by addition of 0.57 g (3.26 mmol, 1.1 eq) 2-(benzothiazol-2-yl)acetonitrile. This reaction mixture was stirred at room temperature (about 20° C.) for 30 min then heated for 1.5 hours while stirring at 80° C. and 1 h at 90° C. Reaction progress was monitored by TLC (DCM-MeOH, 10%) and by LCMS.

Reaction mixture was left at room temperature (about 20° C.) for 0.5 hour and then was poured into mixture of crushed ice (about 100 g). After 0.5 hour the product was filtered off and washed with water until neutral and air dried. Yield: 0.8 g (1.62 mmol, 55%). The final product was used without further purification. MS (DUIS): MW Calculated 493.15. Found: (−) 492 (M−1), (+) 494 (M+1).

Example 4-2

2-[10-(Benzothiazol-2-yl)-11-oxo-2,3,6,7-tetra-hydro-1H,5H,11H-pyrano[2,3-f]pyrido[3,2,1-ij]qui-nolin-9-yl]benzoic acid (Compound I-4)

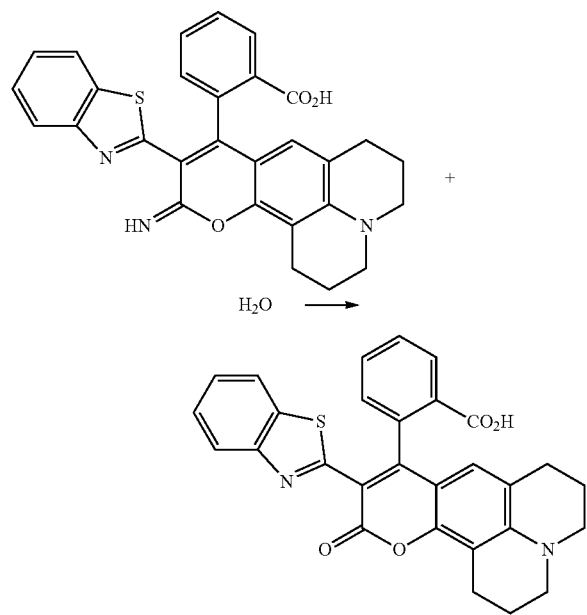

Suspension of the imine (I-4A) from previous step (example 4-1) and water (25 ml) was stirred 5 h at 80° C. At the end of this time red color of starting material almost gone and very strong fluorescence developed. Reaction progress was monitored by TLC (DCM-MeOH, 10%) and by LCMS. The reaction mixture was left at room temperature (about 20° C.) for 0.5 hour and then the product was filtered off and washed with water and air dried. Yield: 0.77 g (1.56 mmol, 96%). The final product was used without further purification. MS (DUIS): MW Calculated 494.13. Found: (−) 493 (M−1), (+) 495 (M+1).

Example 5

2-[10-(Benzothiazol-2-yl)-11-oxo-2,3,6,7-tetra-hydro-1H,5H,11H-pyrano[2,3-f]pyrido[3,2,1-ij]qui-nolin-9-yl]benzoic acid (Compound I-4)

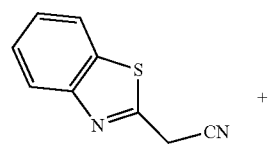

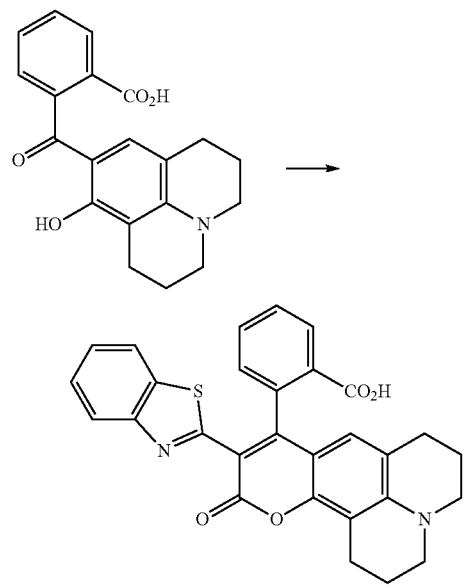

Sulfuric acid (10 mL) was placed into a round-bottomed flask then 1 g (2.96 mmol, 1 eq) of 2-(8-hydroxy-2,3,6,7-tetrahydro-1H,5H-pyrido[3,2,1-ij]quinoline-9-carbonyl) benzoic acid was added with stirring following by addition of 0.57 g (3.26 mmol, 1.1 eq) 2-cyanomethylbenzothiazole. This reaction mixture was stirred at room temperature (about 20° C.) for 30 min then heated for 2 hours while stirring at 95° C. Reaction mixture was left to cool down to room temperature (about 20° C.) and then was poured into mixture of water and crushed ice (about 75 g). This mixture was stirred overnight at room temperature and the product was filtered off and washed with water until neutral and air dried. The final product was used without further purification. Yield: 1.09 g (2.21 mmol, 75%). MS (DUIS): MW Calculated 494.13. Found: (−) 493 (M−1), (+) 495 (M+1).

Example 6

2-[3-(benzothiazol-2-yl)-7-(dimethylamino)-2-oxo-2H-chromen-4-yl]benzoic acid (Compound I-2)

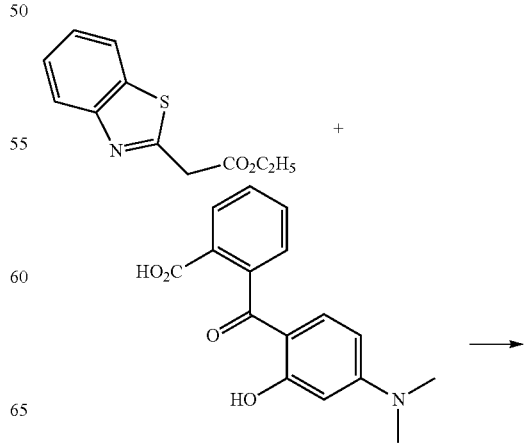

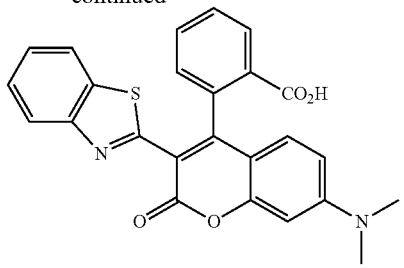

Mixture of 0.285 g (1.0 mmol, 1 eq) of 2-[4-(dimethylamino)-2-hydroxybenzoyl]benzoic acid and 0.243 g (1.1 mmol, 1.1 eq) ethyl 2-(benzothiazol-2-yl)acetate was added with stirring to sulfuric acid (5 mL) at room temperature (about 20° C.). This reaction mixture was stirred at room temperature for 3 hours then heated for 4 hours while stirring at 100° C. Reaction progress was monitored by TLC (DCM-MeOH, 10%) and by LCMS. Reaction mixture was left at room temperature (about 20° C.) overnight and then was poured into mixture of water-crushed ice (about 100 g) and sodium acetate (about 5 g). After 1 hour the product was filtered off and washed with water until neutral and air dried. Yield: 0.429 g (0.96 mmol, 97%). The final product was used without further purification. MS (DUIS): MW Calculated 442.10. Found: (−) 441 (M−1). $^1$H NMR (400 MHz, DMSO-d$_6$) δ 12.70 (s, 1H), 8.14-8.04 (m, 1H), 8.04-7.94 (m, 1H), 7.58 (h, J=6.5 Hz, 2H), 7.43 (d, J=7.8 Hz, 1H), 7.40-7.29 (m, 2H), 7.19 (dd, J=7.2, 1.7 Hz, 1H), 6.78-6.63 (m, 3H), 3.07 (s, 6H).

Example 7-1

2-[3-(Benzothiazol-2-yl)-7-(diethylamino)-2-oxo-2H-chromen-4-yl]benzoic acid (Compound I-1)

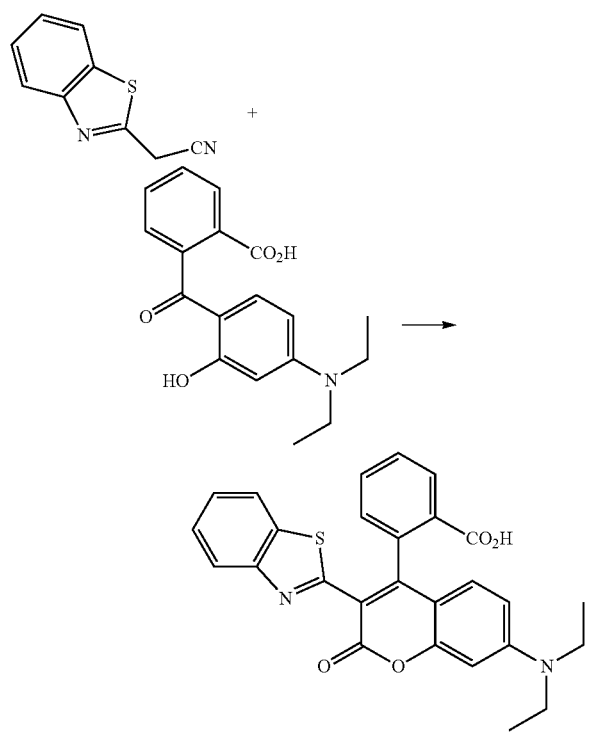

Sulfuric acid (8 mL) was placed into a round-bottomed flask then 0.25 g (0.8 mmol, 1 eq) 2-[4-(diethylamino)-2-hydroxybenzoyl]benzoic acid was added with stirring following by addition of 0.14 g (0.8 mmol, 1 eq) 2-cyanomethylbenzothiazole. The reaction mixture was stirred at room temperature (about 20° C.) for 30 min then heated for 2 hours while stirring at 95° C. This reaction mixture was poured into ice-cold water (about 75 g). At this stage, the corresponding imine intermediate (I-1A) was formed and it may be isolated by filtration. In water or in organic solvents with presence of water and particularly in acid condition the further hydrolysis of the imine intermediate may be achieved.

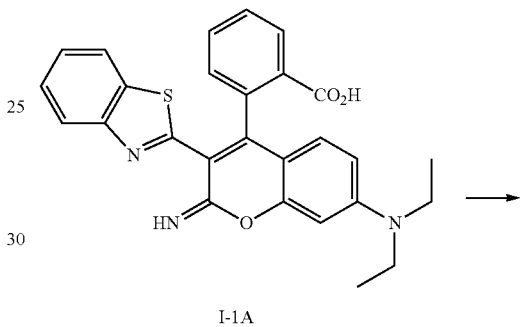

I-1A

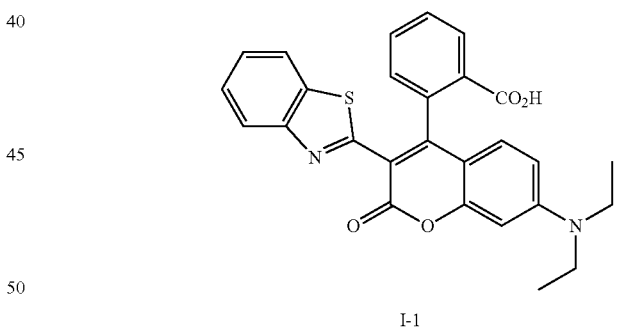

I-1

This mixture was stirred overnight at room temperature and the product was filtered off and washed with water until neutral and air dried. Yield: 0.33 g (0.7 mmol, 88%). The final product was used without further purification. MS (DUIS): MW Calculated 470.13. Found: (−) 469 (M−1), (+) 471 (M+1). $^1$H NMR (400 MHz, DMSO-d$_6$) δ 12.71 (s, 1H), 8.08 (dt, J=7.6, 1.7 Hz, 1H), 8.03-7.92 (m, 1H), 7.64-7.52 (m, 2H), 7.45-7.39 (m, 1H), 7.39-7.27 (m, 2H), 7.19 (dd, J=6.9, 2.3 Hz, 1H), 6.70 (d, J=1.9 Hz, 1H), 6.69-6.61 (m, 2H), 3.47 (q, J=7.2 Hz, 4H), 1.23-1.05 (m, 6H).

Example 7-2

2-(7-(Diethylamino)-2-oxo-3-(6-sulfobenzothiazol-2-yl)-2H-chromen-4-yl)benzoic acid (Compound I-13)

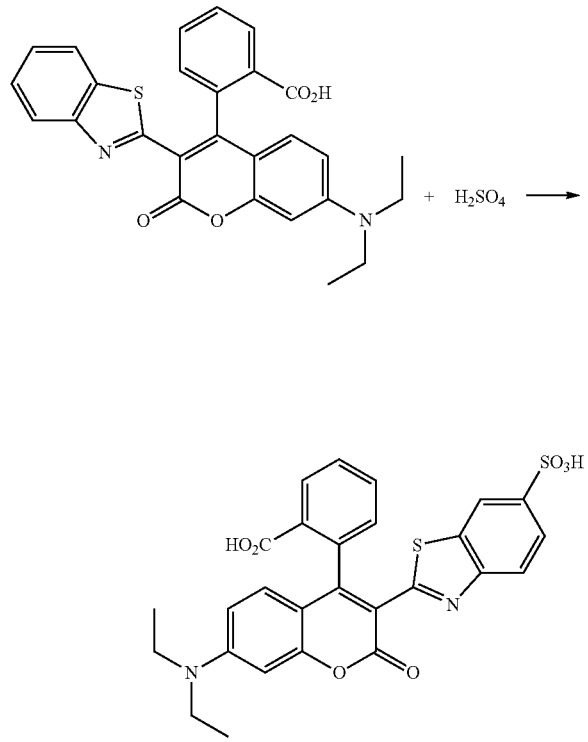

2-[3-(Benzothiazol-2-yl)-7-(diethylamino)-2-oxo-2H-chromen-4-yl]benzoic acid (Compound I-1) (1.3 g, 2.76 mmol) was placed into a round-bottomed flask, dried in high vacuum, then cooled down in acetone-dry ice bath. Fuming sulfuric acid (20%, 5.8 mL, 27 mmol) was added dropwise while stirring. This reaction mixture was stirred at room temperature for 1 hour then heated for 1 hour at 50° C. and starting material was dissolved. The reaction mixture was chilled down and anhydrous ether was added with precaution. Off-white hydroscopic precipitate was filtered off and the filtrate was triturated with ether again and then with EtOH. Pink precipitate was collected. Yield 1.21 g (80%). The final product was used without further purification. MS (DUIS): MW Calculated 550.09. Found: (−) 549 (M−1), (+) 551 (M+1). $^1$H NMR (400 MHz, TFA) δ 8.85-8.78 (m, 1H), 8.69 (s, 1H), 8.57-8.45 (m, 2H), 8.26-8.15 (m, 2H), 7.94 (s, 1H), 7.67 (d, J=9.4 Hz, 1H), 7.63-7.56 (m, 1H), 7.45 (dd, J=8.8, 4.5 Hz, 1H), 3.94 (q, J=7.2 Hz, 4H), 1.38 (t, J=7.1 Hz, 6H). In according with HPLC and NMR spectra analysis this product consists mainly from one isomer.

Example 7-3

2-(7-(Diethylamino)-2-oxo-3-(6-chlorosulfonylbenzothiazol-2-yl)-2H-chromen-4-yl)benzoic acid (Compound I-14)

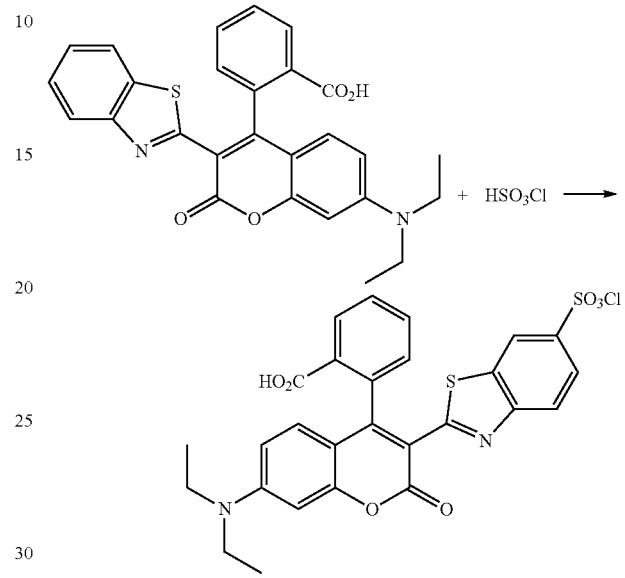

Chlorosulfonic acid (5 ml, 75 mmol) was cooled in an ice bath and dye I-1 (1.2 g, 2.55 mmol) was carefully added with stirring portion-wise over a period of 5 minutes. The combined mixture was stirred at room temperature (~20° C.) for 1.5 hours and then heated at 95-100° C. for 6 hours. After cooling to room temperature, the mixture was added very slowly to ca. 20 ml ice/water mixture. A red colored solid separated which was quickly filtered off and was washed with cold water (2×30 ml) and dried in vacuum. Yield 1.2 g (83%, 2.11 mmol). This compound was used in next step without additional purification.

Example 7-4

2-(7-(Diethylamino)-2-oxo-3-(6-aminosulfonylbenzothiazol-2-yl)-2H-chromen-4-yl)benzoic acid (Compound I-15)

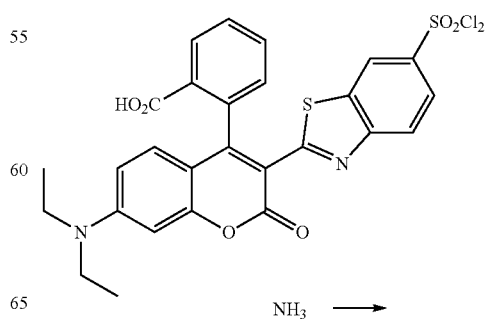

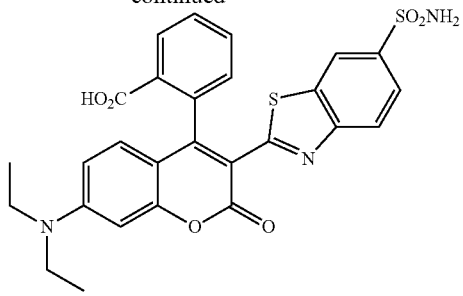

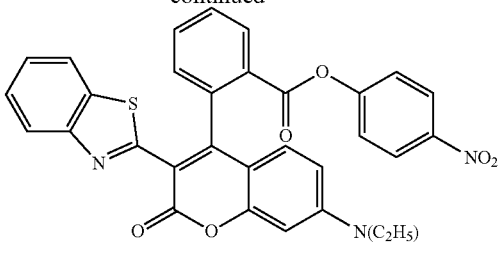

I-1B 2-(7-(Diethylamino)-2-oxo-3-(6-chlorosulfonylbenzothiazol-2-yl)-2H-chromen-4-yl) benzoic acid (I-14) (1.2 g, 2.11 mmol) was carefully added portion-wise with stirring to ammonia solution (5 ml, 25%) cooled in an ice bath over a period of 5 minutes. The reaction mixture was stirred at room temperature (~20° C.) for 1 hour and solvent was distilled off at room temperature in vacuum. Compound was purified by flash column (silica gel, DCM-MeOH as eluent). Yield 0.34 g (30%, 0.62 mmol). This compound contain small amount of other isomers and was used in next step without additional purification. MS (DUIS): MW Calculated 549.10. Found: (−) 548 (M−1), (+) 550 (M+1). $^1$H NMR (400 MHz, TFA) δ 8.83-8.73 (m, 1H), 8.62 (d, J=1.6 Hz, 1H), 8.57 (d, J=8.9 Hz, 1H), 8.42 (dd, J=8.9, 1.8 Hz, 1H), 8.24-8.13 (m, 2H), 7.82 (d, J=2.1 Hz, 1H), 7.64-7.52 (m, 2H), 7.38 (d, J=8.8 Hz, 1H), 3.90 (q, J=7.2 Hz, 4H), 1.37 (t, J=7.2 Hz, 6H).

Example 8

4-Nitrophenyl 2-[3-(benzothiazol-2-yl)-7-(diethylamino)-2-oxo-2H-chromen-4-yl]benzoate (Compound I-1B)

In anhydrous DMF (1.5 mL) 94 mg (0.2 mmol, 1 eq) of 2-[3-(benzothiazol-2-yl)-7-(diethylamino)-2-oxo-2H-chromen-4-yl]benzoic acid (I-1, NR440) was dissolved. To this solution dicyclohexylcarbodiimide (62 mg, 0.3 mmol, 1.5 eq) was added. This reaction mixture was stirred at room temperature for 3 hour and then p-nitrophenol (33 mg, 0.24 mmol, 1.2 eq) was added. The reaction mixture was stirred overnight then dicyclohexyl urea was filtered off. Solvent was distilled off in vacuum at room temperature and the oily residue was poured into ice (about 5 g). The solid yellow product was filtered off, washed with water. Yield: 79 mg (67%, 0.134 mmol). MS (DUIS): MW Calculated 591.15. Found: (−) 590 (M−1), (+) 592 (M+1).

Example 9

Triethylammonio 3-(2-(10-(benzothiazol-2-yl)-11-oxo-2,3,6,7-tetrahydro-1H,5H,11H-pyrano[2,3-f]pyrido[3,2,1-ij]quinolin-9-yl)-N-(4-(tert-butoxy)-4-oxobutyl)benzamido)propane-1-sulfonate (Compound I-9A')

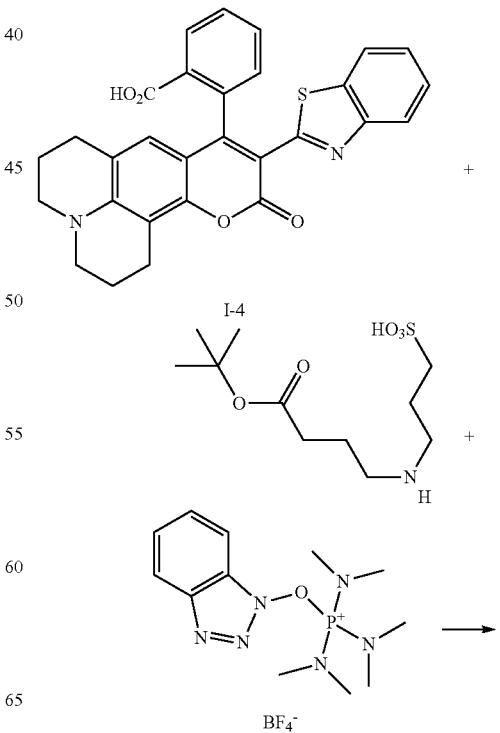

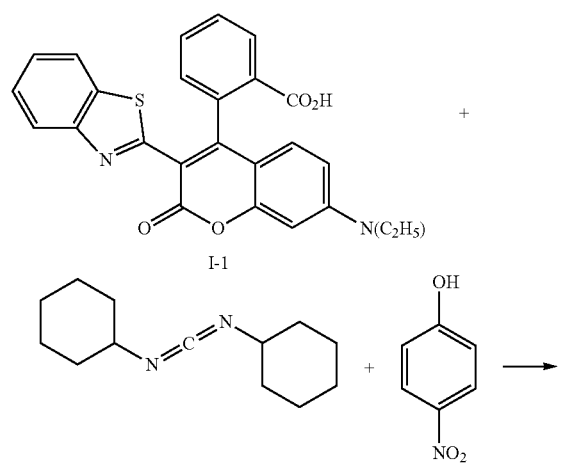

63

-continued

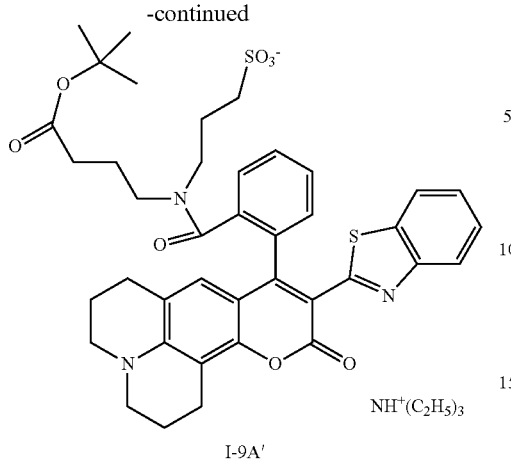

I-9A'

Compound I-4 (150 mg, 0.3 mmol, 1 eq) was dissolved in anhydrous DMA (1.5 ml). To this solution excess of triethylamine (1 mL) and [(1H-benzotriazol-1-yl)oxy]tris(dimethylamino)phosphonium tetrafluoroborate (140 mg, 0.36 mmol, 1.2 eq) as an activation reagent was added. This reaction mixture was stirred at room temperature for about 20 min and then 3-((3-(tert-butoxy)carbonyl)amino)propane-1-sulfonic acid (140 mg, 0.5 mmol, 1.6 eq) was added. Reaction progress was monitored by TLC (Acetonitrile-Water, 10%) and by LCMS.

The reaction mixture was stirred overnight, filtered and excess of activation reagent was quenched with 0.1M TEAB solution in water. Solvents were evaporated in vacuum and the residue was purified by HPLC. Yield: 180 mg (0.21 mmol, 69%). MS (DUIS): MW Calculated 757.25. Found: (−) 756 (M−1), (+) 758 (M+1) for the corresponding protonated anion Compound I-9A:

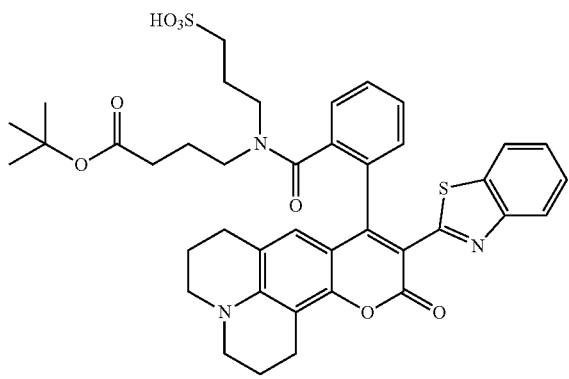

I-9A

64

Example 10

Triethylammonio 4-(2-(10-(benzothiazol-2-yl)-11-oxo-2,3,6,7-tetrahydro-1H,5H,11H-pyrano[2,3-f]pyrido[3,2,1-ij]quinolin-9-yl)-N-(3-sulfonatopropyl)benzamido)butanoate (Compound I-9')

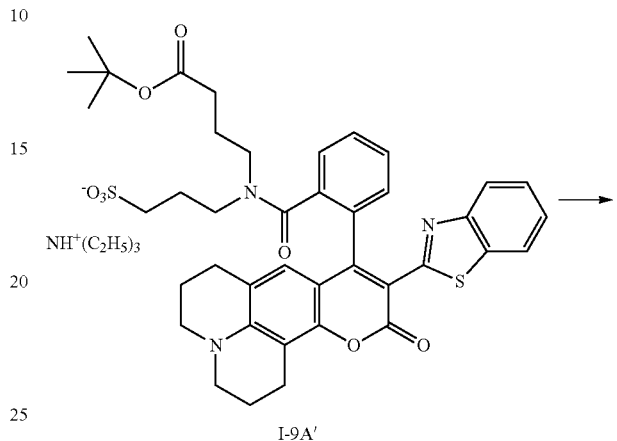

I-9A'

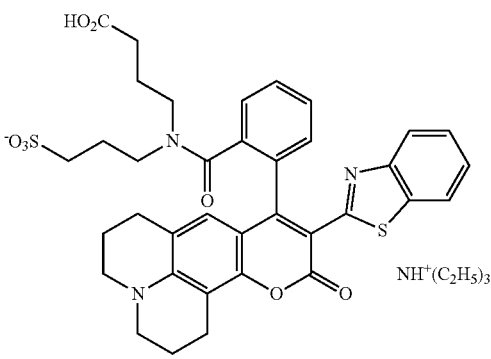

I-9'

Compound I-9A' from the previous step after evaporation of solvents (180 mg, 0.21 mmol) was dissolved in DCM (150 mL) and trifluoroacetic acid (5 mL) was added. The reaction mixture was left at room temperature overnight. Progress of the deprotection reaction was monitored by TLC (Acetonitrile-Water, 10% as an eluent) and by LCMS. DCM was distilled off. The residue was dissolved in acetonitrile and triethylamine (1 mL) was added. The yellow precipitate was filtered off. MS (DUIS): MW Calculated 701.19. Found: (−) 700 (M−1) for the corresponding protonated anion Compound I-9:

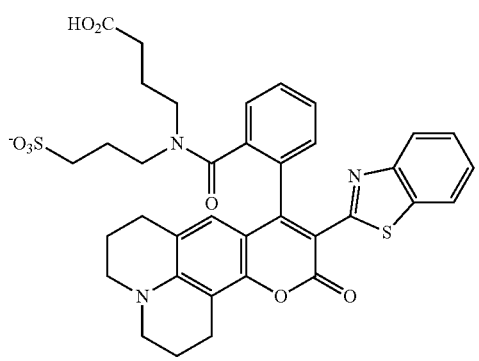

Example 11

Triethylammonio 3-(2-(3-(benzothiazol-2-yl)-7-(diethylamino)-2-oxo-2H-chromen-4-yl)-N-(4-(tert-butoxy)-4-oxobutyl)benzamido)propane-1-sulfonate, (Compound I-6A')

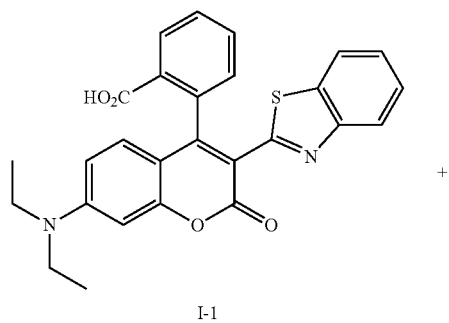

I-1

+

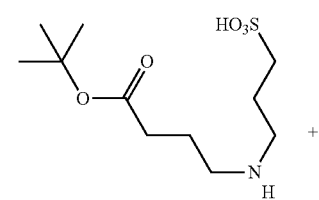

+

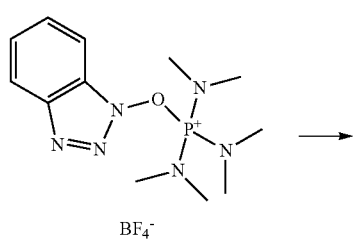

$BF_4^-$ →

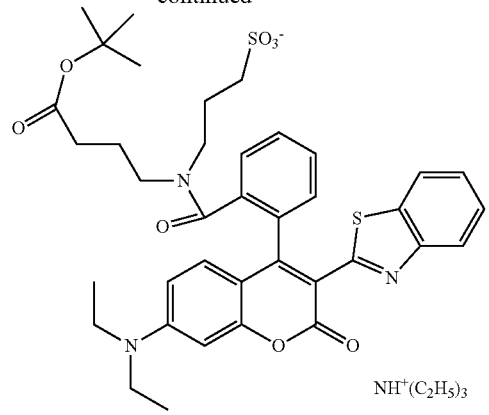

I-6A'

2-(3-(Benzothiazol-2-yl)-7-(diethylamino)-2-oxo-2H-chromen-4-yl) benzoic acid (Compound I-1) (94 mg, 0.2 mmol, 1 eq) was dissolved in anhydrous DMA (2 mL). To this solution excess of N-ethyl-N,N-diisopropylamine (1 mL) was added. To this solution was added [(1H-benzotriazol-1-yl)oxy]tris(dimethylamino)phosphonium tetrafluoroborate (80 mg, 0.21 mmol, 1.04 eq) as an activation reagent. The reaction mixture was stirred at room temperature.

The reaction progress was monitored by TLC (Acetonitrile-Water, 10% as an eluent). Then 3-((3-(tert-butoxy)carbonyl)amino)propane-1-sulfonic acid (70 mg, 0.25 mmol, 1.25 eq) was added. The reaction mixture was stirred overnight at room temperature, filtered and excess of the activation reagent was quenched with 0.1M TEAB solution in water (3 mL). Solvents were evaporated in vacuum and the residue was purified by HPLC. Yield: 113 mg (0.136 mmol, 68%). MS (DUIS): MW Calculated 733.25. Found: (−) 732 (M−1) for the corresponding protonated anion Compound I-6A:

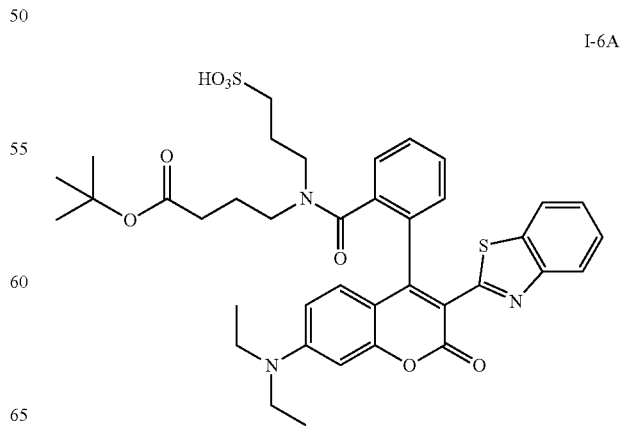

I-6A

Example 12

Triethylammonio 4-(2-(3-(benzothiazol-2-yl)-7-(diethylamino)-2-oxo-2H-chromen-4-yl)-N-(3-sulfonatopropyl)benzamido)butanoate, (Compound I-6')

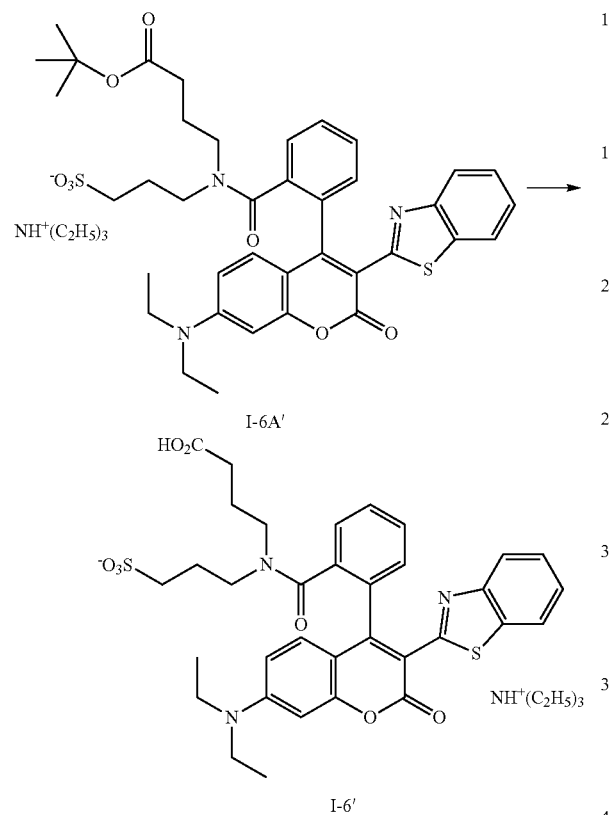

Compound I-6A' (180 mg, 0.21 mmol) from the previous step after evaporation of solvents was dissolved in DCM (50 mL) and trifluoroacetic acid (2.5 mL) was added. The reaction mixture was left with stirring at room temperature overnight. The reaction progress was monitored by TLC (Acetonitrile-Water, 10% as an eluent). Solvent was distilled off and the residue was dissolved in acetonitrile and triethylamine (1.8 mL) added. Acetonitrile and excess of triethylamine was distilled off. To the residue in the flask anhydrous diethyl ether was added and the product was formed as a yellow crystalline precipitate and filtered off. MS (DUIS): MW Calculated 677.19. Found: (−) 676 (M−1) for the acid I-6:

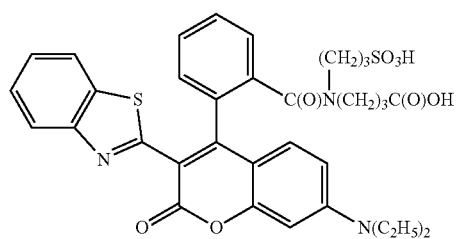

Example 13 tert-Butyl 4-(2-(10-(benzothiazol-2-yl)-11-oxo-2,3,6,7-tetrahydro-1H,5H,11H-pyrano[2,3-f]pyrido[3,2,1-ij]quinolin-9-yl)benzamido)butanoate (I-10A)

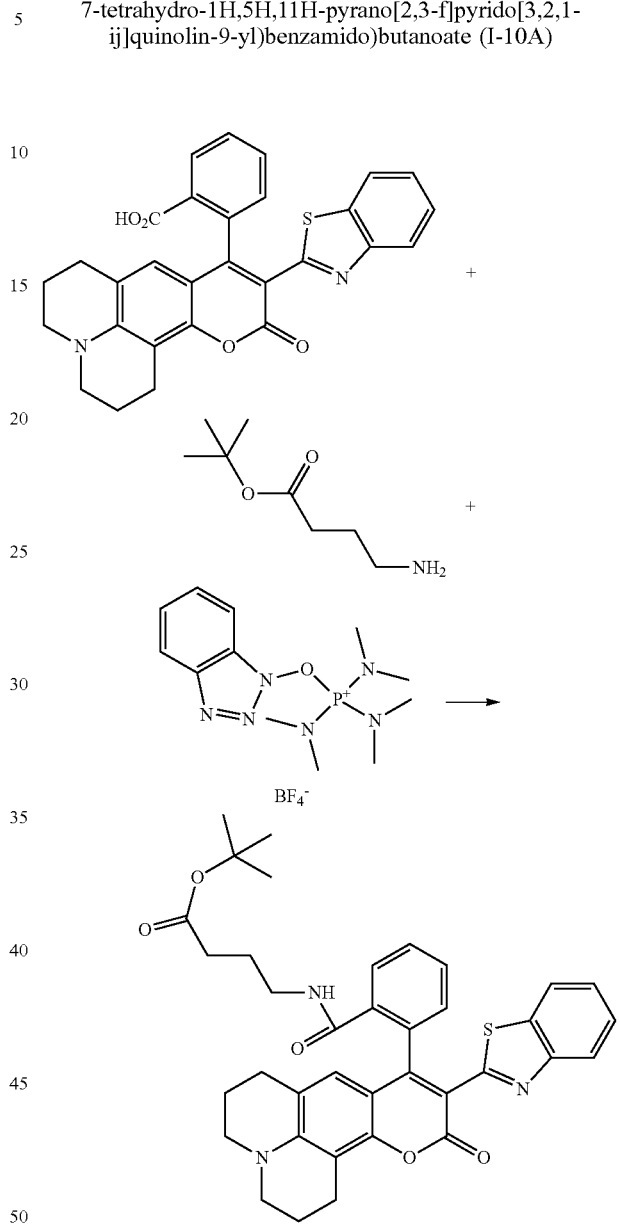

Compound I-4 (97 mg, 0.196 mmol, 1 eq) was dissolved in freshly distilled anhydrous DMF (2.5 mL). To this solution excess of N-ethyl-N,N-diisopropylamine (0.253 mg, 1.961 mmol, 10 eq) and [(1H-benzotriazol-1-yl)oxy]tris(dimethylamino)phosphonium tetrafluoroborate (113 mg, 0.294 mmol, 1.5 eq) as an activation reagent was added. The reaction mixture was stirred at room temperature for about 20 min and then tert-butyl 4-aminobutanoate hydrochloride (58 mg, 0.294 mmol, 1.5 eq) was added. Reaction progress was monitored by TLC (Acetonitrile-Water, 10%) and by LCMS.

The reaction mixture was stirred overnight, filtered and excess of activation reagent was quenched with 0.1M TEAB solution in water. Solvents were evaporated in vacuum and the residue was purified by HPLC. Yield: 105 mg (0.165 mmol, 84%). MS (DUIS): MW Calculated 635.25. Found: (−) 634 (M−1), (+) 636 (M+1).

Example 14

4-(2-(10-(Benzothiazol-2-yl)-11-oxo-2,3,6,7-tetra-hydro-1H,5H,11H-pyrano[2,3-f]pyrido[3,2,1-ij]qui-nolin-9-yl)benzamido)butanoic acid (Compound I-10)

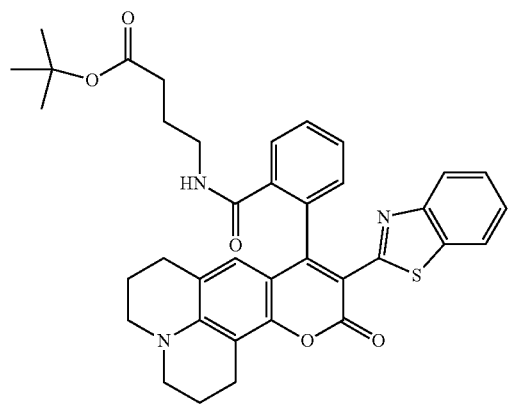

I-10

Compound I-10A (64 mg, 0.1 mmol) from the previous step after evaporation of solvents was dissolved in DCM (25 mL) and trifluoroacetic acid (3.5 mL) was added. The reaction mixture was left at room temperature overnight. The reaction progress was monitored by TLC (Acetonitrile-Water, 10% as an eluent) and by LCMS. Solvents were distilled off. The residue was dissolved in acetonitrile and triethylamine (1 ml) added. Acetonitrile and excess of triethylamine were distilled off. Residue in the flask was dried overnight in vacuum then was sonicated with petroleum ester (25 ml) for 1 hour. Yellow precipitate filtered off. MS (DUIS): MW Calculated 579.18. Found: (−) 578 (M−1), (+) 580 (M+1).

Example 15

4-(2-(10-(Benzothiazol-2-yl)-11-oxo-2,3,6,7-tetra-hydro-1H,5H,11H-pyrano[2,3-f]pyrido[3,2,1-ij]qui-nolin-9-yl)benzamido)butanoic acid (Compound I-7)

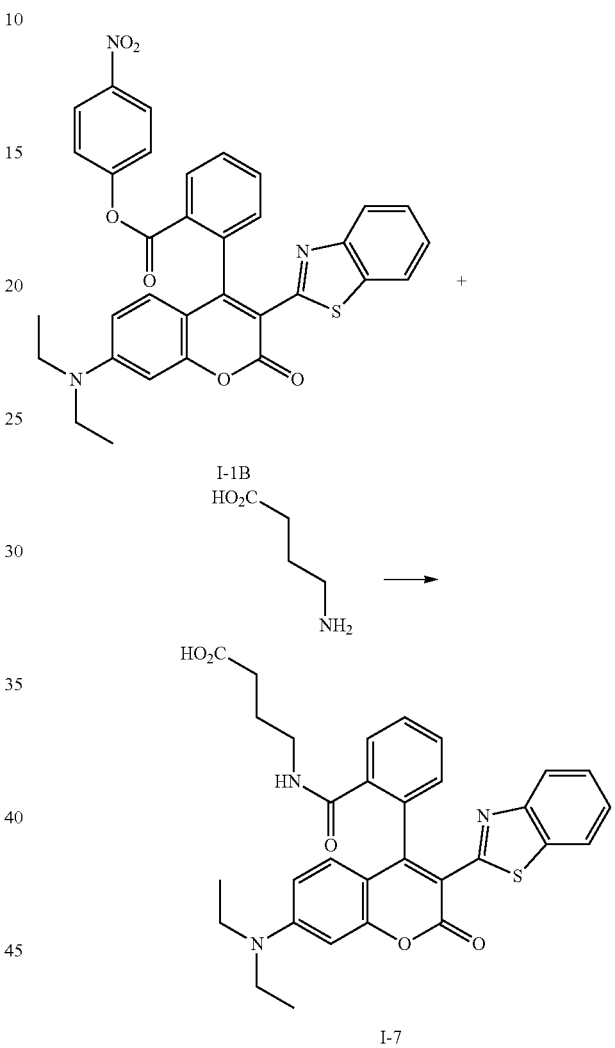

Compound I-1B (180 mg, 0.3 mmol, 1 eq) was dissolved in anhydrous DMF (5 mL) and dimethylaminopyridine (56 mg, 0.45 mmol, 1.5 eq) was added. To this reaction mixture 4-aminobutanoic acid (47 mg, 0.45 mmol, 1.5 eq) was added and this reaction mixture was left at room temperature overnight. The reaction progress was monitored by TLC (Acetonitrile-Water, 10% as an eluent) and by LCMS. Solvents were distilled off in vacuum at room temperature. The residue was diluted with water (25 ml) and the product was formed as a yellow precipitate and filtered off. MS (DUIS): MW Calculated 555.18. Found: (−) 554 (M−1), (+) 556 (M+1).

Example 16

2-(3-(5-Chlorobenzoxazol-2-yl)-7-(diethylamino)-2-oxo-2H-chromen-4-yl)benzoic acid (Compound I-16)

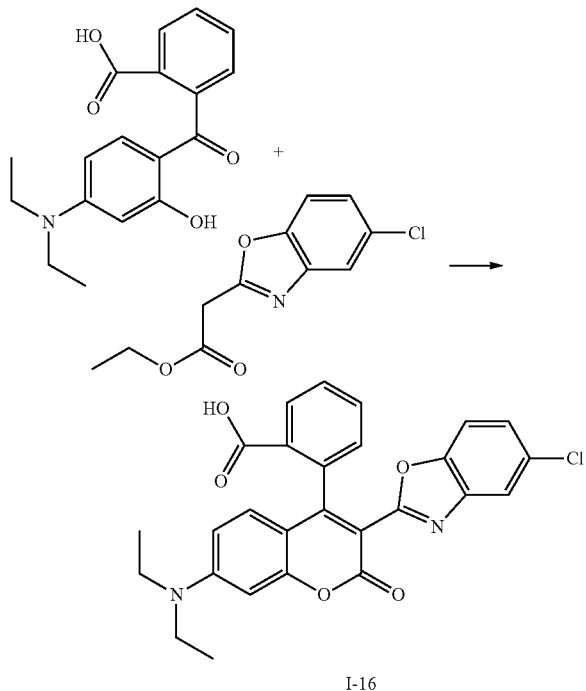

I-16

Mixture of 0.313 g (1.0 mmol, 1 eq) of 2-[4-(diethylamino)-2-hydroxybenzoyl]benzoic acid and 0.263 g (1.1 mmol, 1.1 eq) ethyl 2-(5-chlorobenzoxazol-2-yl)acetate was added with stirring to sulfuric acid (5 mL) at room temperature (about 20° C.). This reaction mixture was stirred at room temperature for 3 hours then heated for 4 hours while stirring at 100° C. Reaction progress was monitored by TLC (DCM-MeOH, 10% as eluent) and by LCMS. Reaction mixture was left at room temperature (about 20° C.) overnight and then was poured into mixture of water-crushed ice (about 100 g) and sodium acetate (about 5 g). After 1 hour, the product was filtered off and washed with water until neutral reaction (pH about 7) and air dried. Yield: 0.453 g (0.93 mmol, 93%). The final product was used without further purification. MS (DUIS): MW Calculated 488.11. Found: (−) 487 (M−1).

Example 17

General Procedure for the Synthesis of Fully Functional Nucleotide Conjugates

New dyes-nucleotide conjugates were synthesized from compounds (I) or compounds (V-O) by coupling with appropriate nucleotides derivatives.

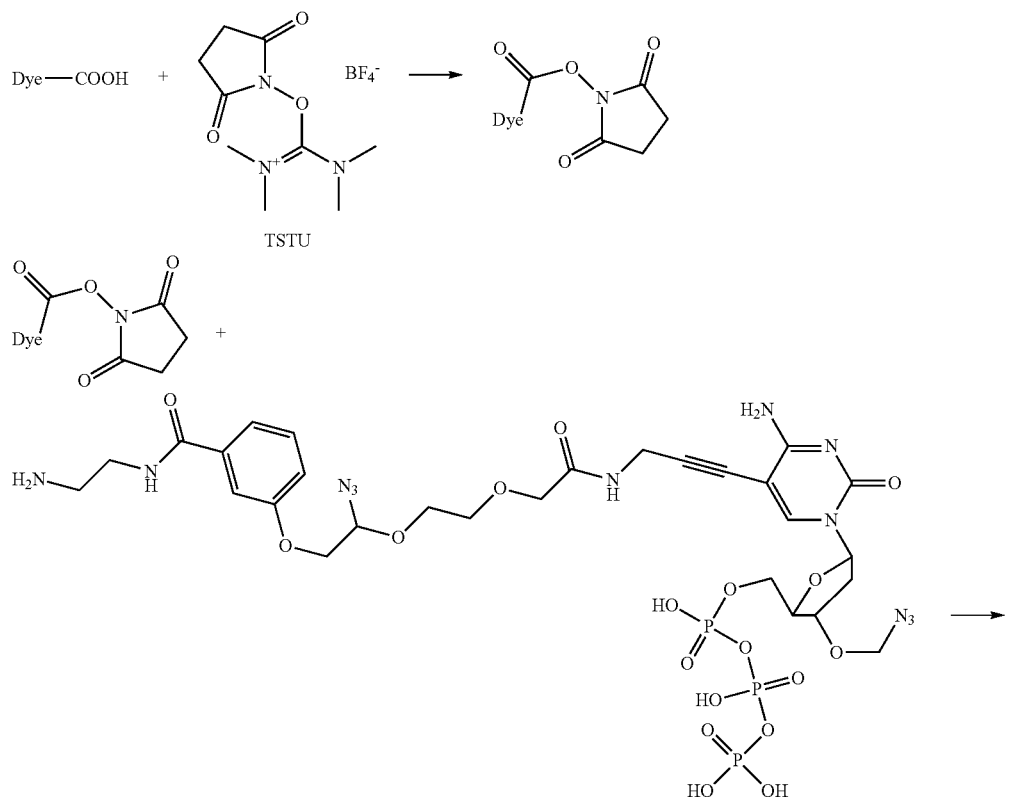

pppC-LN3

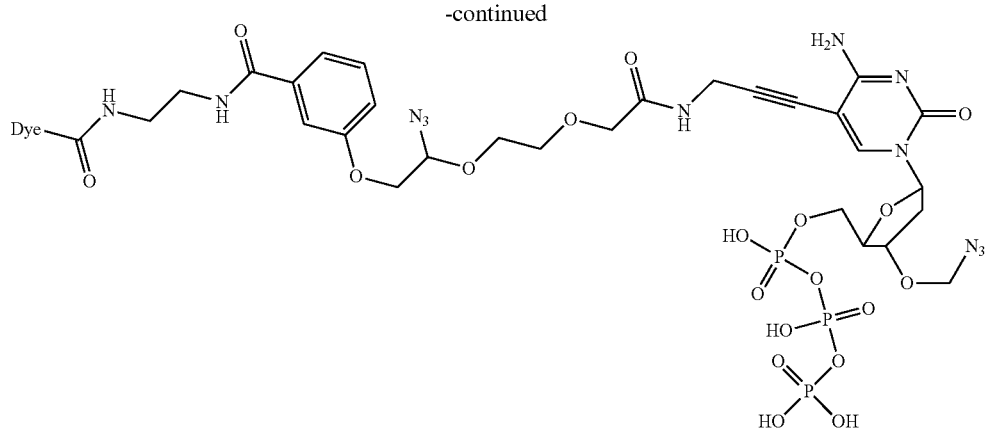

ffC-I

Anhydrous DMA (2.5 mL), N,N,N',N'-Tetramethyl-O—(N-succinimidyl)uronium tetrafluoroborate (20 mg, 60 µmol) and Hunig's Base (0.05 mL) were added to the dried sample of the appropriate dye (50 µmol). The reaction mixture was stirred at room temperature. According to TLC (Acetonitrile-Water, 10%) the activation usually was completed in 20-30 min. After activation was completed, the solution of pppC-LN3 as a triethylammonium salt (55 µmol) in mixture of DMA (0.75 mL) and water (0.30 mL) was added to the reaction mixture. The reaction mixture was stirred at room temperature under nitrogen atmosphere overnight. The reaction mixture was cooled down to about 4° C. with an ice-bath, then a solution of 0.1 M TEAB (5 mL) in water was added and the mixture was stirred at room temperature for 10 min. The reaction mixture was applied to column with about 25 g of DEAE Sephadex resin suspension in 0.05 M TEAB solution in water and washed with TEAB (concentration gradient from 0.1 M up to 1 M). Colored fractions were collected and evaporated then co-evaporated again with water to remove more TEAB and vacuum down to dryness. The residue was then re-dissolved in TEAB 0.1 M. This solution was filtered through a syringe filter 0.2 nm pore size. The product was purified by HPLC using C18 reverse phase column with acetonitrile-0.1 M TEAB. Yield: 60-75%.

Using the general procedure described above, the following nucleotides conjugates were prepared:

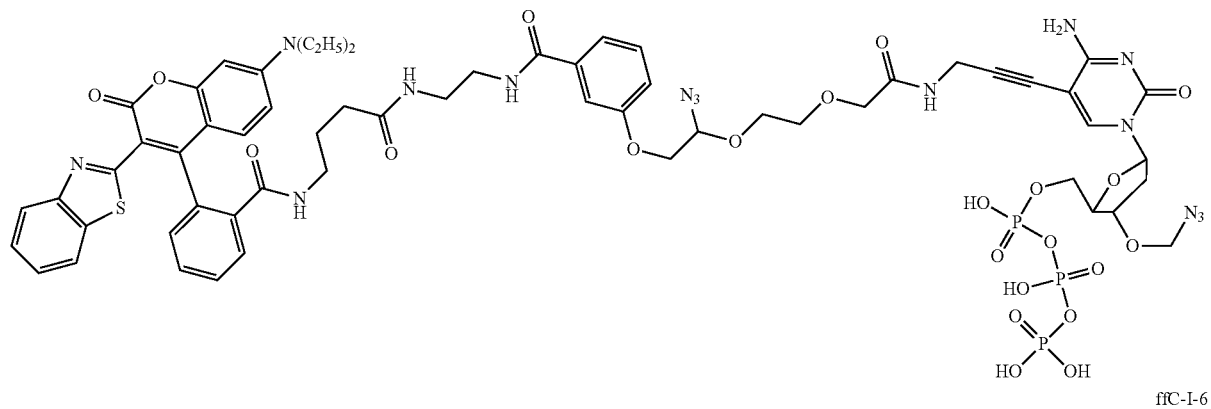

ffC-I-1

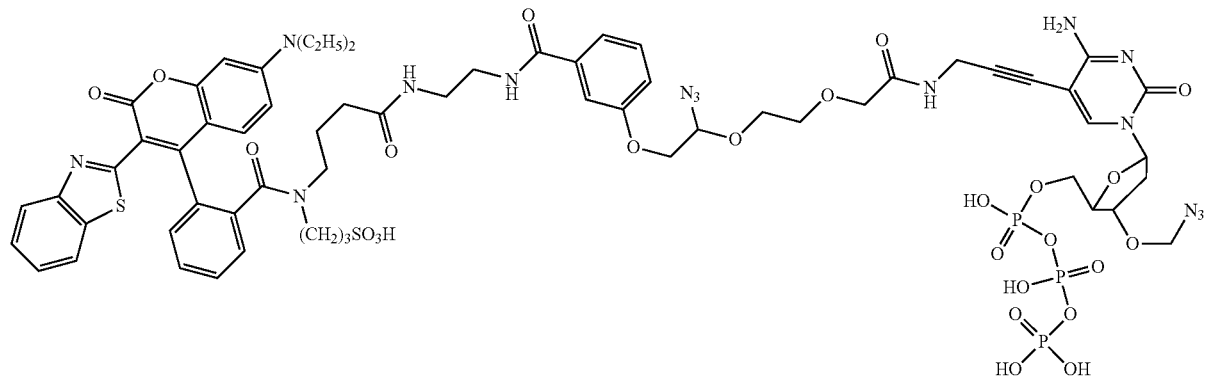

ffC-I-6

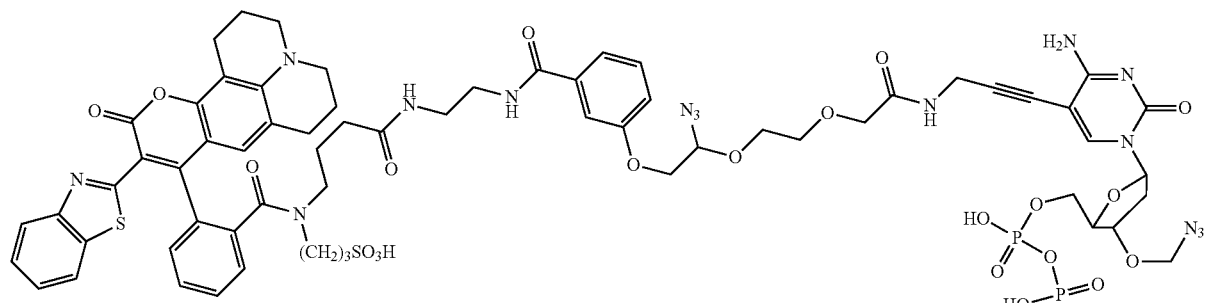

ffC-I-9

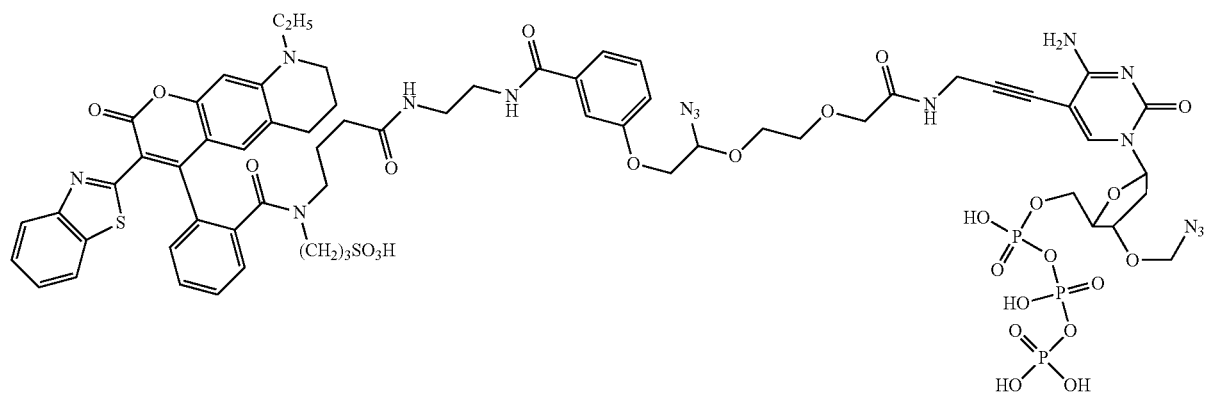

ffC-I-11

Example 18

In this example, the spectral properties of various fluorescent dyes described herein and the corresponding nucleotide conjugates were tested and compared to commercially available dyes.

Table 1A illustrates the spectral properties of the new fluorescent dyes described herein as compared to some exemplary commercial dyes with absorption in the same spectral region in ethanol solution. It can be observed that each of the new fluorescent dyes of the present application have longer Stokes shift compared to Star440sx.

TABLE 1A

Comparison of Spectral Properties Varies Dyes in EtOH solution

| Dyes | Absorption Max (nm) | Emission Max (nm) | Stokes Shift (nm) |
| --- | --- | --- | --- |
| Star440sx* | 433 | 502 | 69 |
| I-9 | 460 | 540 | 80 |
| I-10 | 457 | 543 | 86 |
| I-6 | 450 | 525 | 75 |
| I-1 | 445 | 520 | 75 |
| I-8 | 424 | 510 | 86 |
| I-3 | 427 | 511 | 84 |
| I-5 | 465 | 538 | 73 |

*Star440sx - commercial Long Stokes Shift Dye

In addition, the spectral properties of dye I-1 was compared to the sulfonated dyes I-13 and I-15 in methanol solution and the results were summarized in Table 1B. These data demonstrate that sulfonated derivatives I-13 and I-15 have 2 to 5 times stronger fluorescence in solution when compared with the corresponding unsubstituted analog I-1. These results demonstrates the potential use of the sulfonated dyes as biomarkers.

TABLE 1B

Comparison of Spectral Properties of Sulfonated Dyes in methanol solution

| Dye | Absorption Max (nm) | Fluorescence Max (nm) | Fluorescence intensity (normalized) % | Stokes Shift (nm) |
|---|---|---|---|---|
| I-1 | 410 | 506 | 100 | 95 |
| I-13 | 418 | 511 | 235 | 93 |
| I-15 | 425 | 511 | 496 | 86 |

FIG. 1 illustrates the fluorescent spectra of the new fluorescent dyes of the present application as compared to a commercial dye Star440sx which has absorption in the same spectral region (solution in Universal Scanning Mixture; dyes were excited at 460 nm). Due to the larger Stokes shift, these newly developed dyes can provide more signal in detection region with better separation from excitation light at 460 nm.

Table 2 illustrates the relative fluorescent intensities of C-nucleotide labeled with new dyes as compared with appropriate nucleotide labeled with commercial dye which has absorption in the same spectral region. It shows that the new fluorescent dyes described herein can provide 60-400% more signal at 570 nm (detection region) when excited with light at 460 nm due to their stronger fluorescence and larger Stokes shift.

TABLE 2

Relative Fluorescence Intensities of the Exemplary Labeled Fully Functional C-Nucleotide

| ffC | Intensity @570 nm |
|---|---|
| ffC-star440sx* | 1.0 |
| ffC-I-9 | 3.5 |
| ffC-I-10 | 4.0 |
| ffC-I-6 | 1.6 |
| ffC-I-1 | 2.3 |

Assuming ε for dyes I-1, I-6, I-9 and I-10 30,000
*ε for Star440sx 22,700

Table 3 illustrates the spectral properties of the C-nucleotides labeled with the new fluorescent dyes described herein in solution, which is consistent with the observation in Table 1 that most of nucleotides labeled with the fluorescent dyes of the present application have longer Stokes shift comparing with commercial dye for the same spectral region.

TABLE 3

Spectral Properties of Exemplary Labeled Fully Functionalized C-Nucleotide in Solution

| ffC | Absorption Max (nm) | Emission Max (nm) | Stokes Shift (nm) |
|---|---|---|---|
| ffC-star440sx | 447 | 516 | 69 |
| ffC-I-9 | 475 | 542 | 67 |
| ffC-I-10 | 467 | 545 | 78 |
| ffC-I-6 | 453 | 527 | 74 |
| ffC-I-1 | 449 | 530 | 81 |

FIG. 2 illustrates the usability of the C-nucleotides labeled with the new fluorescent dyes described herein (shown in black) for sequencing analysis. In this sequencing example, the two-channel detection method was used. With respect to the two-channel methods described herein, nucleic acids can be sequenced utilizing methods and systems described in U.S. Patent Application Publication No. 2013/0079232, the disclosure of which is incorporated herein by reference in its entirety. In the two-channel detection, a nucleic acid can be sequenced by providing a first nucleotide type that is detected in a first channel, a second nucleotide type that is detected in a second channel, a third nucleotide type that is detected in both the first and the second channel and a fourth nucleotide type that lacks a label that is not, or minimally, detected in either channel.

Figures 2A, 2B:
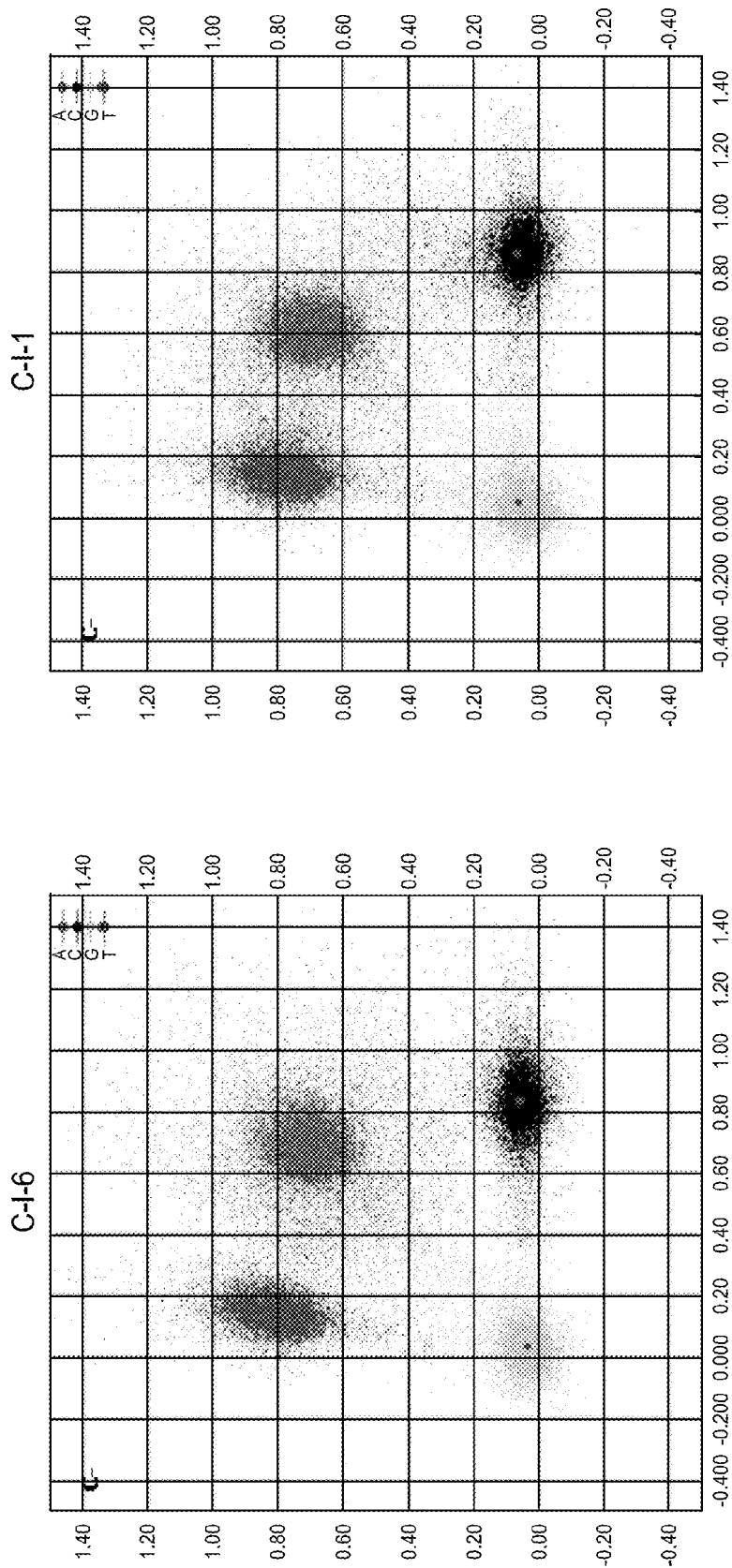
FIGS. 2A and 2B are plots that illustrate the usability of the C-nucleotide labeled with the new fluorescent new dyes as described herein (as shown in black) for sequencing analysis.

In each of FIGS. 2A and 2B, "G" nucleotide is unlabeled and shown as the lower left cloud. There is a mix of two labeled "A" nucleotides, one labeled with a coumarine derivative dye at 0.5 μM and one with the benzopyran derivative I-6 at 1.5 μM, shown as the upper right cloud. The signal from the NR550S0 dye labeled "T" nucleotide is indicated by the upper left cloud, and the labeled "C" nucleotide signal is indicated by the lower right cloud. The X-axis shows the signal intensity for one channel and the Y-axis shows the signal intensity for the other channel. In FIGS. 2A and 2B, the ffC is labeled with I-6 and I-1 respectively. Experiment settings: Instrument: M15 Cycle #: C-I-6 at C5, C-I-1 at C9, Sequencing lib.: standard PhiX. It shows that the fully functional C-nucleotide conjugates labeled with dyes I-6 and I-1 provided sufficient signal intensities and better clouds separation.

Figure 3:
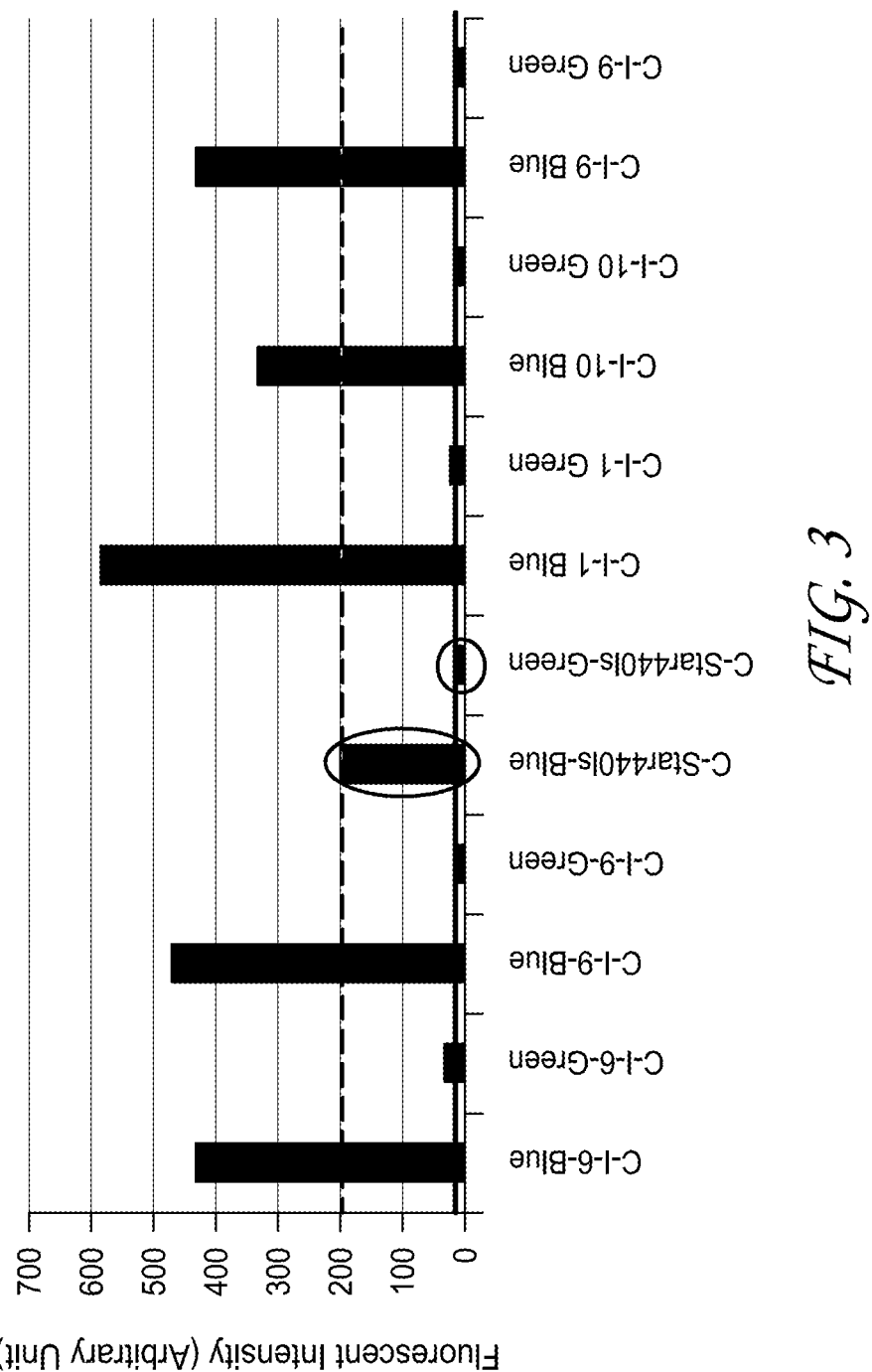
FIG. 3 is a bar chart that illustrates the fluorescent intensity of the C-nucleotide labeled with the new fluorescent dyes as described herein when these dyes were excited with Blue (460 nm) or Green (530 nm) light.

FIG. 3 illustrates the relative fluorescent intensities of the C-nucleotides labeled with various fluorescent dyes when they been excited with Blue (460 nm) or Green (530 nm) light. This bar chart shows the raw intensity of clusters that have incorporated the dye indicated. Each measurement was taken manually at Ex460 nm and exposing for 1 sec at 60° C. MTS [MiSeq R&D (Test) Software] was used on M15 to take the images and image analysis tool Firecrest was used to extract the intensity data.

The results show that the ffCs labeled with the new fluorescent dyes described herein provided up to 300% brighter signal when compared with commercial long Stokes dye for the same spectral region.

Figure 4:
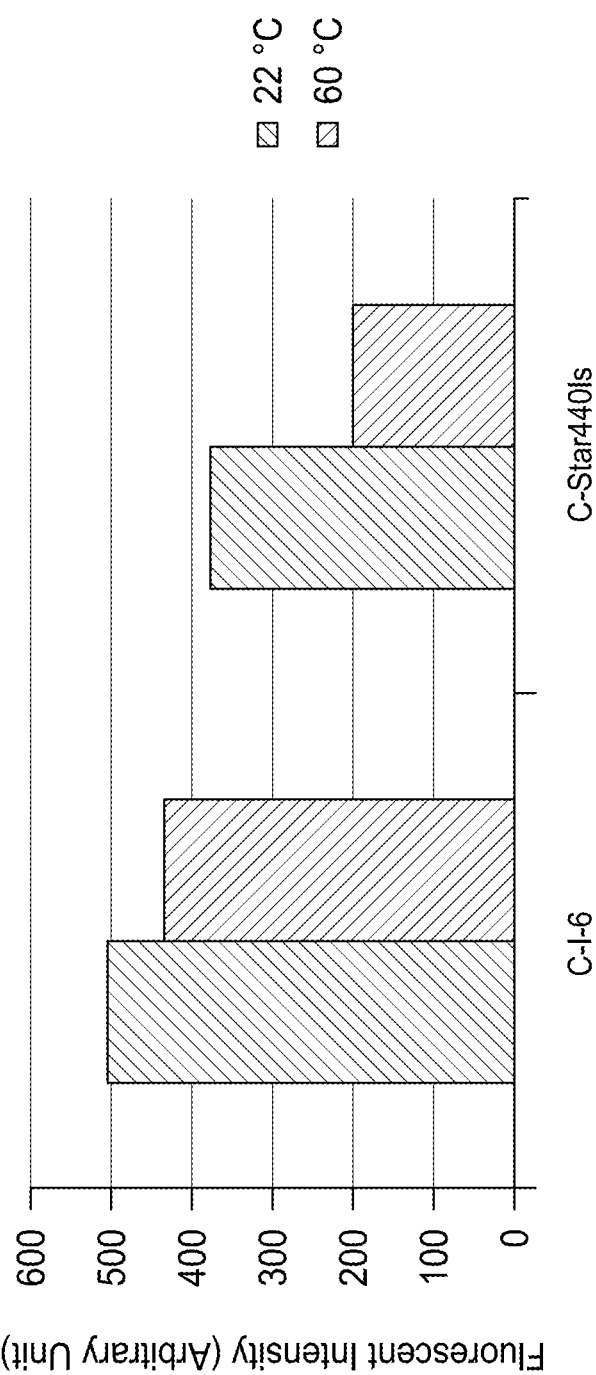
FIG. 4 is a bar chart that illustrates the fluorescent intensity of the C-nucleotide labeled with a new fluorescent dye as described herein as compared to a commercial dye at two different temperatures.

FIG. 4 illustrates the relative brightness of the conjugated C-nucleotides labeled with commercial and new fluorescent dye I-6 when they been excited with Blue (460 nm) light at two different temperatures (room temperature at 22° C. and elevated temperature at 60° C.). The ffC labeled with the new fluorescent dye I-6 provided brighter signal when compared with ffC labeled with commercial long Stokes dye Star440ls for the some spectral region at both temperatures.

The headings and subheadings used herein are only for reading convenience and are not intended to define or limit the scope of the present disclosure. The present application described above relates to compounds and methods that are susceptible to modifications in the methods and materials, as well as alterations in the fabrication methods and equipment. Such modifications will become apparent to those skilled in the art from a consideration of this disclosure or practice of the application disclosed herein. Consequently, it is not intended that the present disclosure be limited to the specific embodiments disclosed herein, but that it cover all modifications and alternatives coming within the true scope and spirit of the disclosure.

What is claimed is:

1. A compound of Formula (I) or mesomeric forms thereof:

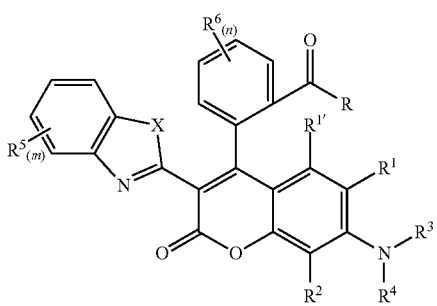

wherein each $R^1$, $R^2$, and $R^{1'}$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl and optionally substituted 5-10 membered heterocyclyl;

alternatively, $R^2$ and $R^4$ together with the atoms to which they are attached form a ring or ring system selected from the group consisting of optionally substituted 5-10 membered heteroaryl and optionally substituted 5-10 membered heterocyclyl;

$R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

R is —$OR^7$ or —$NR^8R^9$;

$R^7$ is selected from the group consisting of H, alkyl, substituted alkyl, optionally substituted aryl, optionally substituted heteroaryl, optionally substituted carbocyclyl, and optionally substituted heterocyclyl;

each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl;

X is selected from the group consisting of O, S, $NR^{10}$, and Se;

$R^{10}$ is selected from the group consisting of H, alkyl, substituted alkyl, optionally substituted aryl, optionally substituted heteroaryl, optionally substituted carbocyclyl, and optionally substituted heterocyclyl;

m is an integer selected from 0 to 4; and n is an integer selected from 0 to 4; provided that when each $R^1$, $R^{1'}$ and $R^2$ is H; each $R^3$ and $R^4$ is ethyl; each m and n is 0; R is —$NHCH(CH_3)CH_2OH$; then X is O, S or Se;

when each $R^1$, $R^{1'}$ and $R^2$ is H; each $R^3$ and $R^4$ is ethyl; each m and n is 0; R is—OH; then X is S or Se;

when each $R^1$, $R^{1'}$ and $R^2$ is H; each $R^3$ and $R^4$ is ethyl; m is 1 and $R^5$ is methyl; n is 0; R is —OH or —OEt; then X is S, $NR^{10}$ or Se; and when each $R^1$, $R^{1'}$ and $R^2$ is H; each $R^3$ and $R^4$ is ethyl; m is 1 and $R^5$ is —$S(O_2)Et$; n is 0; R is —OH or —OEt; then X is S, $NR^{10}$ or Se.

2. The compound of claim 1, wherein X is S or O.

3. The compound of claim 1, wherein R is —$OR^7$.

4. The compound of claim 1, wherein $R^7$ is H or alkyl.

5. The compound of claim 1, wherein R is —$NR^8R^9$.

6. The compound of claim 5, wherein each $R^8$ and $R^9$ is H.

7. The compound of claim 5, wherein $R^8$ is H and $R^9$ is alkyl or substituted alkyl.

8. The compound of claim 5, wherein both $R^8$ and $R^9$ are alkyl or substituted alkyl.

9. The compound of claim 7, wherein substituted alkyl is selected from alkyl substituted with carboxyl or sulfonyl hydroxide.

10. The compound of claim 1, wherein each $R^1$, $R^{1'}$ and $R^2$ is H.

11. The compound of claim 1, wherein at least one of $R^1$, $R^{1'}$ and $R^2$ is an alkyl.

12. The compound of claim 1, wherein each $R^3$ and $R^4$ is an alkyl.

13. The compound of claim 12, wherein each $R^3$ and $R^4$ is selected from methyl or ethyl.

14. The compound of claim 1, wherein $R^3$ is H and $R^4$ is an alkyl.

15. The compound of claim 1, wherein $R^1$ and $R^3$ together with the atoms to which they are attached form an optionally substituted 3 to 7 membered heterocyclyl.

16. The compound of claim 15, wherein $R^1$ and $R^3$ together with the atoms to which they are attached form an optionally substituted 6 membered heterocyclyl.

17. The compound of claim 15, wherein $R^4$ is selected from H or alkyl.

18. The compound of claim 15, wherein at least one of $R^{1'}$ and $R^2$ is H.

19. The compound of claim 1, wherein $R^2$ and $R^4$ together with the atoms to which they are attached form an optionally substituted 3 to 7 membered heterocyclyl.

20. The compound of claim 19, wherein $R^2$ and $R^4$ together with the atoms to which they are attached form an optionally substituted 6 membered heterocyclyl.

21. The compound of claim 19, wherein $R^3$ is selected from H or alkyl.

22. The compound of claim 19, wherein at least one of $R^{1'}$ and $R^1$ is H.

23. The compound of claim 1, wherein $R^1$ and $R^3$ together with the atoms to which they are attached form an optionally substituted 3 to 7 membered heterocyclyl, and wherein $R^2$ and $R^4$ together with the atoms to which they are attached form an optionally substituted 3 to 7 membered heterocyclyl.

24. The compound of claim 23, wherein $R^1$ and $R^3$ together with the atoms to which they are attached form an optionally substituted 3 to 7 membered heterocyclyl, and wherein $R^2$ and $R^4$ together with the atoms to which they are attached form an optionally substituted 6 membered heterocyclyl.

25. The compound of claim 15, wherein the heterocyclyl contains one heteroatom.

26. The compound of claim 24, wherein the heterocyclyl is substituted with one or more alkyl.

27. The compound of claim 1, wherein m is 0.

28. The compound of claim 1, wherein m is 1 and $R^5$ is selected from halo, sulfo, aminosulfonyl, or sulfonyl halide.

29. The compound of claim 1, wherein n is 0.

30. The compound of claim 1, selected from the group consisting of:

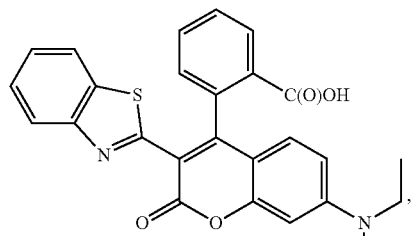

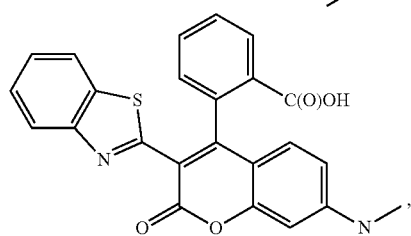

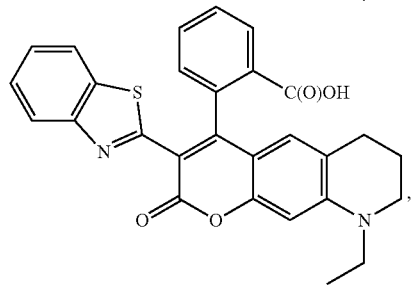

-continued

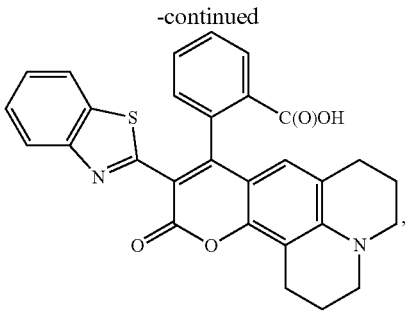

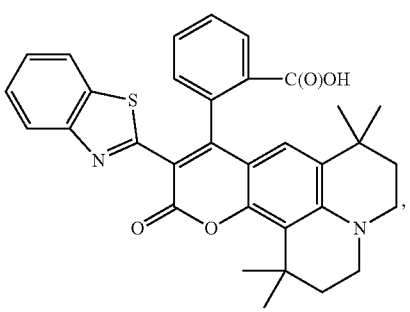

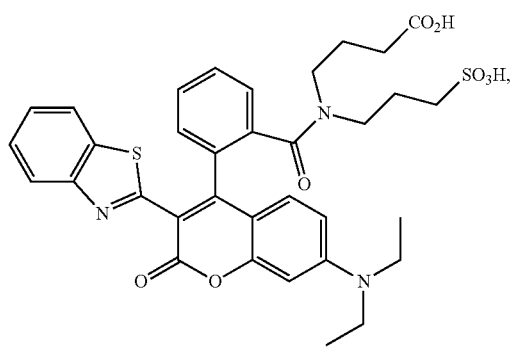

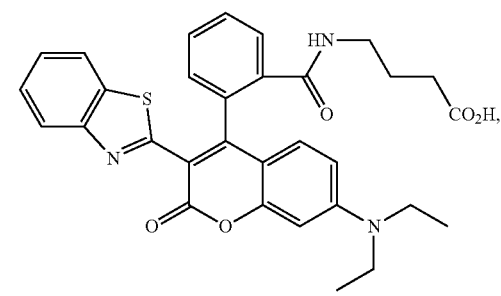

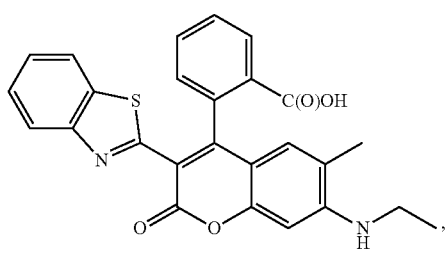

-continued

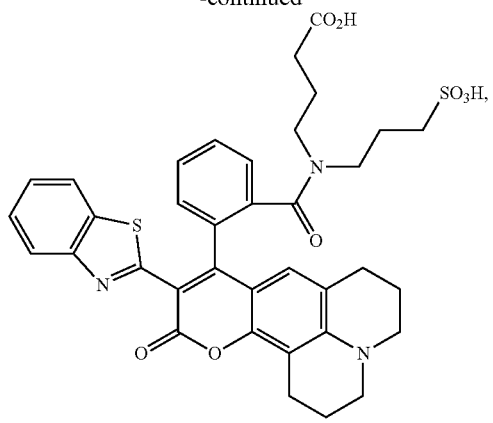

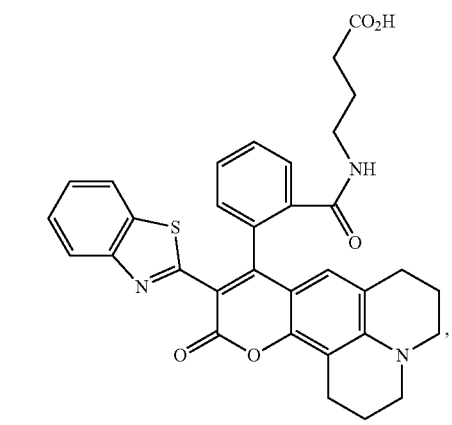

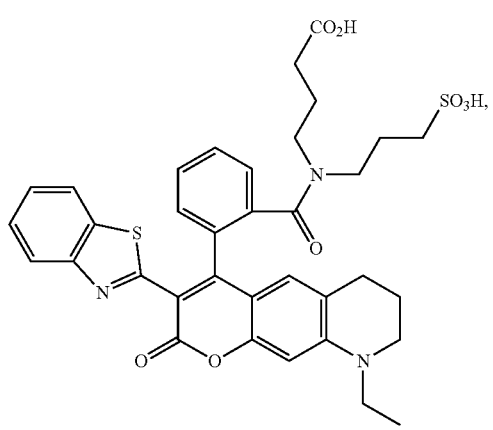

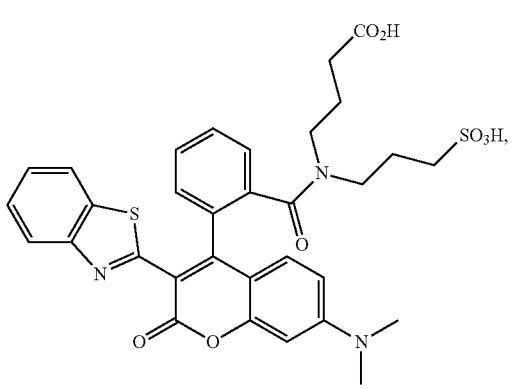

-continued

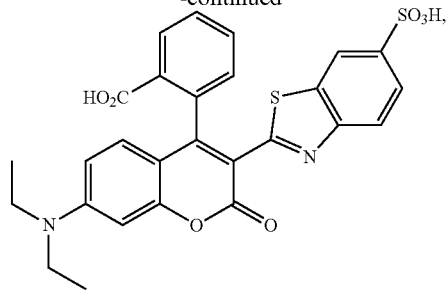

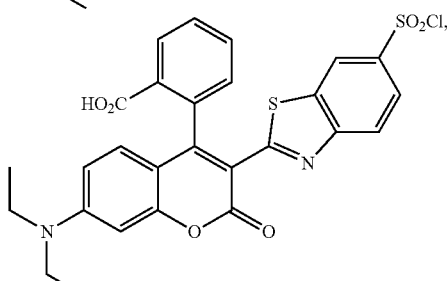

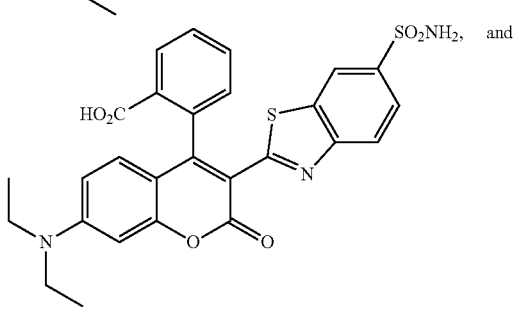

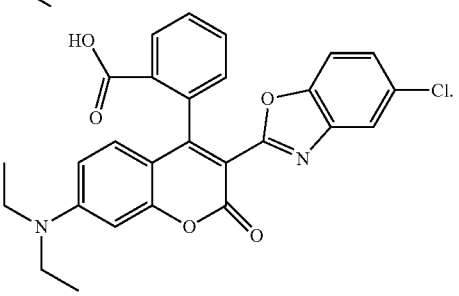

and mesomeric isomers thereof.

31. The compound of claim 1, wherein the compound is covalently attached to a nucleotide or oligonucleotide via C(=O)R, wherein R is —OR$^7$, and wherein R$^7$ is H or a substituted alkyl.

32. The compound of claim 1, wherein the compound is covalently attached to a nucleotide or oligonucleotide via C(=O)R, wherein R is —NR$^8$R$^9$, and wherein at least one of R$^8$ or R$^9$ is a substituted alkyl.

33. A nucleotide or oligonucleotide labeled with a compound according to claim 1.

34. The labeled nucleotide or oligonucleotide of claim 33, wherein the compound is covalently attached to the nucleotide or oligonucleotide via —C(=O)R, wherein R is —OR$^7$, and R$^7$ is H or a substituted alkyl.

35. The labeled nucleotide or oligonucleotide of claim 33, wherein the compound is covalently attached to the nucleotide or oligonucleotide via —C(=O)R, wherein R is —NR$^8$R$^9$, and wherein at least one of R$^8$ or R$^9$ is a substituted alkyl.

36. The labeled nucleotide or oligonucleotide of claim 33, wherein the compound is attached to the C5 position of a pyrimidine base or the C7 position of a 7-deaza purine base of the nucleotide or oligonucleotide through a cleavable linker.

37. The labeled nucleotide or oligonucleotide of claim 33, further comprising a 3'—OH blocking group covalently attached to the ribose or deoxyribose sugar of the nucleotide or oligonucleotide.

38. A kit comprising one or more nucleotides wherein at least one nucleotide is a labeled nucleotide according to claim 33.

39. The kit of claim 38, comprising two or more labeled nucleotides.

40. The kit of claim 39, wherein the two labeled nucleotides are excited using a single laser.

41. The kit of claim 38, further comprising a third and a fourth nucleotide, wherein each of the second, third and fourth nucleotide is labeled with a different compound, wherein each compound has a distinct absorbance maximum and each of the compound is distinguishable from the other compounds.

42. A method of sequencing comprising incorporating a labeled nucleotide according to claim 33 in a sequencing assay.

43. The method of claim 42, further comprising detecting the nucleotide.

44. The method of claim 42, wherein the sequencing assay is performed on an automated sequencing instrument, and wherein the automated sequencing instrument comprises two light sources operating at different wavelengths.

45. A method of preparing a compound of Formula (Ia), comprising:
reacting a compound of Formula (IIa)

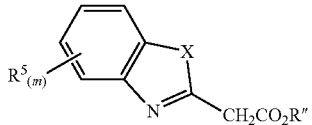
(IIa)

or (IIb)

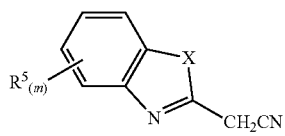
(IIb)

with a compound of Formula (III)

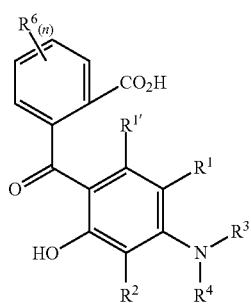
(III)

to form

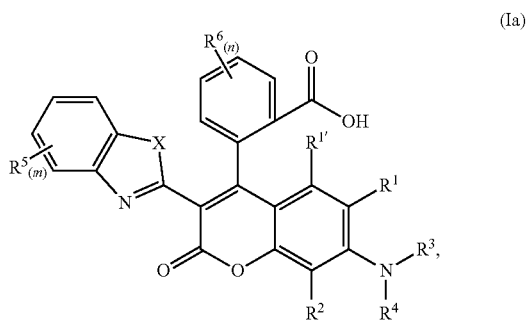
(Ia)

wherein each $R^1$, $R^2$, and $R^{1'}$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl and optionally substituted 5-10 membered heterocyclyl;

alternatively, $R^2$ and $R^4$ together with the atoms to which they are attached form a ring or ring system selected from the group consisting of optionally substituted 5-10 membered heteroaryl and optionally substituted 5-10 membered heterocyclyl;

$R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

X is selected from the group consisting of O, S, $NR^{10}$, and Se;

$R^{10}$ is selected from the group consisting of H, alkyl, substituted alkyl, optionally substituted aryl, optionally substituted heteroaryl, optionally substituted carbocyclyl, and optionally substituted heterocyclyl;

R" is selected from the group consisting of H, optionally substituted alkyl, alkenyl, alkynyl, aminoalkyl, haloalkyl, heteroalkyl, alkoxyalkyl, sulfo, optionally substituted aryl; optionally substituted heteroaryl, optionally substituted carbocyclyl, and optionally substituted heterocyclyl;

m is an integer selected from 0 to 4; and n is an integer selected from 0 to 4.

46. A method for preparation a compound of Formula (Ib), comprising:

converting a compound of Formula (Ia) to a compound of Formula (Ia') through carboxylic acid activation;

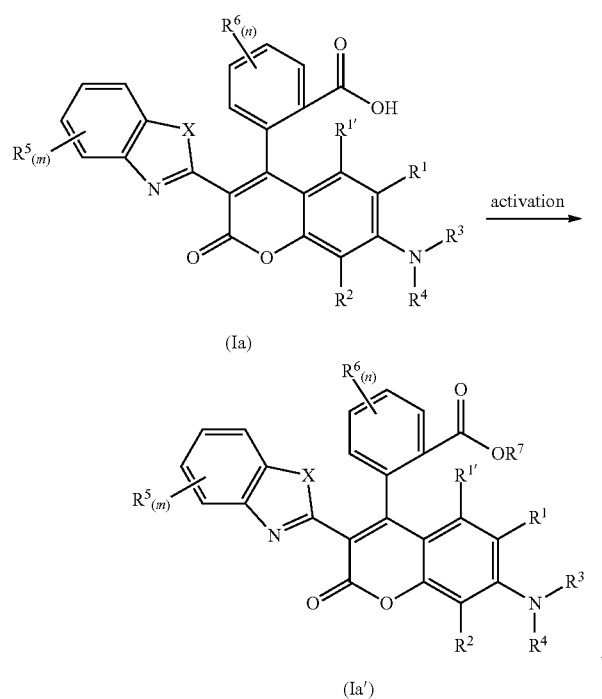

and reacting the compound of Formula (Ia') with a primary or secondary amine of Formula (IV),

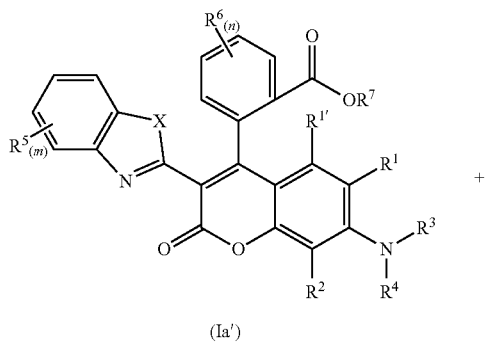

wherein the compound of Formula (Ia) is prepared according to claim 45;

$R^7$ is selected from the group consisting of H, alkyl, substituted alkyl, optionally substituted aryl, optionally substituted heteroaryl, optionally substituted carbocyclyl, and optionally substituted heterocyclyl; and each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl.

* * * * *